(12) United States Patent
Liu et al.

(10) Patent No.: US 7,256,923 B2
(45) Date of Patent: Aug. 14, 2007

(54) SWITCHABLE WINDOW BASED ON ELECTROCHROMIC POLYMERS

(75) Inventors: Lu Liu, Seattle, WA (US); Chunye Xu, Seattle, WA (US); Susan E. Legenski, Hermosa Beach, CA (US); Minoru Taya, Mercer Island, WA (US)

(73) Assignee: University of Washington, Seattle, WA (US)

( * ) Notice: Subject to any disclaimer, the term of this patent is extended or adjusted under 35 U.S.C. 154(b) by 176 days.

(21) Appl. No.: 11/070,392

(22) Filed: Mar. 1, 2005

(65) Prior Publication Data
US 2005/0200935 A1    Sep. 15, 2005

Related U.S. Application Data

(60) Continuation-in-part of application No. 10/917,954, filed on Aug. 13, 2004, and a continuation-in-part of application No. 10/755,433, filed on Jan. 12, 2004, now Pat. No. 7,002,722, which is a division of application No. 10/180,222, filed on Jun. 25, 2002, now Pat. No. 6,747,780.

(60) Provisional application No. 60/549,035, filed on Mar. 1, 2004, provisional application No. 60/523,007, filed on Nov. 18, 2003, provisional application No. 60/495,310, filed on Aug. 14, 2003, provisional application No. 60/364,418, filed on Mar. 14, 2002, provisional application No. 60/324,205, filed on Sep. 21, 2001, provisional application No. 60/300,675, filed on Jun. 25, 2001.

(51) Int. Cl.
*G02F 1/15* (2006.01)

(52) U.S. Cl. .................. 359/265; 359/273; 359/267

(58) Field of Classification Search ............... 359/265
See application file for complete search history.

(56) References Cited

U.S. PATENT DOCUMENTS

| 4,933,106 A | 6/1990 | Sakai et al. .................. 252/500 |
| 4,993,810 A | 2/1991 | Demiryont .................. 350/357 |

(Continued)

OTHER PUBLICATIONS

Sapp, Shawn A. et al. 1998, "*High Contrast Ratio and Fast-Switching Dual Polymer Electrochromic Devices.*" *Chem. Mater.* 10: 2101-2108.

(Continued)

*Primary Examiner*—Jordan Schwartz
*Assistant Examiner*—Jessica Stultz
(74) *Attorney, Agent, or Firm*—Ronald M. Anderson

(57) ABSTRACT

Syntheses of a new blue EC monomer (ProDOT-MePro), and a new red EC monomer (ProDOP-Et2) are described. Two additional new types of EC monomers based on 3,4-alkylenedioxythiophene include fluorinated EC monomers and an EC monomer including silicon. EC polymer devices having more than one different color EC polymer to enable additional colors to be provided using subtractive color mixing are also described, as well as EC polymer devices incorporating a logo, image, or text, are generally obscured when the device is colored, but become visible when the device is not colored. Also described are EC polymer devices that include a cathodic EC polymer layer, a gel electrolyte, a counter electrode, and a reference electrode. Working prototypes of such devices exhibit significant increases in the speed of transition of the EC device from a colored state to a transparent state.

29 Claims, 23 Drawing Sheets

*TRANSPARENT/OXIDIZED STATE*
*NO VOLTAGE APPLIED (OR POSITIVE VOLTAGE APPLIED)*

U.S. PATENT DOCUMENTS

| | | | |
|---|---|---|---|
| 5,006,633 A | 4/1991 | Shikatani et al. | 528/230 |
| 5,042,923 A | 8/1991 | Wolf et al. | 359/275 |
| 5,187,034 A | 2/1993 | Otagawa et al. | 429/213 |
| 5,321,544 A * | 6/1994 | Parkhe et al. | 359/273 |
| 5,598,293 A | 1/1997 | Green | 359/275 |
| 5,699,192 A | 12/1997 | Van Dine et al. | 359/269 |
| 5,724,176 A | 3/1998 | Nishikitani et al. | 359/271 |
| 5,818,636 A * | 10/1998 | Leventis et al. | 359/273 |
| 5,883,220 A | 3/1999 | Armand et al. | 528/322 |
| 5,888,431 A | 3/1999 | Tonar et al. | 252/583 |
| 5,905,590 A | 5/1999 | Van Der Sluis et al. | 359/275 |
| 6,005,705 A | 12/1999 | Schmidt et al. | 359/265 |
| 6,011,642 A | 1/2000 | Vink et al. | 359/273 |
| 6,136,161 A | 10/2000 | Yu et al. | 204/192.29 |
| 6,197,923 B1 | 3/2001 | Yamamoto | 528/424 |
| 6,373,618 B1 | 4/2002 | Agrawal et al. | 359/265 |
| 6,555,945 B1 | 4/2003 | Baughman et al. | 310/300 |
| 6,589,383 B1 | 7/2003 | Takaoka et al. | 156/313 |
| 6,617,462 B1 | 9/2003 | Tan et al. | 549/29 |
| 6,667,825 B2 | 12/2003 | Lu et al. | 359/265 |
| 6,728,022 B2 * | 4/2004 | Asano et al. | 359/265 |
| 6,730,212 B1 | 5/2004 | Yamagishi et al. | 205/777.5 |
| 6,734,956 B2 | 5/2004 | Byrne et al. | 356/128 |
| 6,791,738 B2 | 9/2004 | Reynolds et al. | 359/265 |
| 6,828,062 B2 | 12/2004 | Lu et al. | 429/213 |
| 6,906,842 B2 * | 6/2005 | Agrawal et al. | 359/265 |
| 2003/0072071 A1 | 4/2003 | Asano et al. | 359/265 |
| 2003/0174377 A1 | 9/2003 | Reynolds et al. | 359/265 |

OTHER PUBLICATIONS

Welsh, Dean M. et al. 1999. "*Enhanced Contrast Ratios and Rapid Switching in Electrochromics Based on Poly (3,4-propylenediozythiophene) Derivitives.*" Advanced Materials. 11:16 1379-1382.

Schwenderman, Irina et al. 2001. "*Combined Visible and Infrared Electrochromism Using Dual Polymer Devices.*" Advanced Materials. 13:9 634-637.

* cited by examiner

*TRANSPARENT/OXIDIZED STATE*
*NO VOLTAGE APPLIED (OR POSITIVE VOLTAGE APPLIED)*

*COLORED/REDUCED STATE*
*VOLTAGE APPLIED (NEGATIVE VOLTAGE APPLIED)*

CATHODIC EC POLYMER: PPRODOT-ME$_2$:
POLY[3,3- DIMETHYLE -3,4- DIHYDRO -2H- THIENO [3,4-B][1,4] DIOXEPINE]

ANODIC EC POLYMER: PBEODOT-NCH$_3$Cz:
POLY[3,6-BIS(2-(3,4-ETHYLENEDIOXYTHIOPHENE))-N-METHYLCARBAZOLE

*TRANSPARENT/OXIDIZED STATE*
*NO VOLTAGE APPLIED (OR POSITIVE VOLTAGE APPLIED)*

*COLORED/REDUCED STATE*
*VOLTAGE APPLIED (NEGATIVE VOLTAGE APPLIED)*

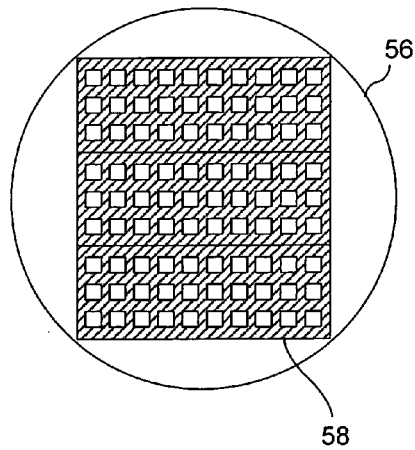
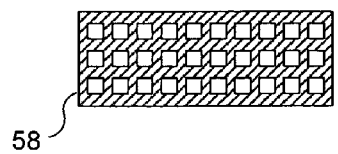
FIG. 19B
FIG. 19C
FIG. 19A
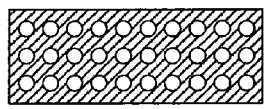
FIG. 19D
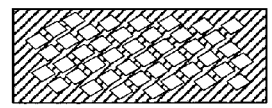
FIG. 19E
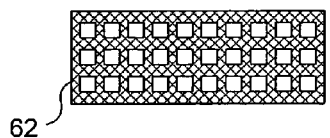
FIG. 19F
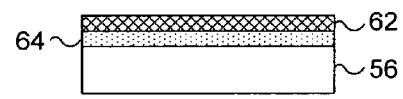
FIG. 19G
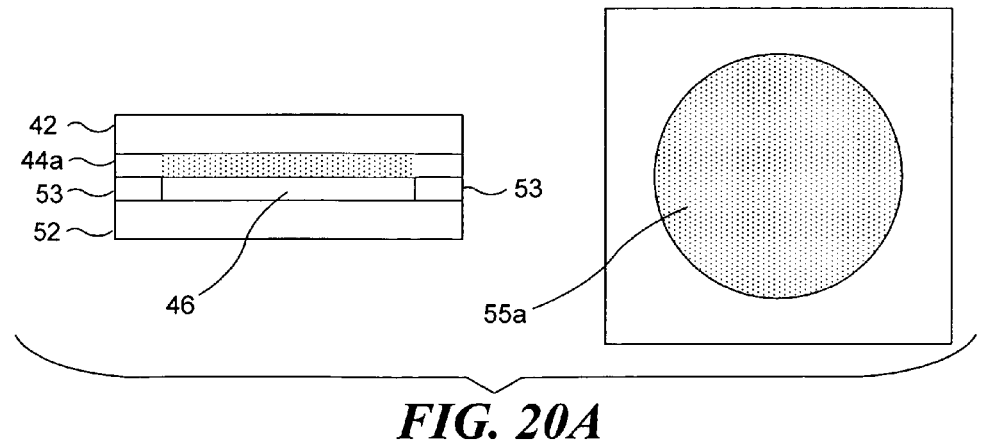
FIG. 20A

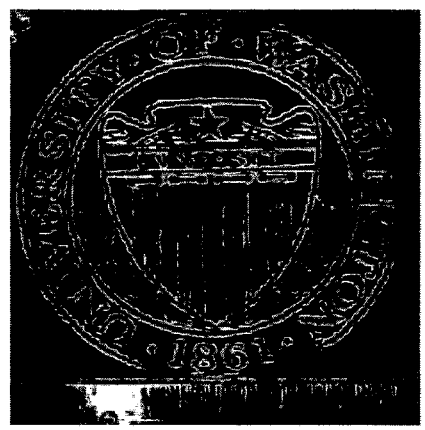
*FIG. 20E*
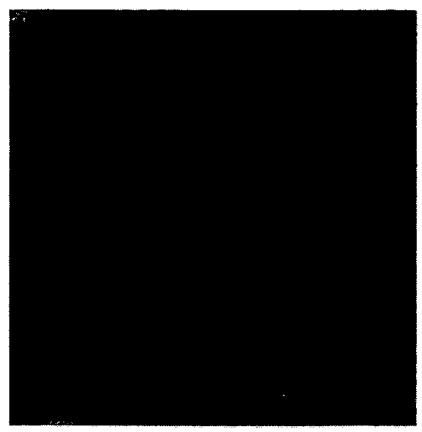
*FIG. 20F*
*FIG. 21*
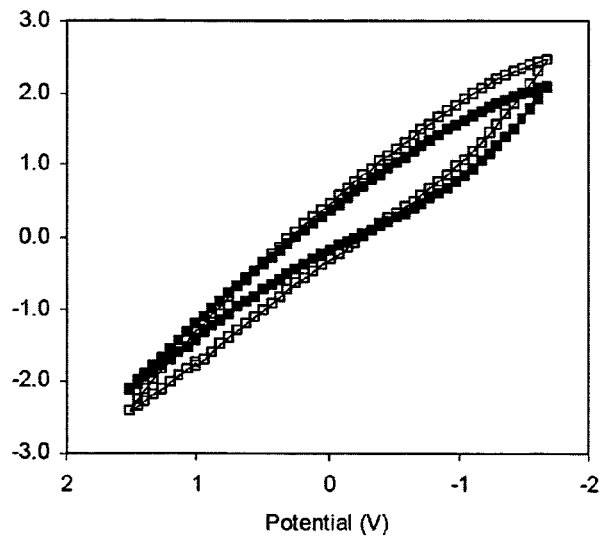
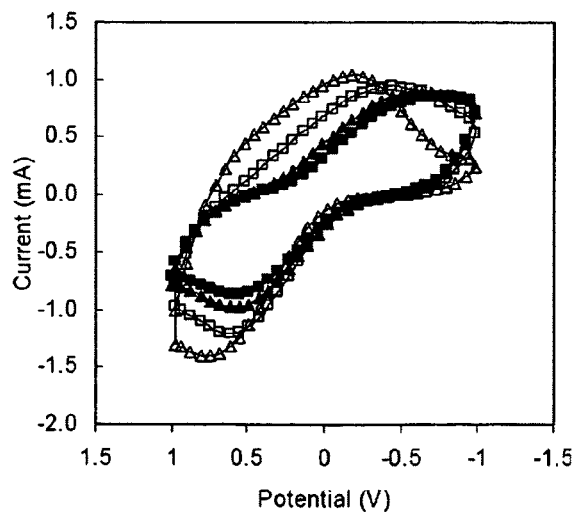
*FIG. 23*

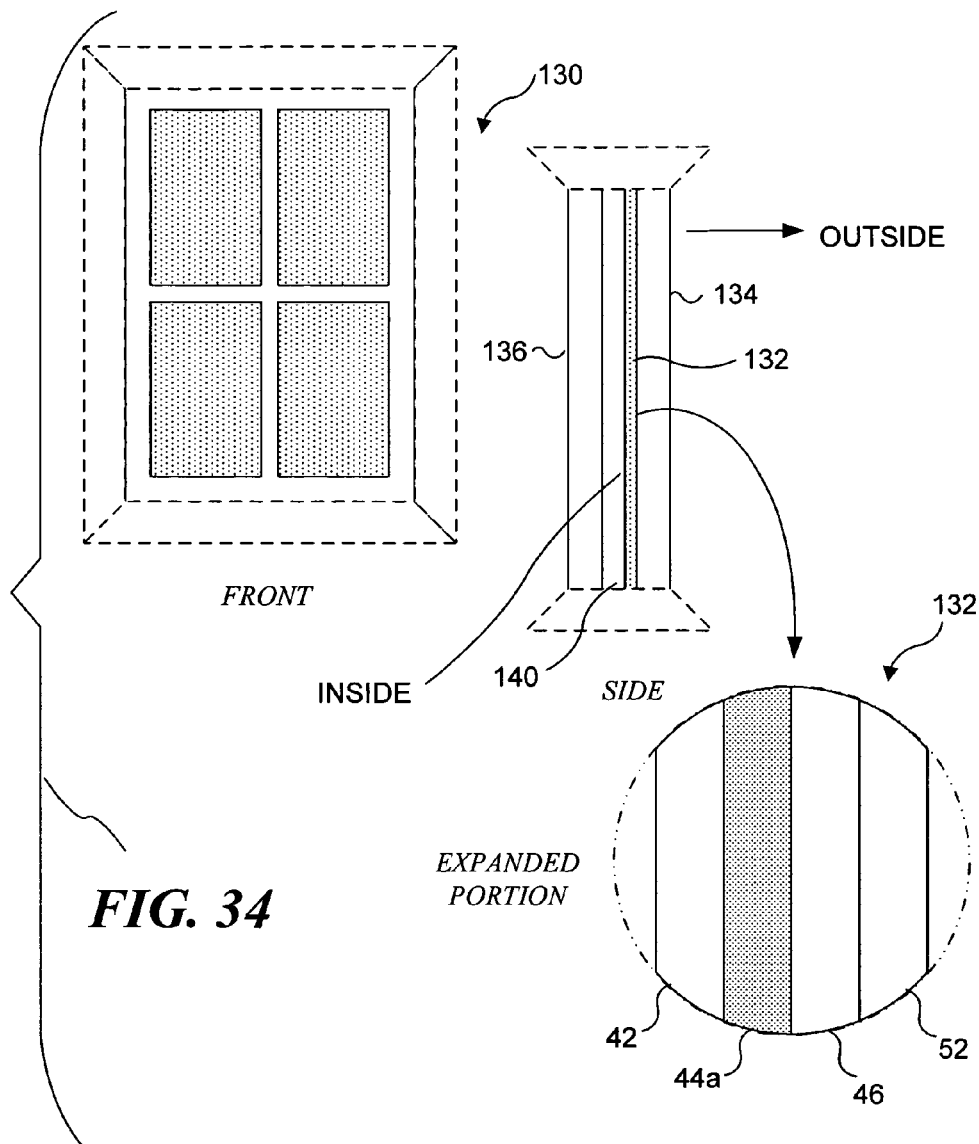
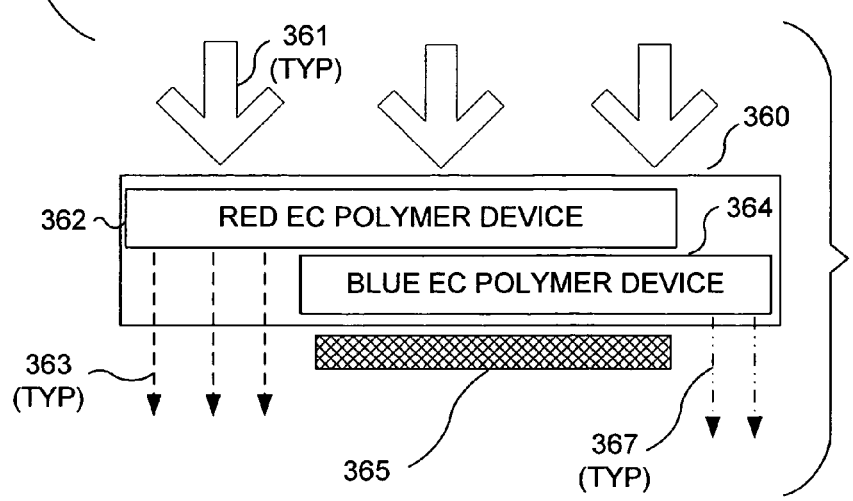
FIG. 34
FIG. 36

SWITCHABLE WINDOW BASED ON ELECTROCHROMIC POLYMERS

RELATED APPLICATIONS

This application is based on a prior provisional application Ser. No. 60/549,035, filed on Mar. 1, 2004, the benefit of the filing date of which is hereby claimed under 35 U.S.C. § 119(e). In addition, this application is a continuation-in-part of a patent application Ser. No. 10/917,954, filed on Aug. 13, 2004, which itself is based on two prior provisional applications, Ser. No. 60/495,310, filed on Aug. 14, 2003, and Ser. No. 60/523,007, filed on Nov. 18, 2003, the benefits of the filing dates of which are hereby claimed under 35 U.S.C. § 119(e) and 120. patent application Ser. No. 10/917, 954 is also a continuation-in-part of a patent application Ser. No. 10/755,433, filed Jan. 12, 2004, now issued as U.S. Pat. No. 7,002,722, which in turn is a divisional of prior application Ser. No. 10/180,222, filed Jun. 25, 2002, now U.S. Pat. No. 6,747,780, which is based on three provisional applications, Ser. No. 60/300,675, filed Jun. 25, 2001, Ser. No. 60/324,205, filed Sep. 21, 2001, and Ser. No. 60/364, 418, filed Mar. 14, 2002, the benefit of the filing dates of which are hereby claimed under 35 U.S.C. §§ 119(e) and 120.

FIELD OF THE INVENTION

The present invention generally relates to electrochromic (EC) materials that exhibit different colors as a function of an applied voltage, and more specifically, to apparatus utilizing specific organic polymer-based EC materials, and methods of producing the specific organic polymer-based EC materials.

BACKGROUND OF THE INVENTION

Electrochromic (EC) materials are a subset of the family of chromogenic materials, which includes photochromic materials, and thermochromic materials. These materials change their tinting level or opacity when exposed to light (photochromic), heat (thermochromic), or an electric potential (electrochromic). Chromogenic materials have attracted widespread interest in applications relating to the transmission of light.

An early application for chromogenic materials was in sunglasses or prescription eyeglasses that darken when exposed to the sun. Such photochromic materials were first developed by researchers at Corning Incorporated in the late 1960s. Since that time, it has been recognized that chromogenic materials could potentially be used to produce window glass that can vary the amount of light transmitted, although the use of such materials is clearly not limited to that prospective application. Indeed, EC technology is already employed in the displays of digital watches.

Several different distinct types of EC materials are known. Three primary types are: inorganic thin films, organic polymer films, and organic solutions. For many applications, the use of a liquid material is inconvenient, and as a result, inorganic thin films and organic polymer films appear to have more industrial applications.

For inorganic thin film-based EC devices, the EC layer is typically tungsten oxide ($WO_3$). U.S. Pat. Nos. 5,598,293; 6,005,705; and 6,136,161 describe an inorganic thin film EC device based on a tungsten oxide EC layer. Other inorganic EC materials, such as molybdenum oxide, are also known. While many inorganic materials have been used as EC materials, difficulties in processing and a slow response time associated with many inorganic EC materials have created the need for different types of EC materials.

Conjugated, redox-active polymers represent one different type of EC material. These polymers (cathodic or anodic polymers) are inherently electrochromic and can be switched electrochemically or chemically, between different color states. A family of redox-active copolymers are described in U.S. Pat. No. 5,883,220. Another family of nitrogen based heterocyclic organic EC materials is described in U.S. Pat. No. 6,197,923. Research into still other types of organic film EC materials continues, in hopes of identifying or developing EC materials that will be useful in EC windows. There still exists room for improvement and development of new types of EC organic polymer films, and methods of making EC organic polymer films. For example, it would be desirable to develop EC organic polymer films and methods for making the same that provide certain desirable properties, such as specific colors, long-term stability, rapid redox switching, and large changes in opacity with changes of state.

To make an EC device that exhibits different opacities in response to a voltage, a multilayer assembly is required. In general, the two outer layers of the assembly are transparent electronic conductors. Within the outer layers is a counter-electrode layer and an EC layer, between which is disposed an ion conductor layer. When a low voltage is applied across the outer conductors, ions moving from the counter-electrode to the EC layer cause the assembly to change color. Reversing the voltage moves ions from the EC layer back to the counter-electrode layer, restoring the device to its previous state and color. All of the layers are preferably transparent to visible light. While some configurations of counter-electrodes are known, it would be desirable to provide additional counter-electrode configurations, to facilitate the development of new and improved EC devices.

SUMMARY OF THE INVENTION

The present invention relates to EC monomer and polymers, and EC polymer devices. A first aspect of the present invention is directed to the synthesis of a new EC monomer, 3-methyl-3'-propyl-3,4-dihydro-2H-thieno(3,4-b)(1,4)dioxepine. This new monomer can be readily polymerized to achieve an EC polymer. The new EC monomer is generally related to 3,4-dimethoxylthiophene, from which a plurality of different EC monomers have been produced. Significantly, known EC monomers based on 3,4-dimethoxylthiophene have symmetrical structures, but the newly developed EC monomer has an asymmetrical structure. This new EC monomer, also referred to as ProDOT-MePro, is blue in color and can be beneficially incorporated into a plurality of different EC polymer devices, as a cathodic polymer. A detailed description of the synthesis is set forth below.

Yet another aspect of the present invention is directed to the synthesis of a new red EC monomer, 3,3-diethyl-3,4-dihydro-2H,7H-(1,4)dioxepino(2,3-c)pyrrole, also referred to as PProDOP-Et2. This new monomer can also be beneficially incorporated into a plurality of different EC polymer devices, as a cathodic polymer. A detailed description of the synthesis of PProDOP-Et2 is provided below.

The present invention is also directed to the synthesis of two types of EC monomers based on 3,4-alkylenedioxythiophene. A first such new type of EC monomer incorporates electron withdrawing groups into the EC monomer, in the form of fluorinated groups. A second new type of EC monomer incorporates electron adding groups into the EC monomer, in the form of silicon. One new fluorinated EC monomer is 3,4-bis-(2,2,2-trifluoro-ethoxy)-thiophene. One new EC monomer including silicon is 6,6-dimethy-6,7-dihydro-5H-4,8-dioxa-2-thia-6-sila-azulene. A detailed description for the synthesis of each of the new classes of monomers is provided below. The significance of including electron withdrawing and electron adding groups into EC monomers is that the modification of the electron configuration of the material can result in a color change.

Still another aspect of the present invention is directed to EC polymer devices that include more than one different color EC polymer to enable additional colors to be provided using subtractive color mixing. In one embodiment directed to this aspect of the invention, an EC polymer device includes both a red EC polymer and a blue EC polymer whose charges have been manipulated such that portions of the EC device include overlapping red EC polymers and blue EC polymers and thereby achieve obstruction of nearly all wavelengths of light, which is interpreted visually as black.

Another aspect of the present invention is directed to incorporating a logo into an EC polymer device, such the logo is generally obscured when the EC polymer device is colored, and is substantially visible when the EC polymer device is not colored. This concept can be implemented in windows, which in a first state, substantially block light, and in a second state, substantially allow light to pass through the window while simultaneously displaying a selected textual or graphical image incorporated into the EC polymer device. Examples for an application of such logo-containing devices include aircraft windows, which in the colored state, substantially block light and in the transparent state, display a logo of the airline, and exit signs which in their colored state are substantially opaque and in their transparent (non-colored) state, display exit signage. The logo or text can be implemented by incorporating an additional transparent layer on which the logo/text is formed into an EC polymer device. A conventional computer printer can be used to print text and graphics on transparent sheets for use with overhead projectors. That technique can be used to print a logo or text onto a transparent sheet for incorporation into an EC device, such as a window.

The present invention is also directed to EC polymer devices that include a cathodic EC polymer layer, a gel electrolyte, a counter electrode, and a reference electrode. Working prototypes of such devices have included a silver-based reference electrode, which has significantly increased the speed of transition of the EC device from a colored state to a transparent state.

Yet another aspect of the present invention is directed to optimizing gel electrolytes for incorporation into EC polymer devices that include a cathodic EC polymer layer, a gel electrolyte, and a counter electrode. Empirical studies, described in detail below, indicate that a first particularly preferred gel electrolyte can be achieved using a gamma butyrolactone and propylene carbonate as solvents, lithium perchlorate as a source of ions, and polymethylmethacrylate as a structural support. Another particularly preferred gel electrolyte can be achieved using ethylene carbonate and propylene carbonate as solvents, lithium perchlorate as a source of ions, and polymethylmethacrylate as a structural support.

BRIEF DESCRIPTION OF THE DRAWING FIGURES

The foregoing aspects and many of the attendant advantages of this invention will become more readily appreciated as the same becomes better understood by reference to the following detailed description, when taken in conjunction with the accompanying drawings, wherein.

Figure 2:
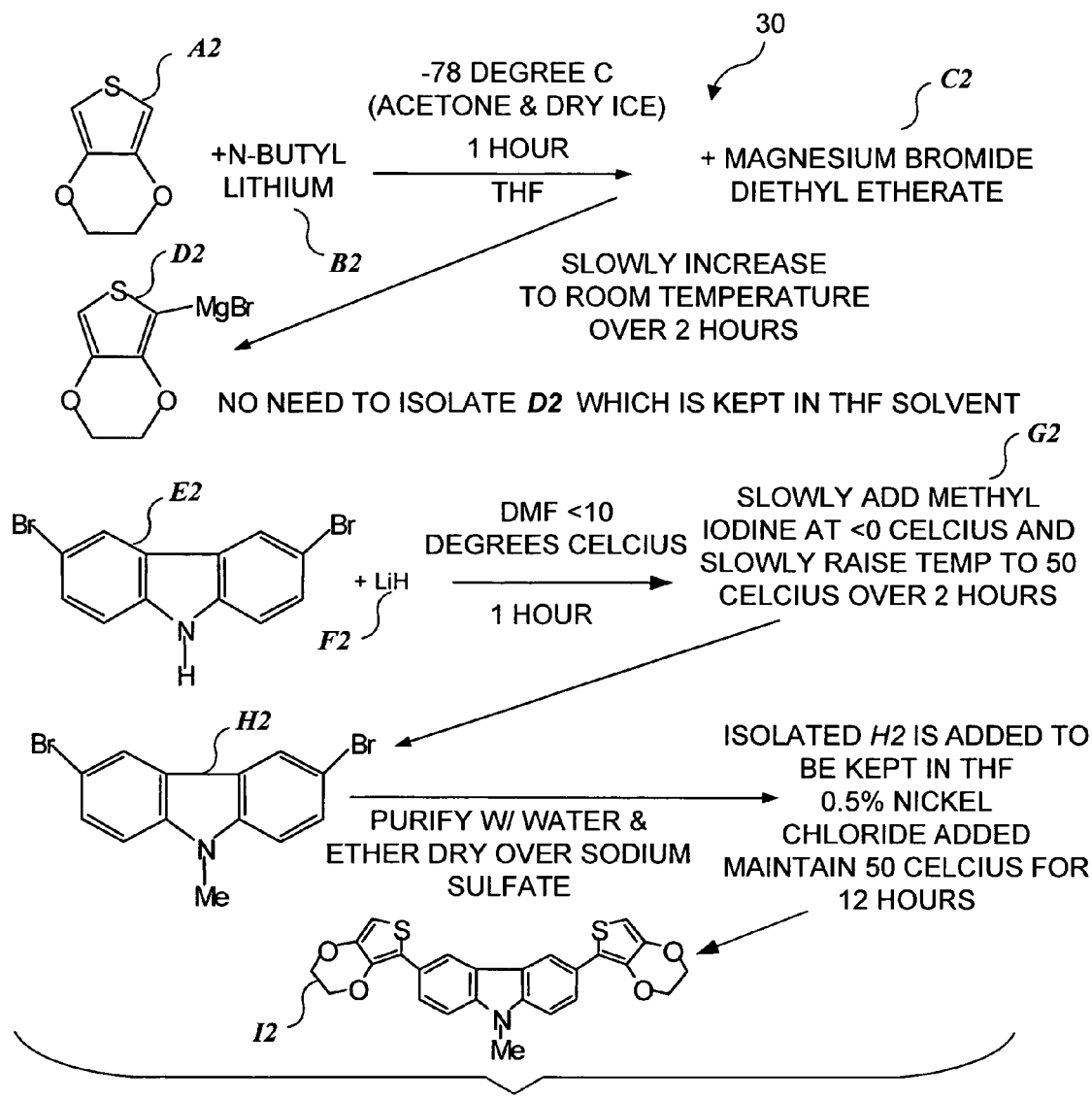
Figure 3:
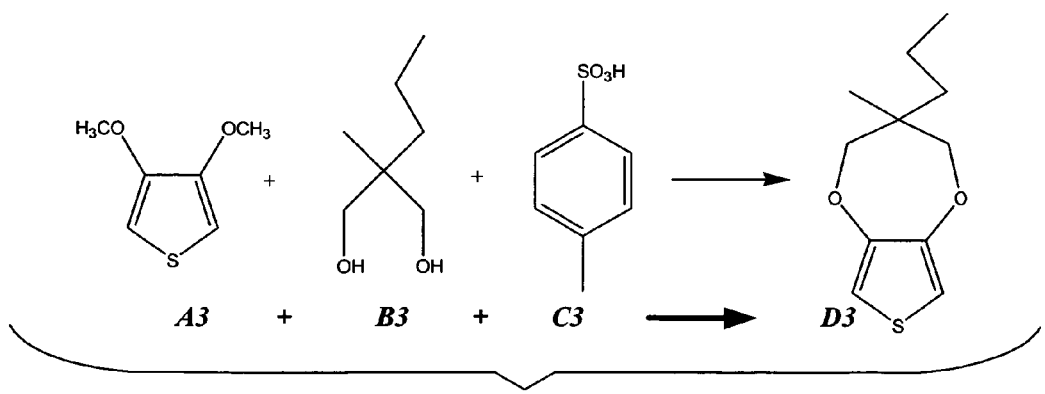
Figure 4:
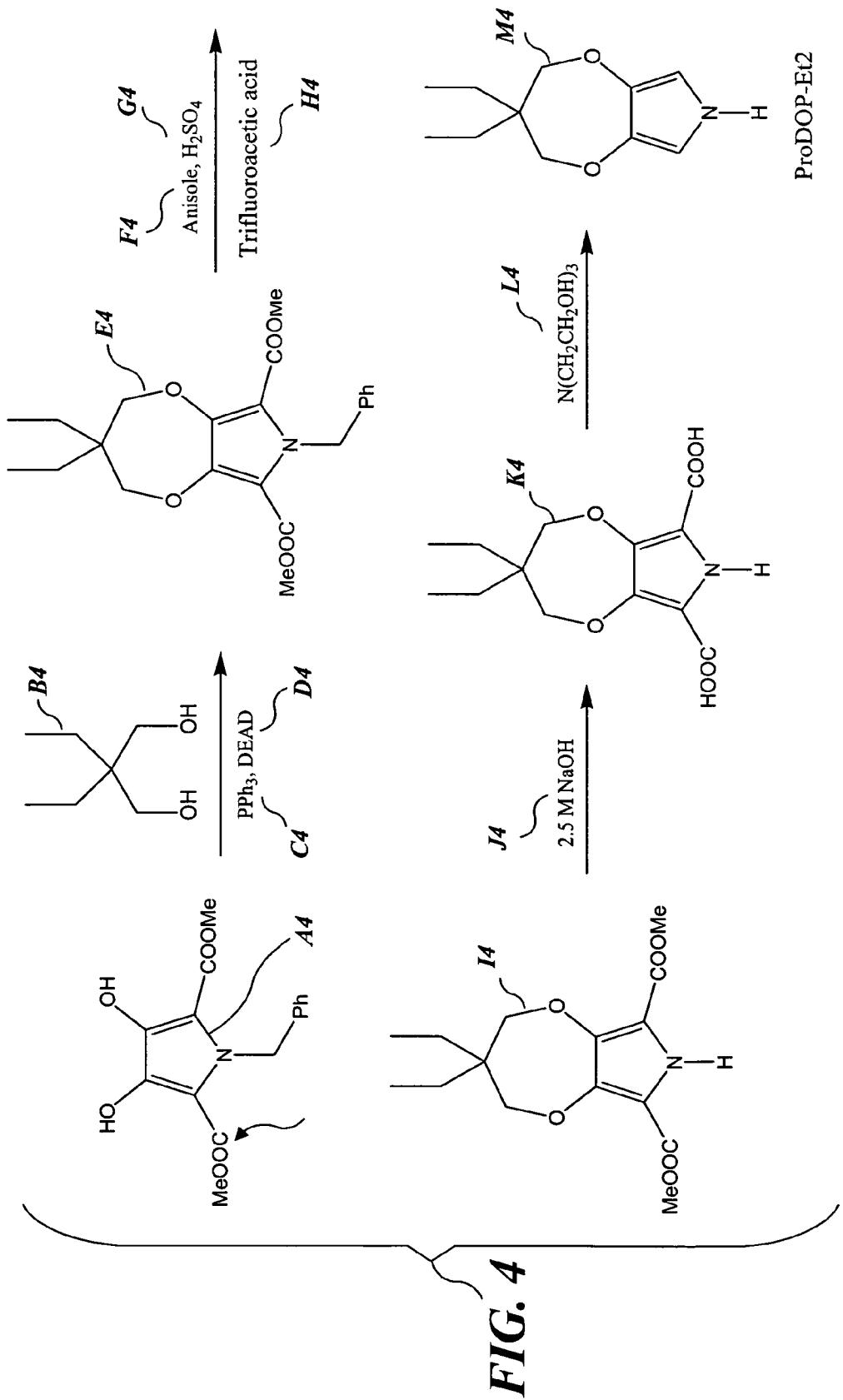
Figure 5:
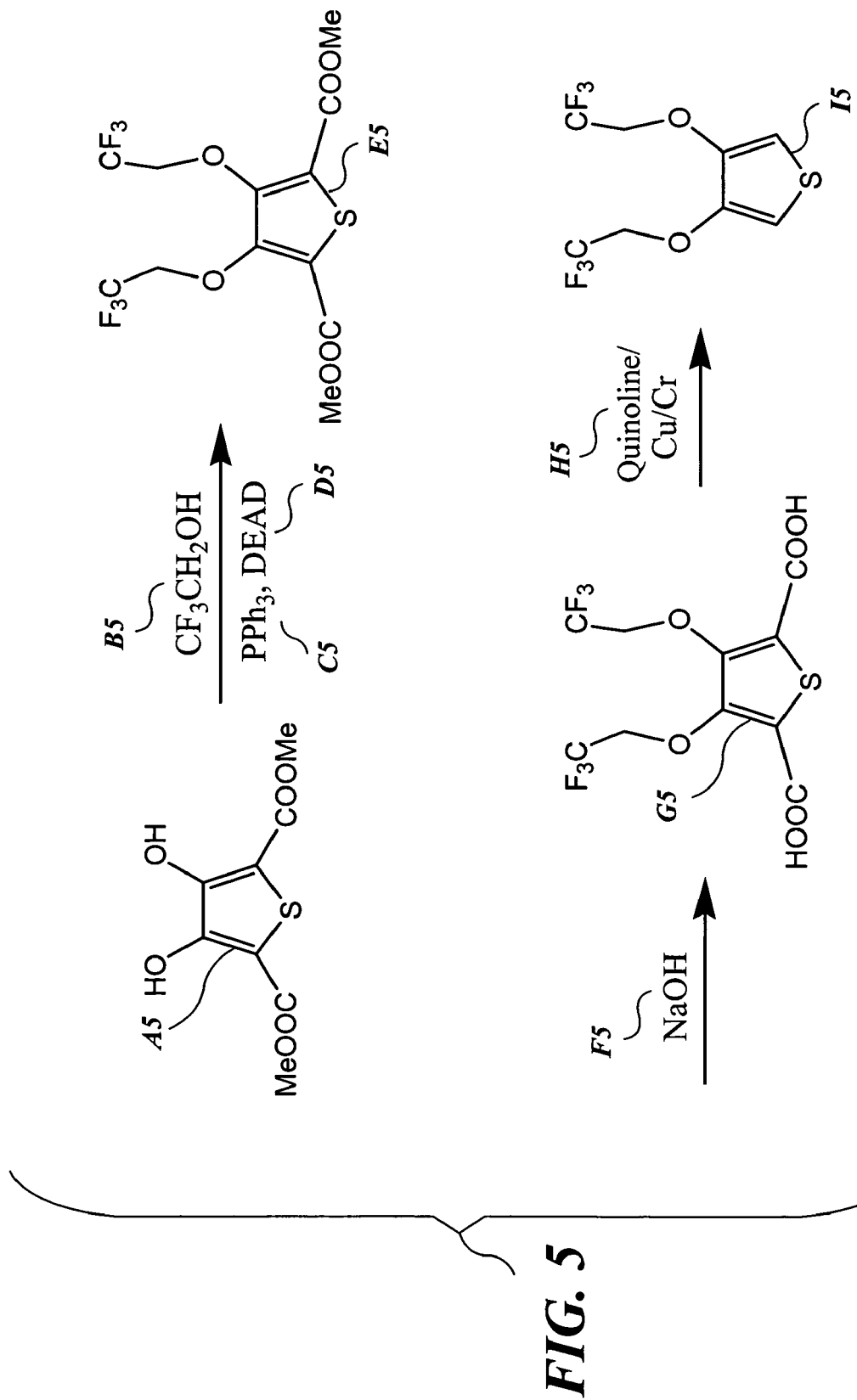
Figure 6:
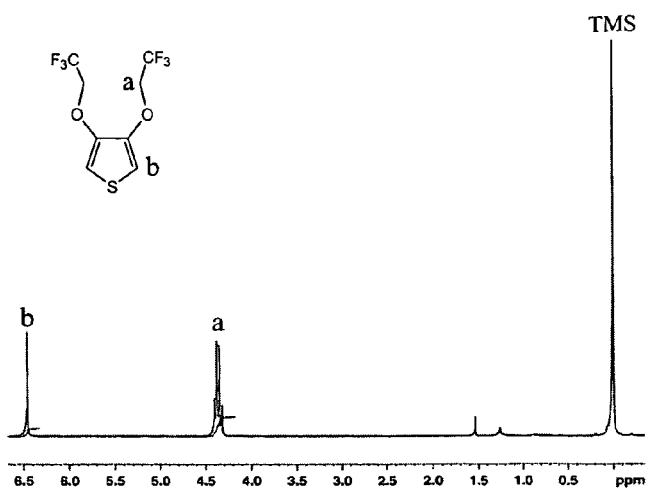
Figure 8:
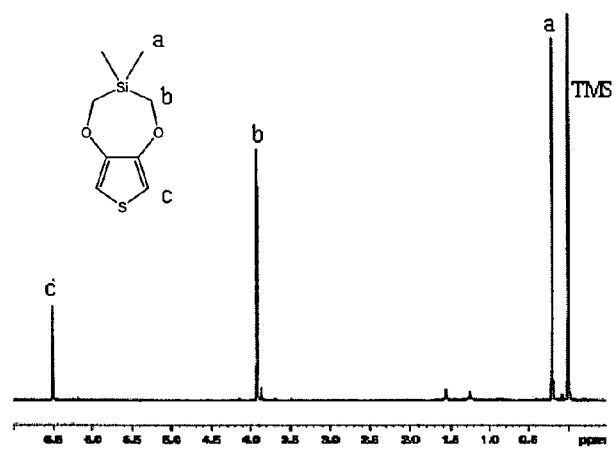
Figure 10:
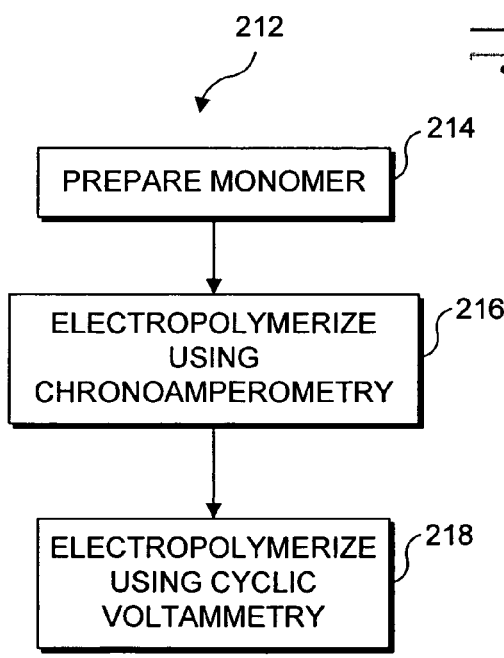
Figure 9:
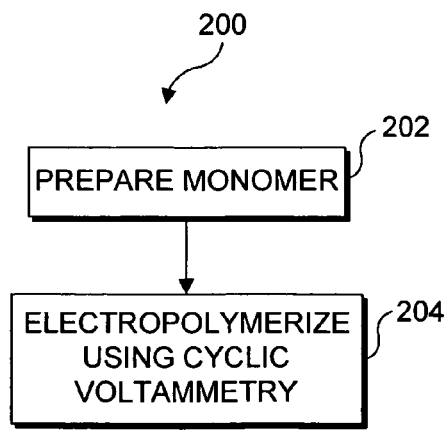
Figure 7:
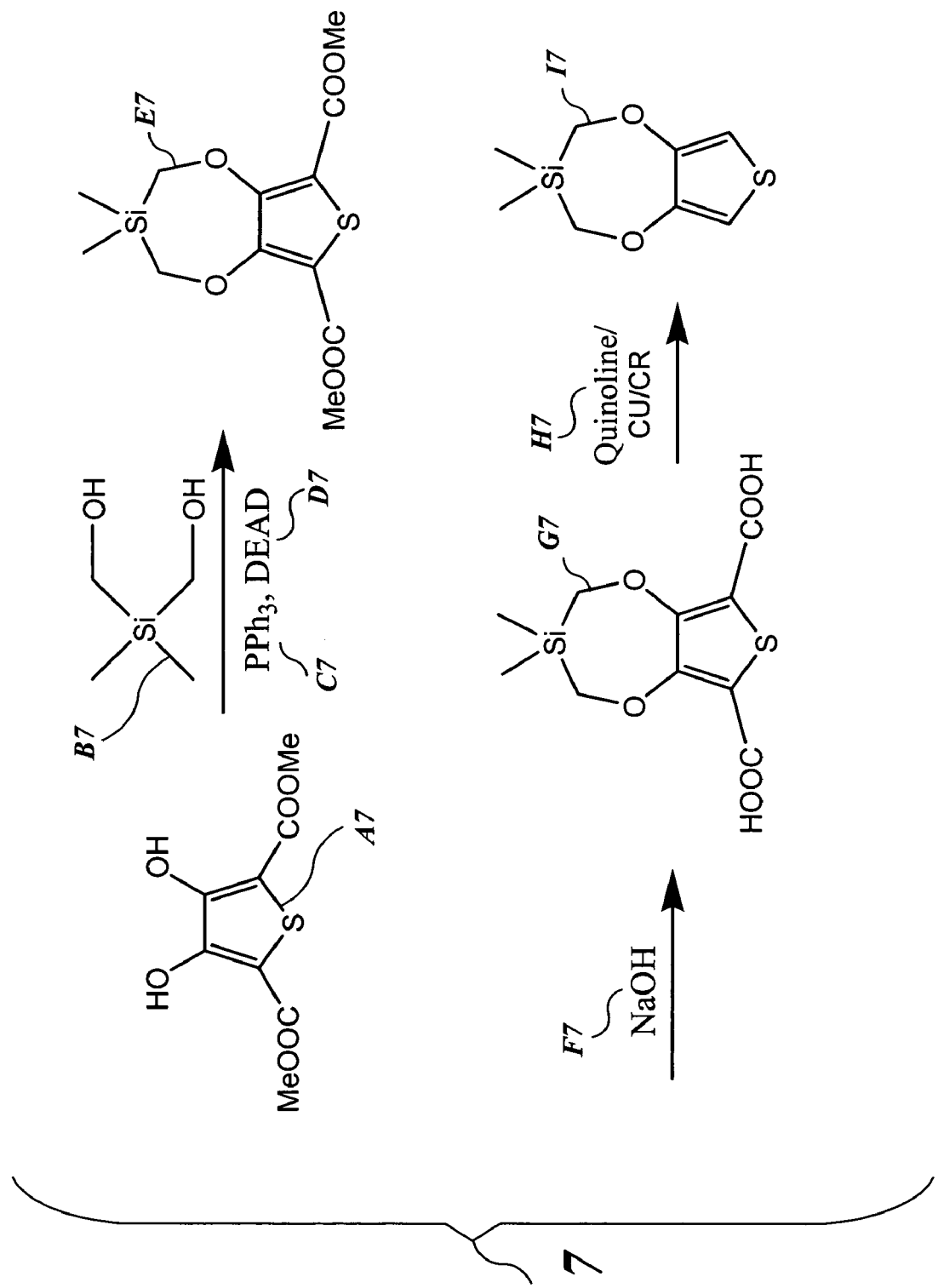
Figure 11:
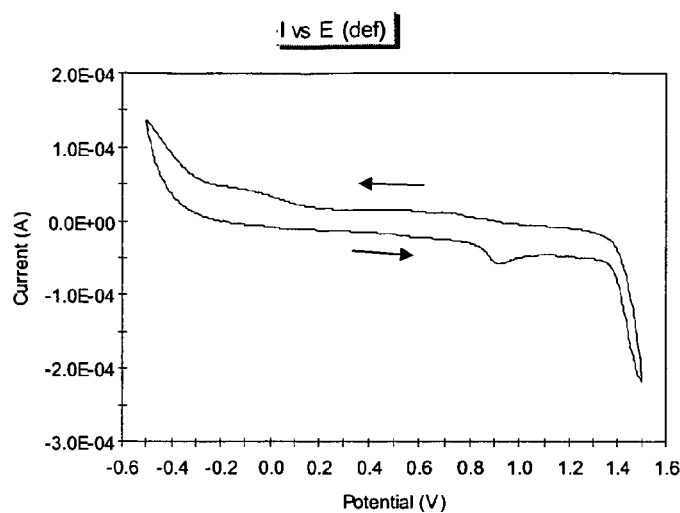
Figure 12:
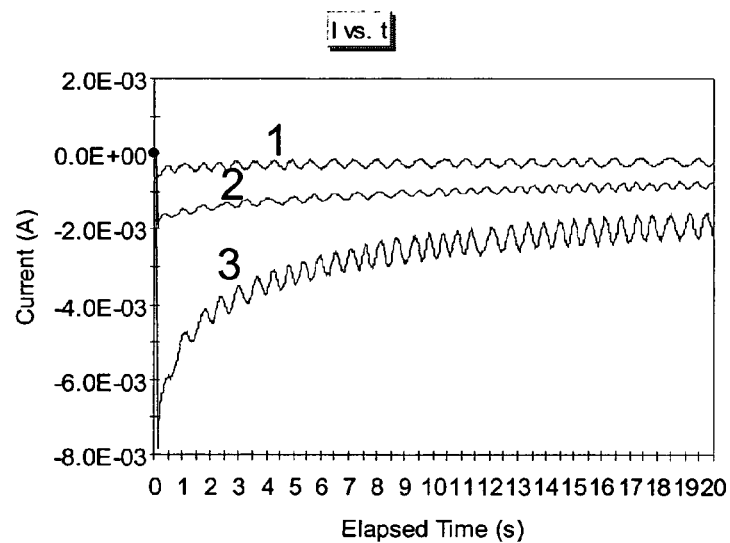
Figure 13:
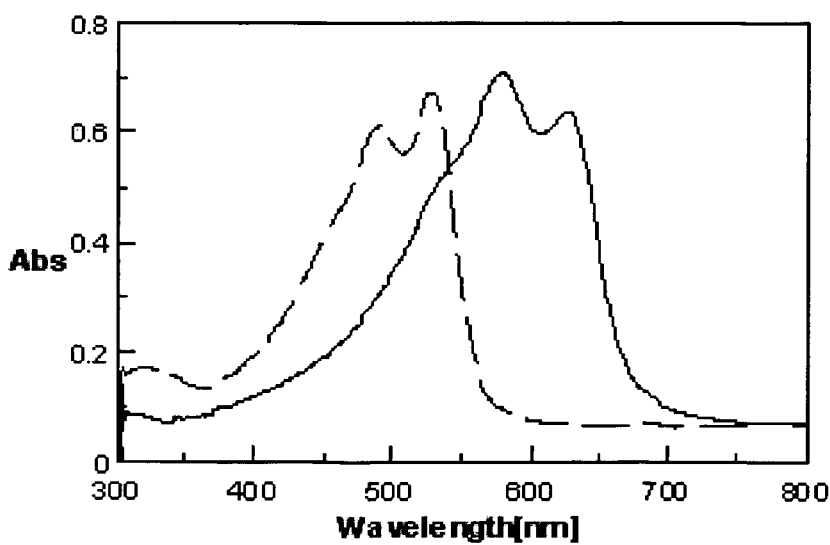
Figure 14:
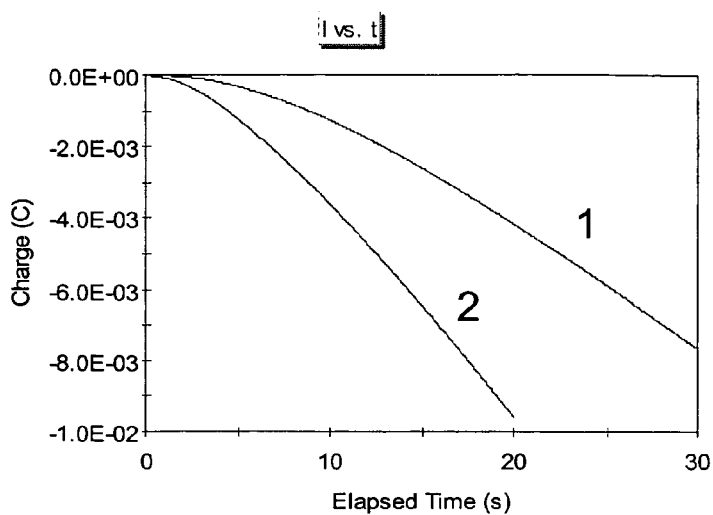
Figure 15:
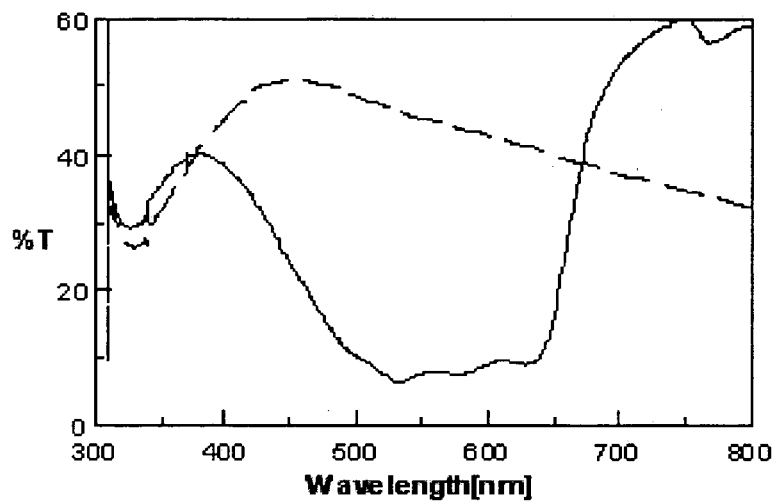
Figure 16:
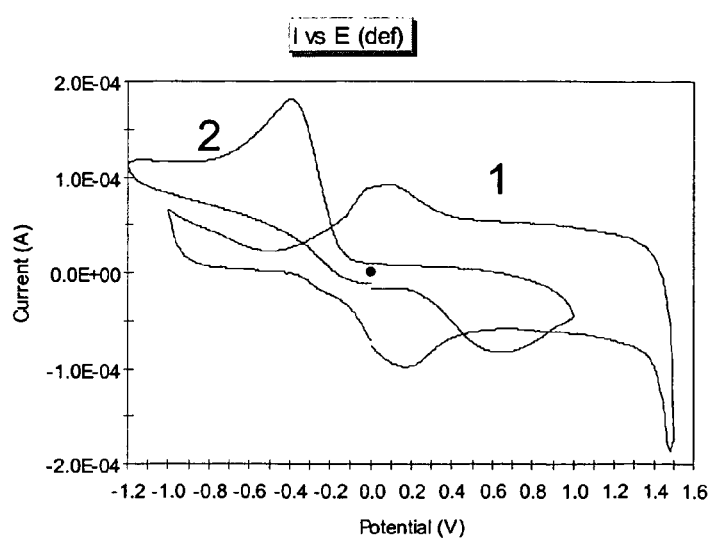
Figure 17A:
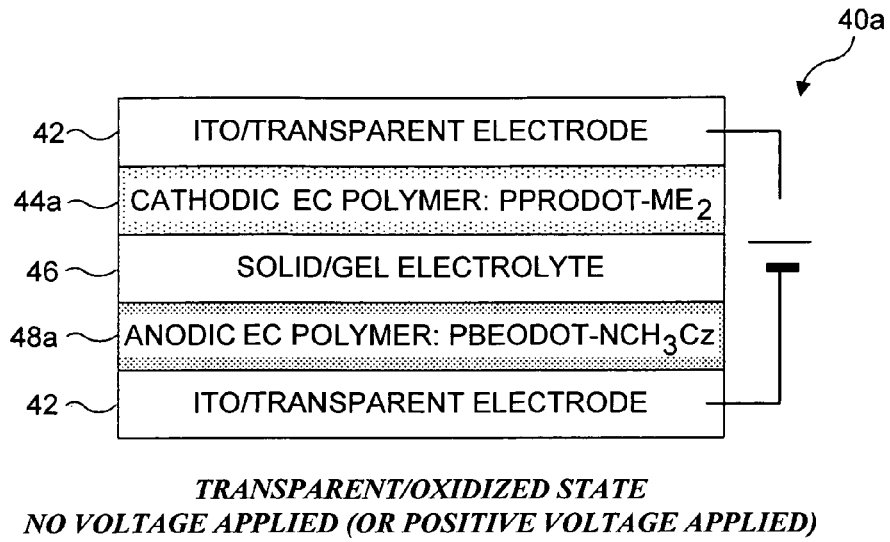
Figure 17B:
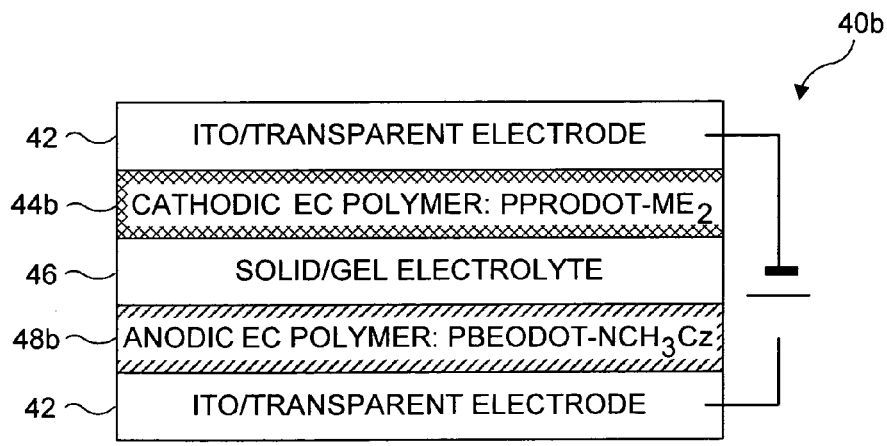
Figure 18A:
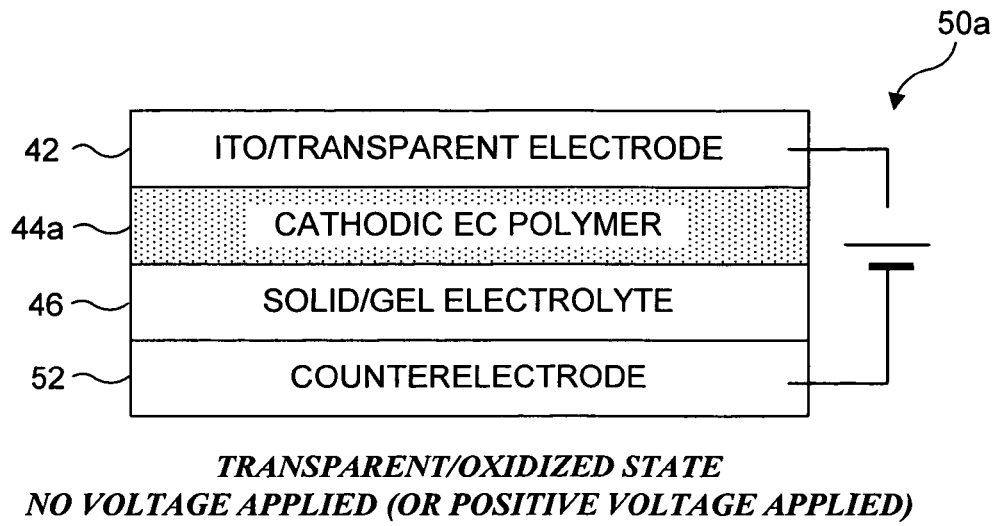
Figure 18B:
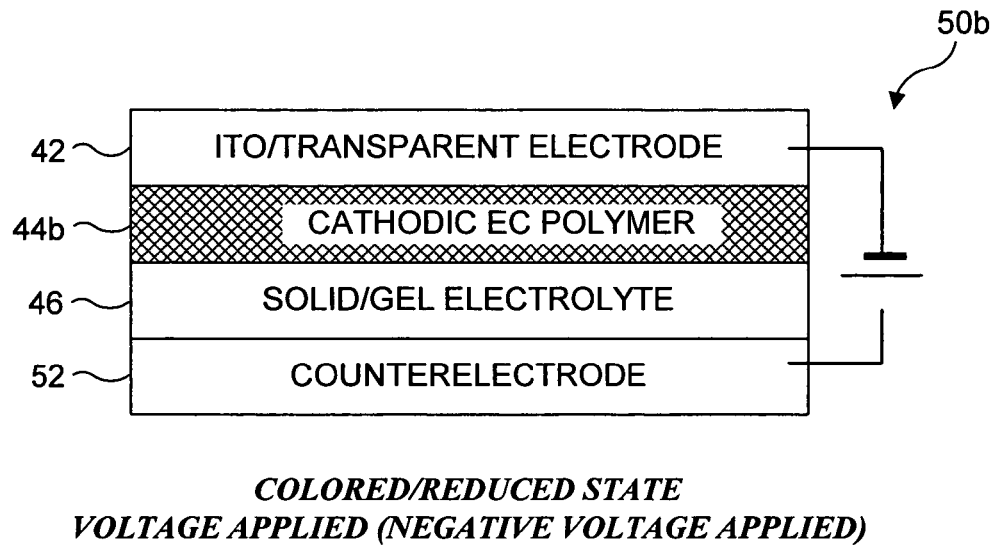
Figure 20B:
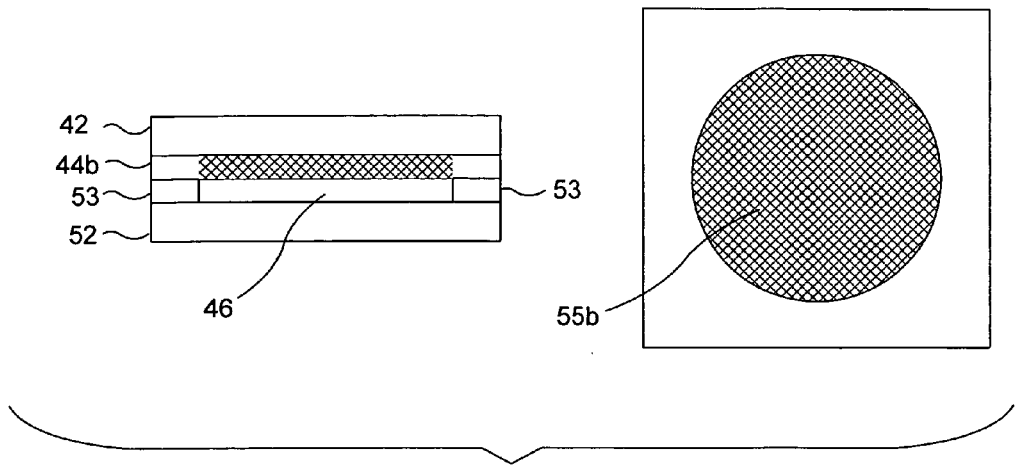
Figure 20C:
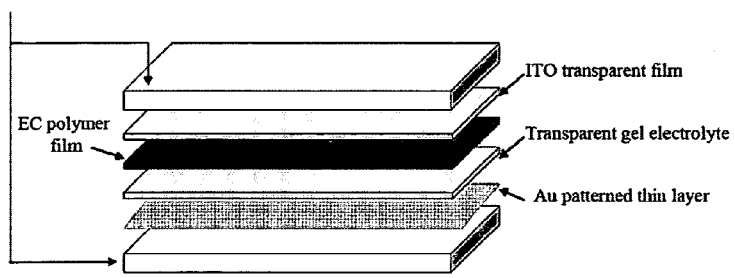
Figure 20D:
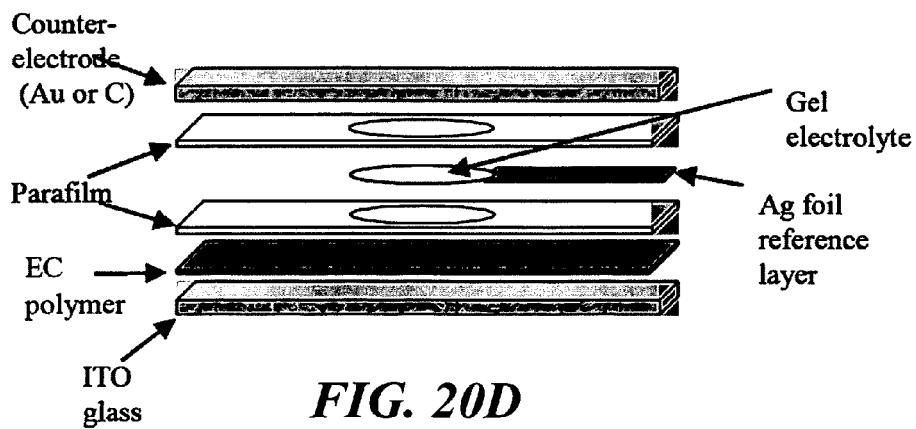
Figure 22:
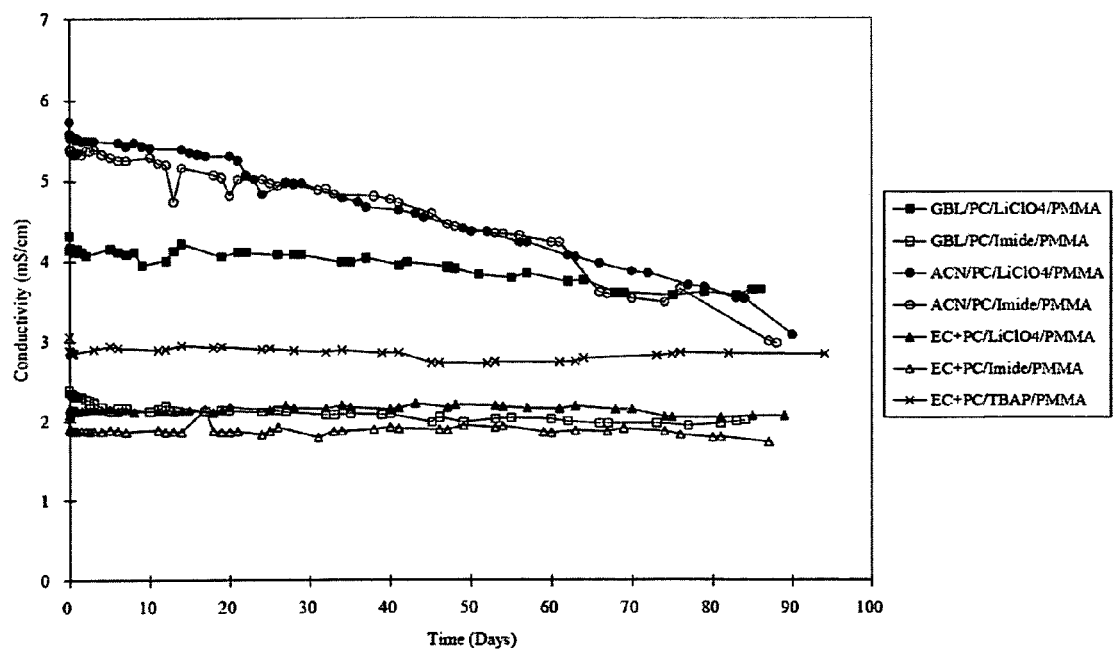
Figure 24:
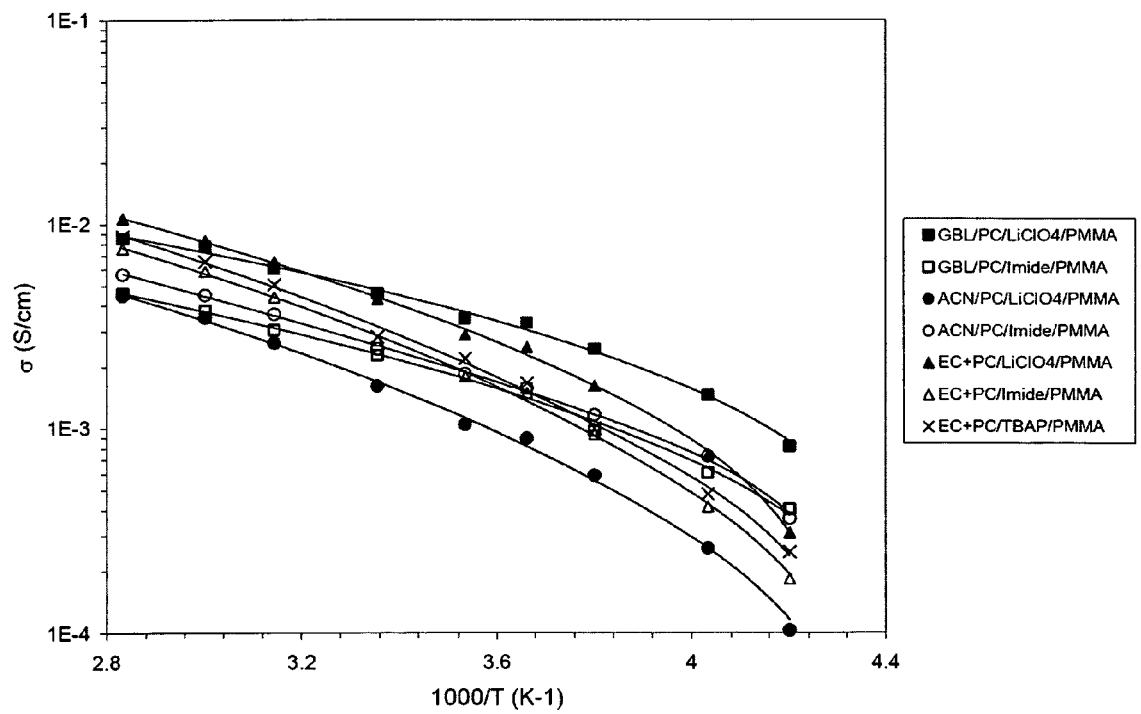
Figure 25:
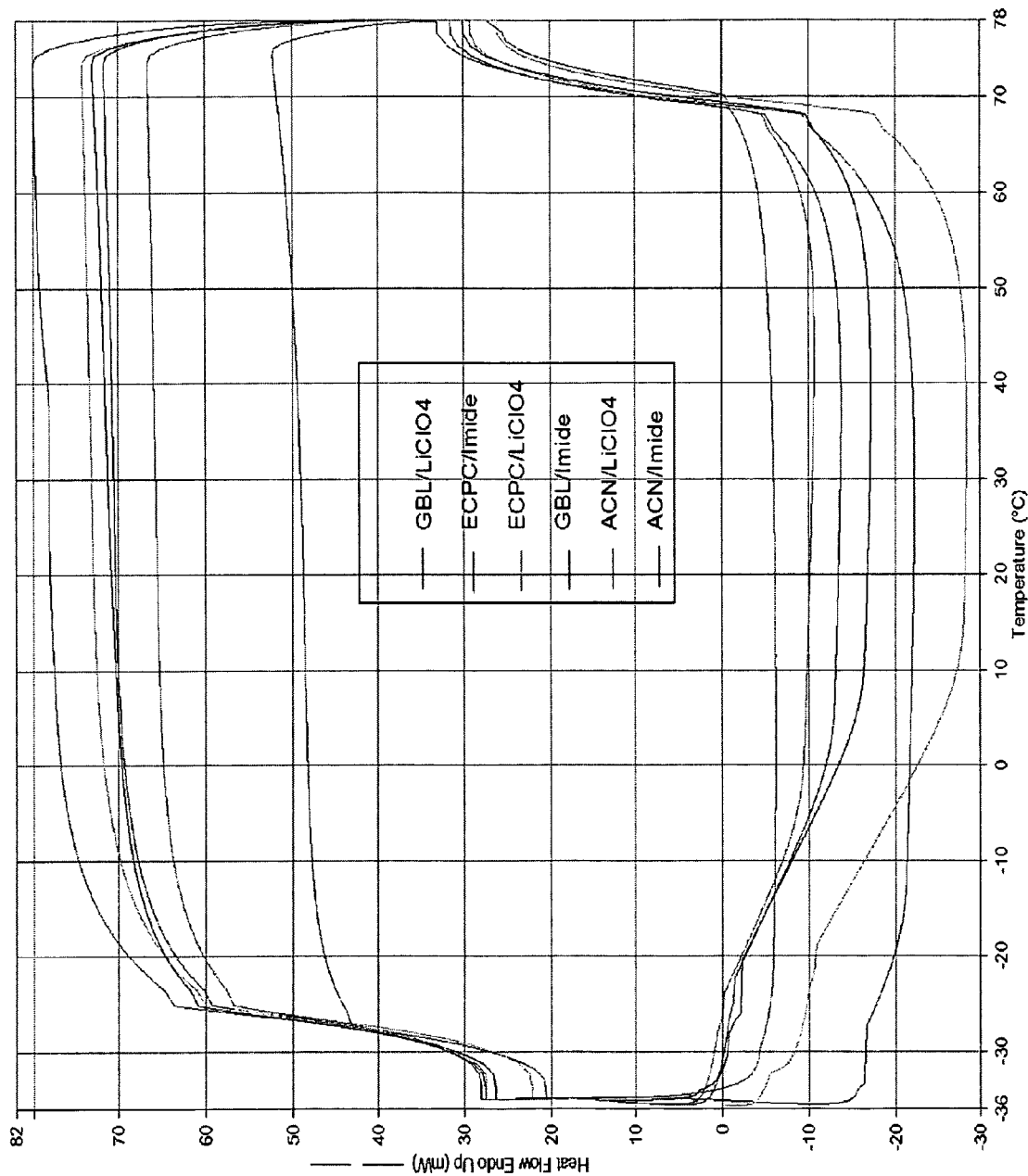
Figure 26:
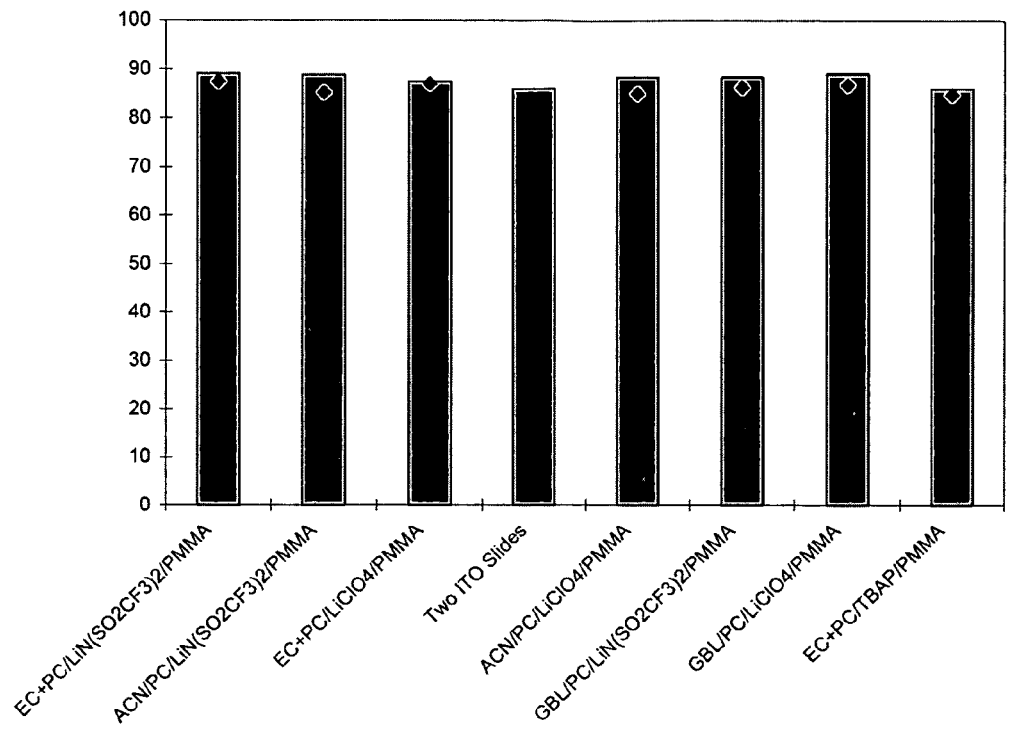
Figure 27:
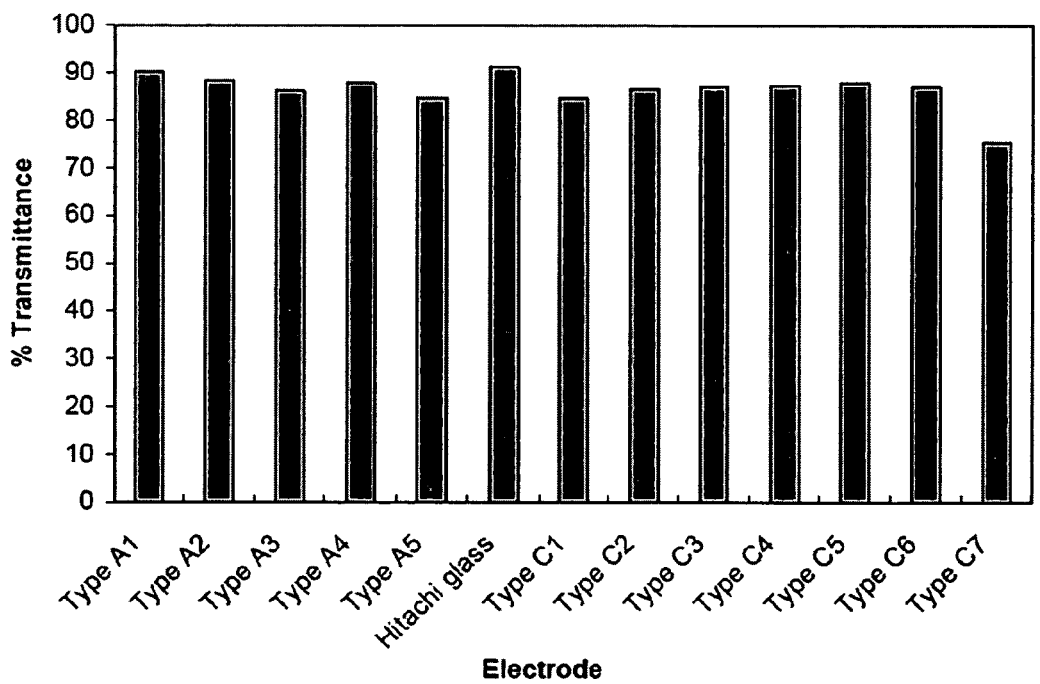
Figure 28:
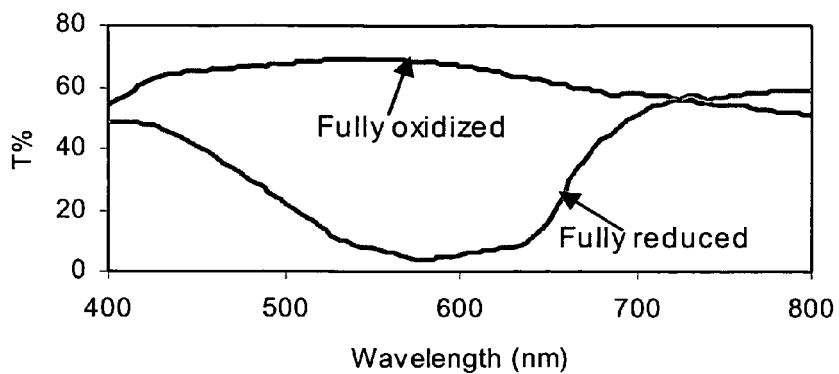
Figure 29A:
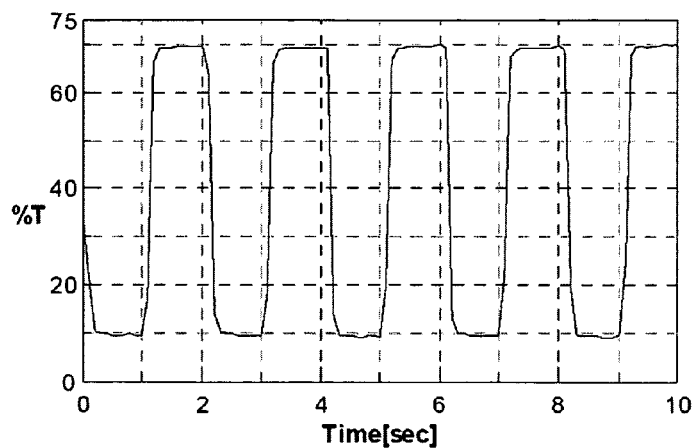
Figure 29B:
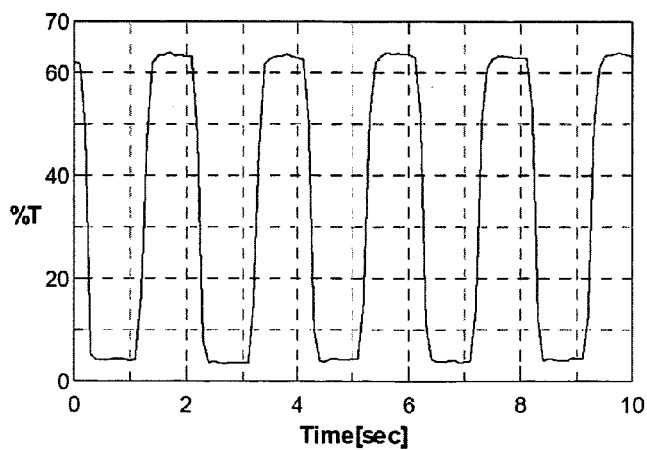
Figure 30:
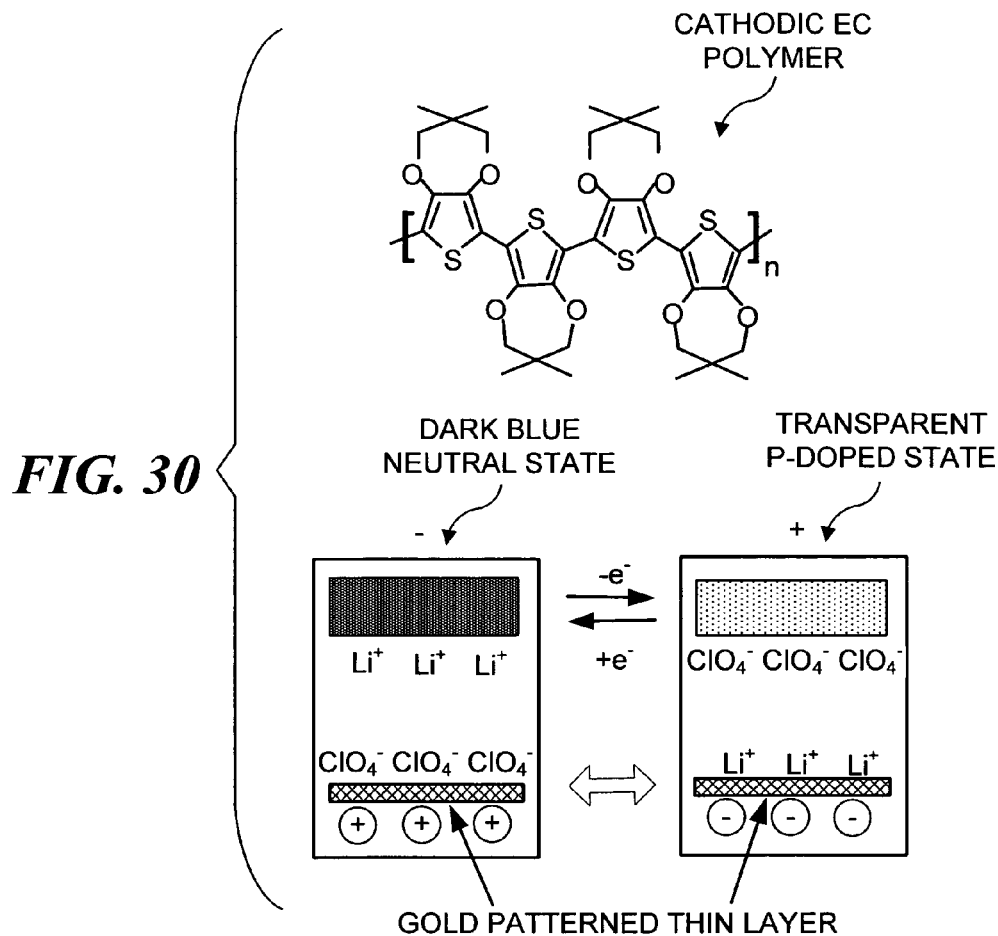
Figure 32:
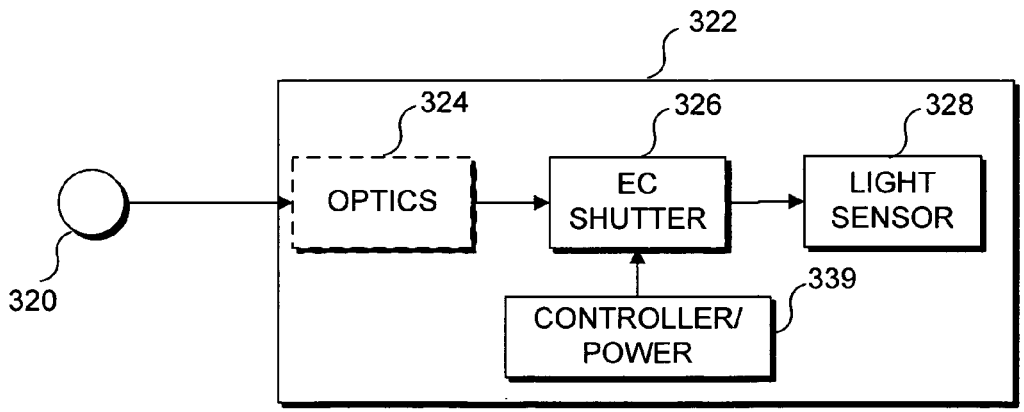
Figure 35A:
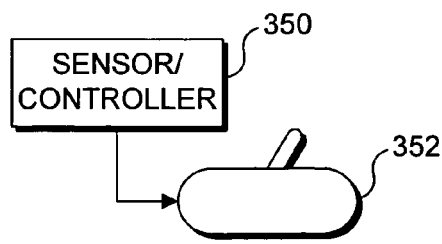
Figure 35B:
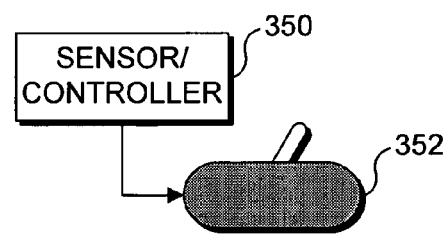
Figure 33A:
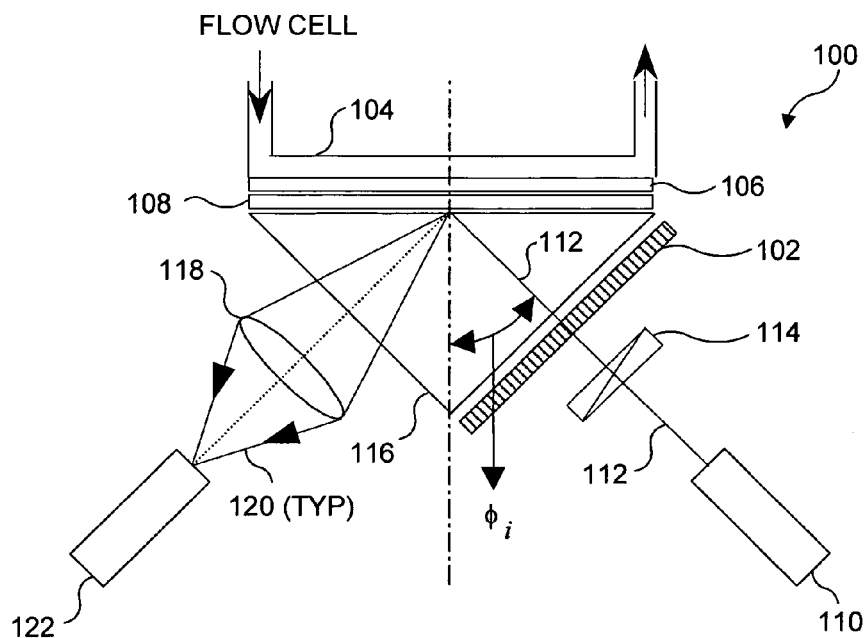
Figure 33B:
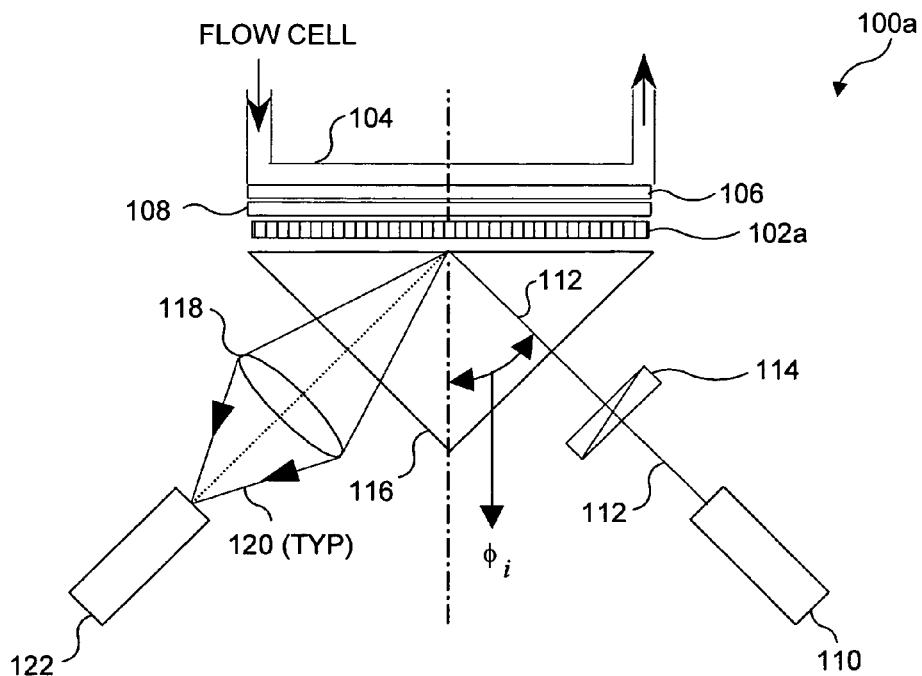
Figure 37:
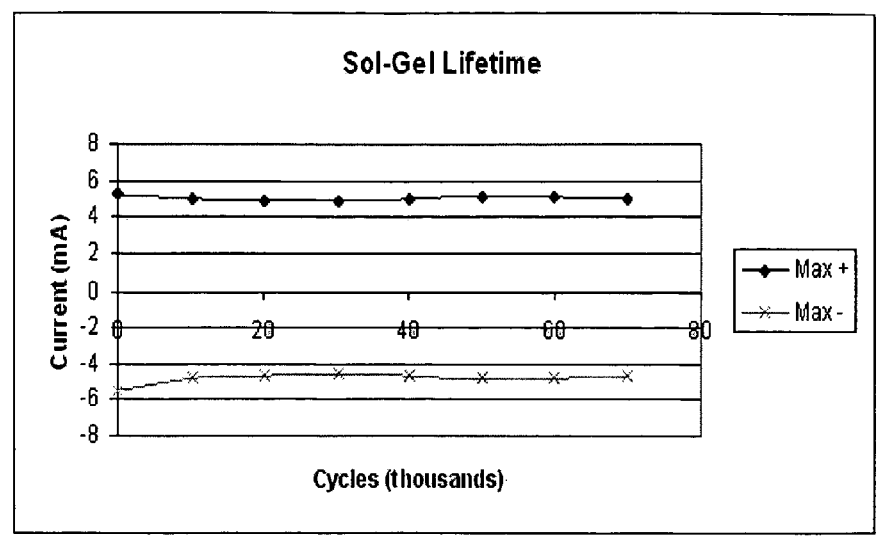
Figure 38:
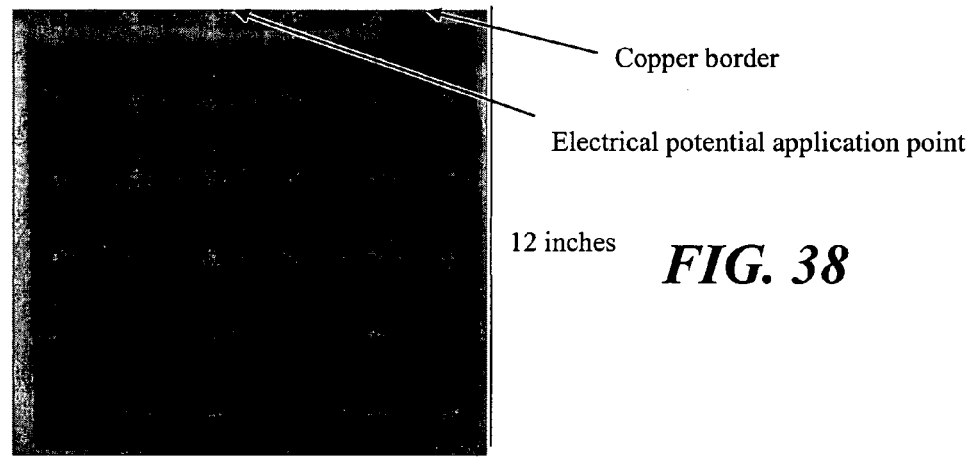
Figure 39:
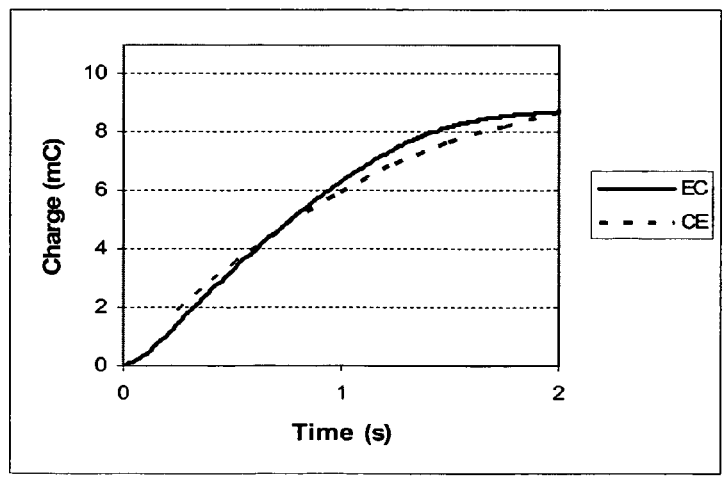
Figure 40:
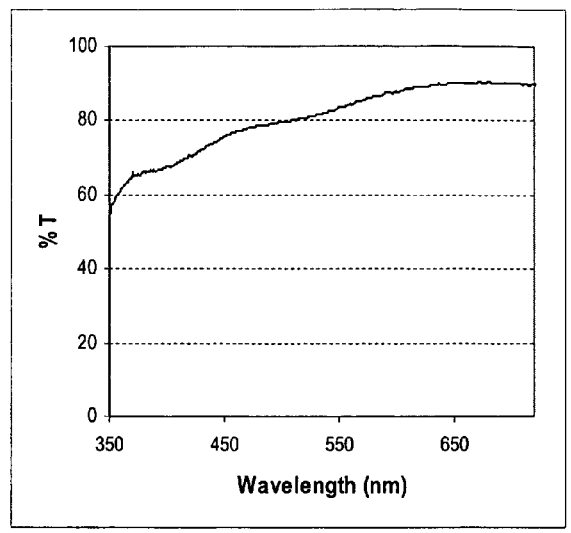
Figure 41:
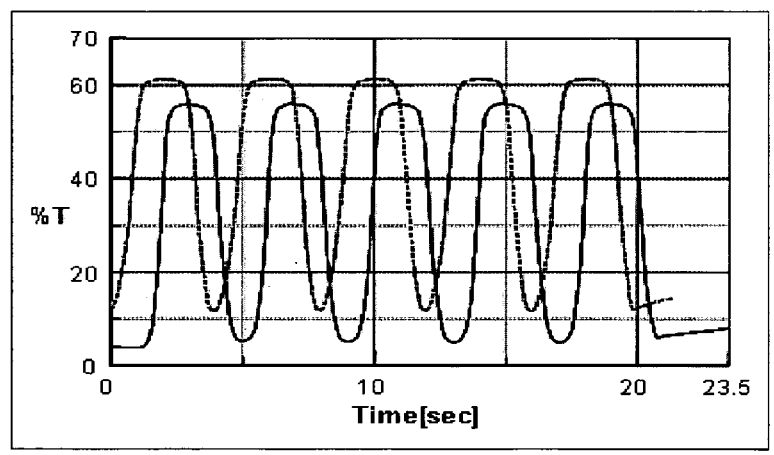
Figure 42:
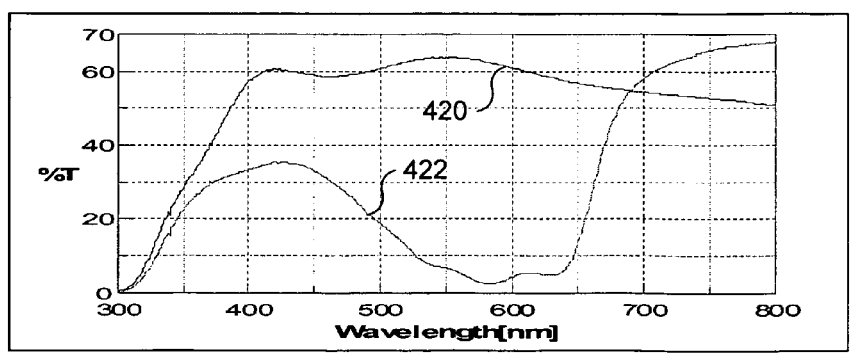

FIG. 2 schematically illustrates the synthesis of the blue monomer BEDOT-NMeCz, which may be beneficially employed as an anodic EC polymer once it has been polymerized;

FIG. 3 schematically illustrates the synthesis of the blue monomer ProDOT-MePro, which when polymerized may be beneficially employed as an EC polymer;

FIG. 4 schematically illustrates the synthesis of the red monomer ProDOP-Et2, which when polymerized may be beneficially employed as an EC polymer;

FIG. 5 schematically illustrates the synthesis of a new fluorinated EC monomer;

FIG. 6 is a graphical representation of the NMR spectrum of the fluorinated EC monomer of FIG. 5;

FIG. 7 schematically illustrates the synthesis of a new EC monomer including silicon;

FIG. 8 is a graphical representation of the NMR spectrum of the new EC monomer including silicon of FIG. 7;

FIG. 9 is a flowchart showing a sequence of logical steps executed in a first electropolymerization technique for producing EC polymer films from monomers in accord with the present invention;

FIG. 10 is a flowchart illustrating a sequence of logical steps executed in a second electropolymerization technique for producing EC polymer films from monomers in accord with the present invention;

FIG. 11 graphically illustrates the cyclical voltammetry curve of the fluorinated EC monomer of FIG. 5;

FIG. 12 graphically illustrates the chronoamperometry curve of the oxidation of the fluorinated EC monomer of FIG. 5;

FIG. 13 is a graphical representation of the UV-VIS spectrum of blue and red EC polymer films;

FIG. 14 graphically illustrates charge-time curves of the blue and red EC polymer films of FIG. 13;

FIG. 15 is a graphical representation of the UV-VIS spectrum of a combination EC device including both blue and red EC polymer films in both the reduced and oxidized states;

FIG. 16 graphically illustrates the cyclical voltammetry curves of the blue and red EC polymer films of FIG. 13;

FIGS. 17A and 17B are side elevational schematic illustrations of an EC device that includes a cathodic (PProDOT-Me$_2$) EC polymer film, an anodic (PBEDOT-NMeCz) EC polymer film, and a solid electrolyte layer;

FIGS. 18A and 18B are side elevational schematic illustrations of an EC device that includes a cathodic EC polymer film, a solid electrolyte layer and a counter-electrode;

FIG. 19A is a plan view of a gold-based counter-electrode being fashioned from a glass wafer;

FIG. 19B is a plan view of a gold-based counter-electrode;

FIG. 19C is a side elevational view of a gold-based counter-electrode;

FIGS. 19D and 19E illustrate alternative patterns that can be used to form a conductive layer on a counter-electrode;

FIG. 19F is a plan view of a graphite-based counter-electrode;

FIG. 19G is a side elevational view of a graphite-based counter-electrode;

FIG. 20A schematically illustrates a working model of a smart window including a PProDOT-Me$_2$ cathodic polymer film layer and a counter-electrode layer, to which either no voltage or a positive voltage is being applied, so that the smart window is in the oxidized or transparent state;

FIG. 20B schematically illustrates the working model of FIG. 8A, to which a negative voltage is being applied, so that the smart window is in the reduced or opaque state;

FIG. 20C schematically illustrates an EC device that includes a cathodic EC polymer film, a solid electrolyte layer, and a gold-based counter-electrode;

FIG. 20D schematically illustrates an EC device that includes a cathodic EC polymer film, a solid electrolyte layer, and a counter-electrode a reference electrode;

FIG. 20E is a photograph of an EC polymer device including a logo in a transparent state, in which the logo is clearly visible;

FIG. 20F is a photograph of an EC polymer device including a logo in a colored state, in which the logo is substantially obscured;

FIG. 21 graphically illustrates the cyclical voltammetry curve of the blue EC polymer ProDOT-Me2 initially and after 50,000 cycles;

FIG. 22 graphically illustrates the conductivity of seven electrolyte candidates over time;

FIG. 23 graphically illustrates the cyclical voltammetry curve of the blue EC polymer ProDOT-Me2 initially, after 10,000 cycles, after 25,000 cycles, and after 50,000 cycles;

FIG. 24 graphically illustrates an Arrhenius plot for seven gel electrolyte candidates;

FIG. 25 graphically illustrates the DSC stability of seven gel electrolyte candidates over an exemplary operating range;

FIG. 26 graphically illustrates transmittance data of seven gel electrolyte candidates pressed between two glass slides;

FIG. 27 graphically illustrates transmittance data for five different gold-based counter electrode configurations, seven different carbon based counter electrode configurations, and optical glass;

FIG. 28 graphically illustrates transmittance data for the EC polymer device of FIGS. 20E and 20F in the oxidized and reduced states;

FIG. 29A graphically illustrates transmittance data for a 1"×1" EC polymer device including a carbon based counter electrode;

FIG. 29B graphically illustrates transmittance data for a 1"×1" EC polymer device including a gold-based counter electrode;

FIG. 30 schematically illustrates the operation of a cathodic polymer EC layer paired with a counter-electrode layer;

FIGS. 31A-31G schematically illustrate EC polymer devices of the present invention that have been integrated into signage;

FIG. 32 schematically illustrates EC devices of the present invention integrated into a light detecting instrument that thus includes an EC polymer shutter;

FIG. 33A illustrates an embodiment in which a digital window (DW) is included in an SPR imaging system used for DNA chip reading;

FIG. 33B illustrates an embodiment in which a DW is included in a Surface Plasmon Resonance (SPR) imaging system used for DNA chip reading;

FIG. 34 is a schematic illustration of the EC polymer devices of the present invention as integrated into a conventional dual-pane architectural window;

FIGS. 35A and 35B schematically illustrate EC polymer devices of the present invention as integrated into an anti-glare rearview mirror;

FIG. 36 is a schematic illustration of an EC polymer device implementing subtractive color mixing to achieve an additional color;

FIG. 37 graphically illustrates the switching lifetime of a vanadium pentoxide gel for use as a counter electrode;

FIG. 38 is a photograph of uniform vanadium pentoxide gel for use as a counter electrode;

FIG. 39 graphically illustrates short term charge capacitance data for a 1 inch×1 inch vanadium oxide thin film;

FIG. 40 graphically illustrates transmittance data for a 1 inch×1 inch vanadium oxide thin film;

FIG. 41 graphically illustrates transmittance data for an EC polymer device including a vanadium pentoxide counter electrode over 1000,000 cycles; and FIG. 42 graphically illustrates transmittance data for an EC polymer device including a vanadium pentoxide counter electrode in both oxidized and reduced states.

DESCRIPTION OF THE PREFERRED EMBODIMENT

Overview of the Present Invention

The present invention is directed to methods for synthesizing EC polymer films having properties that can be beneficially employed in EC polymer devices, specific configurations of EC polymer-based devices, and gel electrolytes that can be beneficially employed in such EC polymer devices. More specifically, the present invention is directed to: (1) methods for preparing new monomers that can be used to produce new EC polymers; (2) methods for producing the new EC polymers from the new monomers; (3) specific configurations for EC polymer devices utilizing the new EC polymers; and (4) methods for optimizing gel electrolytes utilized in such EC polymer devices.

The terms smart window and digital window are used herein. The term smart window is intended to refer to EC polymer devices incorporated into windows for use in buildings, vehicles, and aircraft that incorporate, to enable the transmissive properties of the window to be selectively varied. For example, a smart window can be changed from a first substantially transparent state to a second substantially opaque state. The term digital window is intended to refer to EC polymer devices incorporated into pixelated displays or windows in individual pixels are selectively controllable.

Synthesis of ProDOT-Me$_2$ Blue EC Monomer

Figures 1A, 1B:
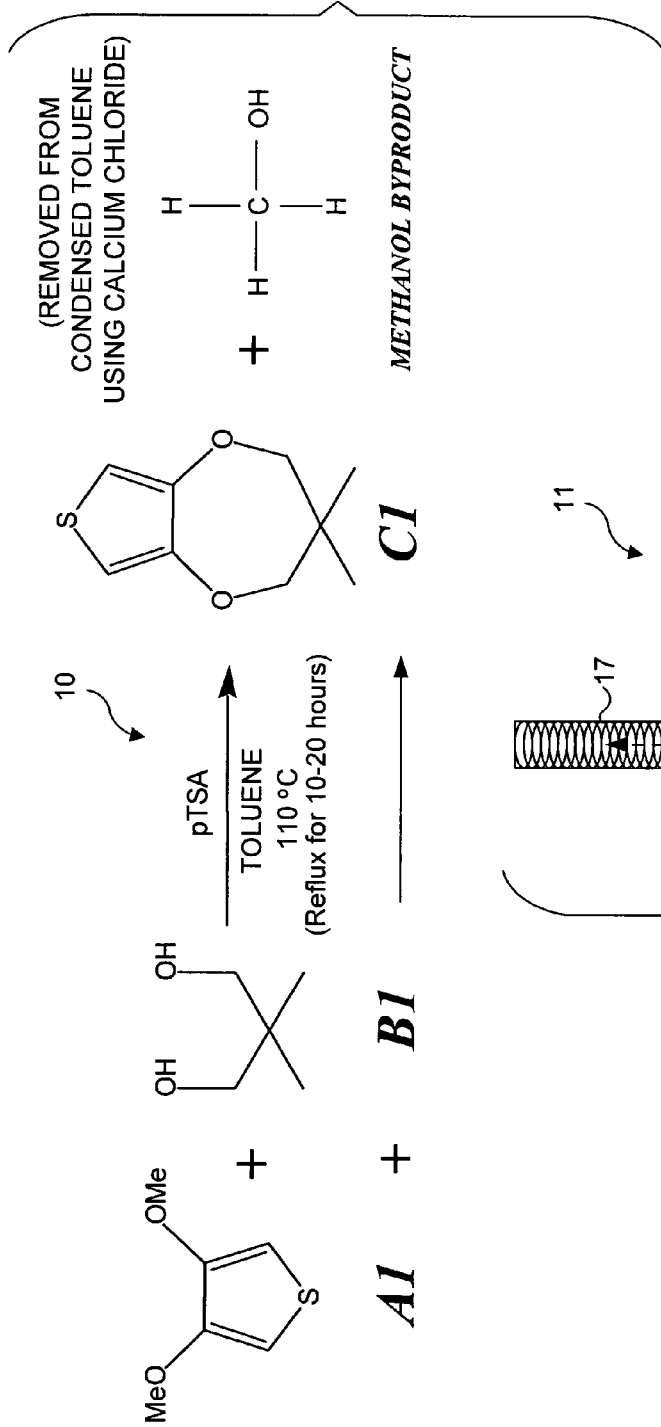
FIG. 1A is a schematic illustration of the synthesis of the blue monomer ProDOT-Me$_2$, which when polymerized, may be beneficially employed as a cathodic EC polymer.
FIG. 1B is a schematic illustration of apparatus used in the synthesis of FIG. 1A.

A first blue organic polymer expected to be useful in EC devices is poly[3,3-dimethyl-3,4-dihydro-2H-thieno[3,4-b][1,4]dioxepine], also known as dimethyl substituted poly(3,4-propylenedioxythiophene), or PProDOT-Me$_2$. FIG. 1A illustrates a preferred transetherification reaction 10 for the preparation of ProDOT-Me$_2$ (labeled C1 in FIG. 1A), the monomer that can be polymerized to achieve PProDOT-Me$_2$. A desired quantity of 3,4-dimethoxythiophene (labeled A1 in FIG. 1A) and 2,2-dimethyl-1,3-propanediol (labeled B1 in FIG. 1A) are dissolved in toluene and heated in the presence of p-toluenesulfonic acid monohydrate (at a concentration of 1.5 mol % of 3,4-dimethoxythiophene) for 10-20 hours at a temperature of 110° C. This process is referred to in the chemical arts as refluxing, because toluene boils at a temperature of 110° C. In a refluxing process, a solution is boiled until a fraction of the solution (in this case, only the toluene fraction—since the 3,4-dimethoxythiophene, the 2,2-dimethyl-1,3-propanediol and the p-toluenesulfonic acid monohydrate fractions each have higher boiling points) is driven out of the solution as a vapor, and those vapors are then condensed and returned to the original solution.

The purpose of employing refluxing in the present invention is because methanol is produced as an undesirable byproduct when 3,4-dimethoxythiophene and 2,2-dimethyl-1,3-propanediol combine to form the desired product. Once some of the 3,4-dimethoxythiophene and 2,2-dimethyl-1,3-propanediol combine to form the desired product, the presence of the methanol byproduct actually inhibits further reaction between the 3,4-dimethoxythiophene and 2,2-dimethyl-1,3-propanediol. Thus, to increase the amount of desired product that can be produced, the methanol byproduct is preferably removed as it is generated. Refluxing enables the methanol byproduct to be continually removed. Both methanol and toluene have boiling points that are lower than the boiling points of the other fractions, i.e., 3,4-dimethoxythiophene, 2,2-dimethyl-1,3-propanediol, p-toluenesulfonic acid monohydrate, and the desired product. By heating the toluene to boiling, both the methanol and toluene are removed from the solution. The removed toluene and methanol are condensed and collected in a separate container. Calcium chloride is added to that separate container, which reacts with the methanol to enable the methanol to be removed from the toluene. The condensed toluene is then returned to the original solution (the boiling 3,4-dimethoxythiophene, 2,2-dimethyl-1,3-propanediol, p-toluenesulfonic acid monohydrate, toluene, and the desired product). A preferable step in the synthesis is thus removing the methanol using calcium chloride. As those of ordinary skill in the art will recognize, such a "salting out" process is sometimes employed in organic synthesis to remove undesirable reactants. In one embodiment, the condensed methanol and condensed toluene are filtered through solid calcium chloride. The resulting monomer, ProDOT-Me$_2$, is readily polymerized to PProDOT-Me$_2$. In the bleached state (when no voltage or a positive voltage is applied), PProDOT-Me$_2$ has a light blue tint, while in the opaque state (when a negative voltage is applied) PProDOT-Me$_2$ achieves a dark blue tint.

FIG. 1B schematically illustrates an apparatus 11 used to perform the above synthesis. The reactants (3,4-dimethoxythiophene, 2,2-dimethyl-1,3-propanediol, and p-toluenesulfonic acid monohydrate) are dissolved in toluene in a container 13. Sufficient heat is applied to container 13 (as noted above the boiling point of toluene is 110° C., and while the reagents added to the toluene will somewhat affect the boiling point of the solution, the boiling point of the solution will still be substantially 110° C.) so that the solution within the container gently boils. Toluene vapor (and any methanol byproduct) will be driven out of container 13 and into boiling tube 15. The vapors will rise into condenser 17, where the vapors condense to a liquid that flows into packed calcium chloride 19. The movement of the vapors is indicated by a dashed line, while the movement of the condensed vapors (i.e., the liquid) is indicated by solid lines. The methanol is absorbed by the calcium chloride, and the condensed toluene rises to a level 21, where the condensed toluene returns back to container 13 via boiling tube 15. Preferably the amount of toluene employed, and the internal volume of apparatus 11 is selected such that some toluene always remains within container 13 (i.e., the toluene in the solution never completely boils away) and so that the condensed toluene is able to rise through the packed calcium chloride to level 21, to ensure that some condensed toluene returns to container 13. Preferably a nitrogen blanket is introduced into apparatus 11, so that ambient oxygen does not introduce undesired byproducts or cross reactions.

Synthesis of BEDOT-NMeCz Blue EC Monomer

A second blue organic polymer expected to be useful in EC devices is poly[3,6-bis(2-(3,4ethylenedioxythiophene))-N-methylcarbazole], also known as PBEDOT-NMeCz. A preferred synthesis scheme 30 is shown in FIG. 2. First, 3,4-ethylenedioxythiophene (EDOT; labeled A2 in FIG. 2) is treated with n-Butyl lithium (labeled B2 in FIG. 2) in a solution of tetrahydrofuran (THF) at −78° C. for one hour. Those of ordinary skill in the art will recognize this step as being employed in the preparation of a Grignard reagent. The resulting Grignard reagent is then treated with magnesium bromide diethyl etherate (labeled C2 in FIG. 2). The product (labeled D2 in FIG. 2) remains in the THF solvent.

Next, a derivatized dibromocarbazole (labeled E2 in FIG. 2) is combined with lithium hydride (labeled F2 in FIG. 2) in dimethyl foramide (DMF) and kept at less than 10° C. for an hour. Methyl groups are slowly added at a 1:1 ratio (as indicated by G2 in FIG. 2), and the temperature is raised to 50° C. over a two hour period, yielding a methylated derivatized dibromocarbazole product (labeled H2 in FIG. 2), which is purified by washing with water and ether and dried over sodium sulfate. Preferably, methyl iodine (MeI) is used as a methylating agent. Reagents D2 and H2 are combined, resulting in the EDOT rings being affixed to the derivatized dibromocarbazole. The reaction between D2 and H2 is facilitated with a nickel catalyst and requires that the reagents be held together at 50° C. over a twelve hour period, to yield BEDOT-NMeCz (labeled I2 in FIG. 2). The BEDOT-NMeCz monomer may then be polymerized to obtain the PBEDOT-NMeCz polymer to be used as an anodic layer in an EC device.

Synthesis of ProDOT-MePro Blue EC Monomer

A third blue organic polymer expected to be useful in EC devices is poly[3-methyl-3-propyl-3,4-dihydro-2H-thieno[3,4-b][1,4]dioxepine], also known as PProDOT-MePro. A preferred synthesis scheme to obtain the monomer for this polymer, ProDOT-MePro, is shown in FIG. 3. A desired quantity of 3,4-dimethoxythiophene (labeled A3 in FIG. 3) and 2-methyl-3-propyl-1,3-propanediol (labeled B3 in FIG. 3) are dissolved in toluene and heated in the presence of p-toluenesulfonic acid monohydrate (labeled C3 in FIG. 3) and refluxed for 10-20 hours, generally as described above in conjunction with FIGS. 1A and 1B. Preferably, the refluxing occurs under an inert atmosphere. After cooling, the reaction mixture is poured through a silica gel column and eluded by hexane and dichloromethane (1:1, volume ratio), yielding the ProDOT-MePro monomer product (labeled D3 in FIG. 3).

Those of ordinary skill in the art will recognize that this synthesis reaction is based on a double Williamson etherification. A good yield of the product was obtained by this method. The double Williamson etherification has been used to synthesize symmetric 3,4-dialkyldioxylthiophene derivatives. Significantly, the ProDOT-MePro monomer synthesized in accord with the present invention has an asymmetric structure. The ProDOT-MePro monomer may then be polymerized to obtain the blue PProDOT-MePro polymer, which can then be incorporated into an EC polymer device, such as those described in detail below.

A product yield of 74% was produced using the following reaction parameters: 0.13 g (0.90 mmol) of 3,4-dimethoxythiophene; 0.18 g (1.35 mmol) of 2-methyl-3-propyl-1,3-propanediol; 78 mg (0.45 mmol) of anhydrous p-toluenesulfonic acid; and 10 ml of toluene. An Argon reflux for 19 hours generated 0.16 g of oil (the monomer product), equating to the product yield of 74%.

Synthesis of ProDOP-Et2 Red EC Monomer

One red organic polymer expected to be useful in EC devices is poly[3,3-diethyl-3,4-dihydro-2H,7H-(1,4)dioxepino(2,3-c)pyrrole], also known as poly[6,6-diethy-6,7-dihydro-2H,5H-4,8-dioxa-2-aza-azulene], and PProDOP-Et2. A preferred synthesis for the monomer required, 6,6-Diethyl-6,7-dihydro-2H,5H-4,8-dioxa-2-aza-azulene (also known as ProDOP-Et2), is shown in FIG. 4. The yield of each step in the synthesis shown in FIG. 4 is good (54% to 92%). Prior art methods generally use dibromides and disulfonate as starting materials, which results in lower yields than are obtained in the present method. The present method further differs from prior art techniques in that the first step employs a double Mitsunobu reaction, and the EC monomer achieved at the end of the synthesis is new. The new monomer, ProDOP-Et2, can be electrochemically polymerized in non-aqueous electrolyte solution. The resulting film is a pinkish red color. The film can be switched between colored and transparent states repeatedly, resulting in a high contrast ratio.

In the present method, 1-Benzyl-3,4-dihydroxy-1H-pyrrole-2,5-dicarboxylic acid dimethyl ester, the pyrrole derivative labeled A4 in FIG. 4 (hereinafter referred to as compound A4) is first synthesized from commercially available chemicals according to prior art techniques (see A. Merz, R. Schropp, E. Dotterl, "3,4-Dialkoxypyrroles and 2,3,7,8,12,13,17,18-Octaalkoxyporphyrins", Synthesis, 7, pp. 795-800, (1995)). Then, a solution of compound A4, 2,2-diethyl-1,3-propanediol (labeled B4 in FIG. 4), triphenylphosphine ($PPh_3$; labeled C4 in FIG. 4), and diethyl azodicarboxylate (DEAD; labeled D4 in FIG. 4) is refluxed in tetrahydrofuran (THF) for about 10-20 hours (preferably under an inert atmosphere). The reaction mixture is then quenched using a small amount of water, mixed with silica gel, and evaporated to dryness. The resulting material is loaded into a silica gel column and eluded by hexane and dichloromethane (1:1 volume ratio) to yield 2-Benzyl-6,6-diethyl-6,7-dihydro-2H,5H-4,8-dioxa-2-aza-azulene-1,3-dicarboxylic acid dimethyl ester, the pyrrole derivative labeled E4 in FIG. 4 (hereinafter referred to as compound E4).

A yield of 64% for compound E4 was obtained using the following reaction parameters: 5.00 g, (16.38 mmol) of compound A4, 2.165 g (16.38 mmol) of 2,2-diethyl-1,3-propanediol; 8.59 g (32.76 mmol) of $PPh_3$; 6.3 ml (2.45 eq) of DEAD; 50 ml of THF. An Argon reflux for 19 hours generated 4.24 g of compound E4 (a white solid), equating to the product yield of 64%.

Then a solution of compound E4, anisole (labeled F4 in FIG. 4), concentrated sulfuric acid (labeled G4 in FIG. 4), and trifluoroacetic acid (labeled H4 in FIG. 4) is refluxed (preferably under an inert atmosphere) for about one hour. The reaction product is evaporated to dryness and loaded into a silica gel column, and eluded by hexane and ethyl acetate (2:1, 1:1 volume ratio) to yield 6,6-Diethyl-6,7-dihydro-2H,5H-4,8-dioxa-2-aza-azulene-1,3-dicarboxylic acid dimethyl ester, the pyrrole derivative labeled I4 in FIG. 4 (hereinafter referred to as compound I4).

A yield of 92% for compound I4 was obtained using the following reaction parameters: 3.29 g (8.20 mmol) of compound E4; 1.34 ml (1.5 eq) of anisole; 80 mg (0.1 eq) of concentrated sulfuric acid, and 60 ml of trifluoroacetic acid. These components were refluxed under Argon for 1 hour, generating 2.36 g of compound I4 (a white solid), equating to a product yield of 92%.

Next, a quantity of compound I4 was dissolved in sodium hydroxide solution (labeled J4 in FIG. 4) and stirred for about 3-6 hours (preferably under an inert atmosphere) while maintaining a constant temperature of about 50-70° C. The resulting solution was cooled and any excess sodium hydroxide was neutralized using concentrated hydrochloric acid (not specifically identified in FIG. 4). The reaction product was collected by filtration and preferably dried under vacuum, to yield 6,6-Diethyl-6,7-dihydro-2H,5H-4,8-dioxa-2-aza-azulene-1,3-dicarboxylic acid, the pyrrole derivative labeled K4 in FIG. 4 (hereinafter referred to as compound K4), a slightly pinkish powder.

A yield of 83% for compound K4 was obtained using the following reaction parameters: 2.36 g of compound I4 was dissolved in 65 ml of 2.5 M sodium hydroxide and was stirred at 60° C. under Argon for 5 hours. The product was collected by filtration and dried under vacuum, yielding 1.77 g of compound K4, equating to a product yield of 83%.

One more reaction is required to obtain the ProDOP-Et2 monomer. A quantity of compound K4 was dissolved in triethanolamine (labeled L4 in FIG. 4) and was briefly heated to about 170-190° C. (preferably under an inert atmosphere). The reaction mixture was poured into water, and the reaction product extracted by dichloromethane (not specifically identified in FIG. 4) using conventional lab techniques. The dichloromethane layer was washed with an aqueous salt solution (referred to as salting out), and then dried (to remove the water) over magnesium sulfate. The clean and dry dichloromethane layer (which contains the reaction product) was filtered, and the filtrate evaporated to dryness and loaded into a sublimation chamber. Sublimation was then performed at high temperatures (about 90-110° C.) under a strong vacuum, yielding the ProDOP-Et2 monomer (labeled M4 in FIG. 4), as a white solid.

A yield of 54% for the ProDOP-Et2 monomer (compound M4) was obtained using the following reaction parameters: 17 g of compound K4 was dissolved in triethanolamine and heated to 180° C. for 8 minutes under an Argon atmosphere. The reaction mixture was poured into water and extracted using four 100 ml aliquots of dichloromethane. The dichloromethane layer was washed with brine and dried over magnesium sulfate. The product was filtered out, dried, and processed in the sublimation chamber at 100° C. under a vacuum of approximately 0.01 mm of mercury, yielding 0.617 g of 6,6-Diethyl-6,7-dihydro-2H,5H-4,8-dioxa-2-aza-azulene, the ProDOP-Et2 monomer (labeled M4 in FIG. 4), equating to a product yield of 54%.

Synthesis of other Monomers

As discussed above, both blue and red EC polymers have been developed. It would also be desirable to achieve EC polymers having different colors. Several approaches can be followed to achieve such different colors. New monomers and conducting polymers can be developed, and hopefully, some of the newly developed monomers will offer different colors. Another approach is to develop copolymers based on existing and/or new monomers, in the hope that the copolymers will exhibit different colors. Developing new EC monomers based on modifications of other EC monomers has several advantages. First, it may be possible to fine tune the color of a monomer by carefully choosing functional groups with different electronic properties. For example, incorporating an electron donating group into an EC monomer will decrease the band gap of the resulting conducting polymers and cause the adsorption bands to include a red shift. Incorporating an electron withdrawing group into an EC monomer will increase the band gap of the conducting polymers, and cause a blue shift in the adsorption band. Second, the resulting materials may inherit the desirable properties of the parent materials, such as good stability, conductivity, contrast ratio, etc. Finally, because the synthetic pathway of the parent EC monomer is known, some of the techniques in synthesizing the parent may be useful in synthesizing a new, yet related monomer.

The present invention is further directed to the synthesis, characterization, and polymerization of new EC monomers generally similar to 3,4-alkylenedioxythiophene (also known as PEDOT). A new first such monomer is 3,4-bis-(2,2,2-trifluoro-ethoxy)-thiophene, which includes an electron withdrawing group. As discussed in detail below, the synthesis of the first new monomer can be easily modified to yield similar fluorinated monomers. A second new monomer based on 3,4-alkylenedioxythiophene is 6,6-dimethy-6,7-dihydro-5H-4,8-dioxa-2-thia-6-sila-azulene, which contains an electron donating group. Initial empirical studies indicate that the new monomers have potential to form EC materials with new colors after polymerization.

The following instruments and materials were used in the synthesis and testing of the additional monomers. 1H NMR spectra were obtained at 300 MHz using a Bruker MSL-300 with $CDCl_3$ solvent and TMS as an internal reference. UV-VIS spectra were recorded using a Jasco V-570 spectrophotometer. Electrochemical measurements were performed on either a Parstat 2263 Advanced Electrochemical System or a CH Instrument Electrochemical Analyzer with a three electrode setup. The working electrodes were a platinum plate, a carbon nanotube/graphite coated glass (Hitachi Powder Metal Inc.), and ITO glass (6±2 Ω/□, Thin Film Device). The reference electrode was silver wire and the counter electrode was platinum wire. Solvents and reagents were used directly without further treatment, except that the solvents and electrolytes for electrochemical measurements were treated by drying over molecular sieves and in a vacuum oven, respectively.

Synthesis of Fluorine Containing EC Monomers Based on 3,4-alkylenedioxythiophene A synthesis for 3,4-bis-(2,2,2-trifluoro-ethoxy)-thiophene, a fluorinated EC monomer, is shown in FIG. 5. In this method, 3,4-Dihydroxy-thiophene-2,5-dicarboxylic acid dimethyl ester, the thiophene derivative labeled A5 in FIG. 5 (hereinafter referred to as compound A5) is first synthesized from commercially available chemicals according to prior art techniques (see K. Zong, L. Madrigal, L. B. Groenendaal, R. Reynolds, Chem. Comm., 2498, 2002). Then a solution of compound A5, 2,2,2-trifluoroethanol (labeled B5 in FIG. 5), $PPh_3$ (labeled C5 in FIG. 5), and DEAD (labeled D5 in FIG. 5) is refluxed in THF for about 15-24 hours (preferably under an inert atmosphere). The reaction mixture is evaporated to dryness. The resulting material is loaded into a silica gel column and eluded by hexane and dichloromethane (4:1, 2:1, 1:1, volume ratio) to yield 3,4-Bis-(2,2,2-trifluoro-ethoxy)-thiophene-2,5-dicarboxylic acid dimethyl ester, the thiophene derivative labeled E5 in FIG. 5 (hereinafter referred to as compound E5).

A yield of 25% for compound E5 was obtained using the following reaction parameters: 3.00 g, (12.92 mmol) of compound A5; 2.84 g (2.2 eq) of 2,2,2-trifluoroethanol; 7.64 g (2.2 eq) of $PPh_3$; 5.00 ml (2.45 eq) of DEAD; and 45 ml of THF. An Argon reflux for 21 hours generated 1.30 g of compound E5 (a white solid), equating to a product yield of 25%.

Next, a quantity of compound E5 is dissolved in a solution of sodium hydroxide and ethanol (labeled F5 in FIG. 5) and stirred for about 12-20 hours (preferably under an inert atmosphere) while maintaining a constant temperature of about 50-70° C. The resulting solution is cooled and any excess sodium hydroxide is neutralized using concentrated hydrochloric acid (not specifically identified in FIG. 5). The reaction product is collected using an ether extraction and purified by loading the product into a silica gel column and eluding using hexane and ethyl acetate (1:1, 1:2, volume ratio). This procedure yields 3,4-Bis-(2,2,2-trifluoro-ethoxy)-thiophene-2,5-dicarboxylic acid, the thiophene derivative labeled G5 in FIG. 5 (hereinafter referred to as compound G5).

A yield of 51% for compound G5 was obtained using the following reaction parameters: 1.30 g (3.28 mmol) of compound E5 was dissolved in a solution of 1.30 g (32.5 mmol) of sodium hydroxide, and 45 ml of ethanol, and stirred at 60° C. under Argon for 16 hours. Excess sodium hydroxide was neutralized using 3 ml of concentrated HCl. The product was collected using the ether extraction and elution techniques noted above, yielding 0.62 g of compound G5, equating to a product yield of 1%.

One more reaction is required to obtain the fluorinated EC monomer 3,4-bis-(2,2,2-trifluoro-ethoxy)-thiophene. A quantity of compound G5 is dissolved in quinoline and a barium promoted copper chromite catalyst is added. Those of ordinary skill in the art will recognize that barium promoted refers to the incorporation of small amounts of barium in a catalyst, to increase the performance of the catalyst. Barium promoted copper chromite catalyst is available from Strem Chemicals, Inc of Newburyport, Mass. The chemical formula of the barium promoted copper chromite catalyst is as follows: 62-64% $Cr_2CuO_4$, 22-24% CuO, 6% BaO, 0-4% Graphite, 1% $CrO_3$, 1% $Cr_2O_3$. The solution of quinoline and the barium promoted copper chromite catalyst is labeled H5 in FIG. 5 (hereinafter referred to as solution H5). The solution of compound G5 and solution H5 is heated to about 170-190° C. for about 12-18 hours (preferably under an inert atmosphere). The reaction mixture is cooled, and then, the reaction product is extracted using an ether workup (those of ordinary skill in the art will recognize that such an ether workup is a common technique in organic chemical synthesis and need not be described in greater detail). The extracted reaction product is dried over magnesium sulfate and purified using a silica gel column and elution with hexane and dichloromethane (1:1, volume ratio), yielding the fluorinated EC monomer 3,4-bis-(2,2,2-trifluoro-ethoxy)-thiophene (labeled I5 in FIG. 5), a white solid. The NMR spectra of compound I5 is shown in FIG. 6.

A yield of 42% for the fluorinated EC monomer 3,4-bis-(2,2,2-trifluoro-ethoxy)-thiophene (compound I5) was obtained using the following reaction parameters: 0.62 g (1.68 mmol) of compound G5 was dissolved in 3.5 ml of quinoline with 0.15 g of barium promoted copper chromite catalyst, and heated to 150° C. for 15 hours under an Argon atmosphere. The reaction mixture was cooled, and the product was collected using the ether extraction and elution techniques noted above, yielding 0.200 g of compound I5, equating to a product yield of 42%.

It should be noted that the synthesis shown in FIG. 5 can be easily modified to achieve other fluorinated EC monomers, simply by replacing 2,2,2-trifluoroethanol (labeled B5 in FIG. 5) with appropriate other fluorinated alcohols, such as 2-fluoroethanol, 2,3,4,5,6-pentfluorobenzyl alcohol, and 2,2-difluoro-1,3-propanediol. Using the synthesis shown in FIG. 5, other fluoro containing EC monomers were produced.

Synthesis of Silicon-containing EC Monomers Based on 3,4-alkylenedioxythiophene

A synthesis for 6,6-dimethy-6,7-dihydro-5H-4,8-dioxa-2-thia-6-sila-azulene, a silicon-containing EC monomer generally related to 3,4-alkylenedioxythiophene, is shown in FIG. 7. First, 3,4-Dihydroxy-thiophene-2,5-dicarboxylic acid dimethyl ester, the thiophene derivative labeled A7 in FIG. 7 (hereinafter referred to as compound A7) is synthesized from commercially available chemicals according to prior art techniques (see K. Zong, L. Madrigal, L. B. Groenendaal, R. Reynolds, *Chem. Comm.*, 2498, 2002). Note that the same initial step is employed in the synthesis of FIG. 5. Then, a solution of compound A5, dihydroxylmethyldimethylsilane (labeled B7 in FIG. 7), PPh$_3$ (labeled C7 in FIG. 7), and DEAD (labeled D7 in FIG. 7) is refluxed in THF for about 15-24 hours (preferably under an inert atmosphere). A small amount of water is then added to quench the reaction. The reaction mixture is evaporated to dryness. The resulting material is loaded into a silica gel column and eluded by hexane and dichloromethane (2:1, 1:1, volume ratio) to yield 6,6-Dimethyl-6,7-dihydro-5H-4, 8-dioxa-2-thia-6-sila-azulene-1,3-dicarboxylic acid dimethyl ester, the silicon-containing thiophene derivative labeled E7 in FIG. 7 (hereinafter referred to as compound E7).

A yield of 41% for compound E7 was obtained using the following reaction parameters: 10.0 g, (43.06 mmol) of compound A7; 5.18 g (1.0 eq) of dihydroxylmethyldimethylsilane; 22.59 g (2.0 eq) of PPh$_3$; 16.6 ml (2.45 eq) of DEAD; and 100 ml of THF. An Argon reflux for 18 hours generated 5.60 g of compound E7 (a white solid), equating to a product yield of 41%.

Next, a quantity of compound E7 is dissolved in a solution of sodium hydroxide and ethanol (labeled F7 in FIG. 7) and refluxed for about 12-20 hours (preferably under an inert atmosphere). The resulting solution is cooled and any excess sodium hydroxide is neutralized using concentrated hydrochloric acid (not specifically identified in FIG. 7). The reaction product is collected using an ether extraction, dried over magnesium sulfate, and purified by loading the product into a silica gel column and eluding using hexane and ethyl acetate (1:1, 1:2, volume ratio), yielding 6,6-Dimethyl-6,7-dihydro-5H-4,8-dioxa-2-thia-6-sila-azulene-1,3-dicarboxylic acid, the silicon-containing thiophene derivative labeled G7 in FIG. 7 (hereinafter referred to as compound G7).

A yield of 84% for compound G7 was obtained using the following reaction parameters: 5.20 g 16.4 mmol) of compound E7 was dissolved in a 2.5 M solution of sodium hydroxide with 100 ml of ethanol, and refluxed under Argon for 16 hours. Excess sodium hydroxide was neutralized using 15 ml of concentrated HCl. The product was collected using the ether extraction and elution techniques noted above, yielding 2.77 g of compound G7, equating to a product yield of 84%.

One more reaction is required to obtain the silicon-containing EC monomer 6,6-dimethy-6,7-dihydro-5H4,8-dioxa-2-thia-6-sila-azulene. A quantity of compound G7 is dissolved in quinoline and a copper chromite catalyst is added. The solution of quinoline and the copper chromite catalyst is labeled H7 in FIG. 7 (hereinafter referred to as solution H7). The solution of compound G7 and solution H7 is heated to about 170-190° C. for about 14-20 hours (preferably under an inert atmosphere). The reaction mixture is poured into water, and then the reaction product is extracted using ether, as is known by those of ordinary skill in the art. The extracted reaction product is dried over magnesium sulfate, filtered, and evaporated to dryness. The product is purified using a silica gel column and elution with hexane and ethyl acetate (2:1, volume ratio), yielding the silicon-containing EC monomer 6,6-dimethy-6,7-dihydro-5H-4,8-dioxa-2-thia-6-sila-azulene, (labeled 17 in FIG. 7), a colorless oily liquid. The NMR spectra of compound I7 is shown in FIG. 8.

A yield of 1% for the silicon-containing EC monomer 6,6-dimethy-6,7-dihydro-5H-4,8-dioxa-2-thia-6-sila-azulene, (compound I7) was obtained using the following reaction parameters: 0.24 g of compound G7 was dissolved in 3.0 ml of quinoline with 0.080 g of barium promoted copper chromite catalyst, and heated to 150° C. for 17 hours under an Argon atmosphere. The reaction mixture was cooled, and the product was collected using the ether extraction and elution techniques noted above, yielding 2.0 mg of compound I7, equating to a product yield of 1%.

Silicon has smaller electron negativity than carbon, so that when silicon functional groups are introduced into conducting polymer chains, electron donating effects may be achieved, and the absorption band of the resulting polymer should experience a red-shift. The introduction of the silicon functional groups will also cause changes in the polarity of the matrix and length of the conjugated chain of the conducting polymer, which will affect the position of the absorption band, i.e., the band gap. In the above-described synthesis, good yields were obtained in every step but the last (i.e., which had the 1% yield). This last step, the decarboxylation, was attempted using different reaction parameters, including various catalysts (and no catalyst), and including copper chromite, barium promoted, bronze powder, and no catalyst. Further modifications included varying the reaction temperature from 150° C. to 250° C., and eliminating the use of the quinoline solvent. The best yield so far is about 1%, using the parameters discussed above in detail. Optimization of the reaction conditions is still being investigated.

Synthesis of EC Polymers Films Using Electropolymerization

One aspect of the present invention is directed to a method for producing EC polymer films using electropolymerization. Two related electropolymerization techniques can be employed to polymerize EC monomers in order to achieve a high quality EC polymer film. Density is required to achieve the high contrast between the bleached and unbleached states. High quality is required for repeatability over many cycles. EC polymer films that do not exhibit high contrast and repeatability over many cycles are not very useful as components in EC polymer-based devices, such as windows and displays.

EC polymer films were produced based on 3,4-bis-(2,2,2-trifluoro-ethoxy)-thiophene (compound I5), the fluorinated EC monomer whose synthesis is shown in FIG. 5. A first electropolymerization technique is summarized in a flow chart 200 in FIG. 9. EC monomers are prepared in a block 202, and then cyclic voltammetry is employed, as indicated in a block 204, to polymerize the EC monomer and to deposit the resultant polymer as a film on a substrate, preferably an indium tin oxide (ITO) coated transparent substrate.

In an exemplary implementation of the electropolymerization techniques described herein, the synthesis of FIG. 5 was used to produce a monomer for electropolymerization. It should be understood that the electropolymerization techniques of the present invention can also be implemented with other EC monomers whose synthesis is described herein, as well as with EC monomers synthesized using conventional or other methods. For example, the preparation of ProDOP and ProDOP-Me$_2$ monomers, red colored EC monomers, are described in the following publications: (1) C. Cheng, J. Gulia, S. Rokita, C. Burrows, J. of Mole. Cat. A: Chemical, 113, pp. 379-391, 1996; (2) A. Mertz, R. Schropp, E. Dotterl, Synthesis, 7, pp. 795-800, 1995; and (3) K. Zong, J. R. Reynolds, J. Org. Chem. 66, pp. 6873-6882, 2001. Any of the techniques described in these or other related publications can be used to prepare the monomers, as indicated in block 202 of FIG. 9.

Referring now to a block 204 of FIG. 9, polymerization of 3,4-bis-(2,2,2-trifluoro-ethoxy)-thiophene (compound I5) was achieved using cyclic voltammetry under the following conditions. The cyclic voltammetry curve of compound I5 is shown in FIG. 11. The working electrode employed was a platinum plate. The concentration of the monomer (compound I5) was about 0.01 M, and lithium trifluoromethanesulfonate (CF$_3$SO$_3$Li) was used as the supporting electrolyte, at a concentration of 0.10 M in acetonitrile. A scan rate of 50 mV/s was employed. The current-voltage (CV) curve of FIG. 11 shows that significant oxidation of the monomer occurs at 1.5 V. At about 0.9 V, there is another small oxidative peak, whose cause has not yet been identified. Typical redox peaks of conducting polymers aren't present, because polymerization is not complete. As noted below, a plurality of different working electrodes, supporting electrolytes, and solvents were tested, however, the monomer has not yet been polymerized.

Chronoamperometry was used to test the polymerization condition of 3,4-bis-(2,2,2-trifluoro-ethoxy)-thiophene (compound I5). Four different supporting electrolytes (lithium perchlorate, tetrabutylammonium perchlorate, CF$_3$SO$_3$Li, and N-lithiotri-fluoromethanesulfonimide), two different solvents (acetonitrile and propylene carbonate), and three different working electrodes (platinum plate, carbon nanotube/graphite, and ITO glass) were used. The concentration of the solution for this electrochemical testing was 0.01 M for the monomer (compound I5) and 0.10 M for the supporting electrolyte. The results of these tests, graphically illustrated in FIG. 12, indicate that the combination of a platinum working electrode, CF$_3$SO$_3$Li as the supporting electrolyte, and acetonitrile as the solvent performed best.

Upon electrochemical oxidation, thin layers of an EC polymer having a purple color formed on the surface of the electrodes on several occasions. The intensity of the color was deepest on the platinum working electrode, as compared to the carbon nanotube/graphite and ITO glass working electrodes. The area of the working electrode employed was about 1.0 cm$^2$. The chronoamperometry curves in FIG. 12 are different than those of more typical electrochemical polymerizations, which generally exhibit current increases over time. It is clear that the oxidative charges for the three working electrodes examined are different, with the platinum working electrode having the greatest oxidative charge, followed by the carbon nanotube/graphite working electrode, and finally the ITO working electrode. Optimization of the electrochemical polymerization and chemical polymerization of 3,4-bis-(2,2,2-trifluoro-ethoxy)-thiophene (compound I5) is still under investigation.

The second electropolymerization technique in accord with the present invention is summarized in a flow chart 212 in FIG. 10. This second technique has been empirically tested with ProDOP-(CH$_3$)$_2$ and ProDOP. Once again, EC monomers were prepared in a block 214 (as described above). Once the starting monomer was obtained or prepared, the monomer is polymerized first using chronoamperometry, as indicated in a block 216, followed by cyclic voltammetry, as indicated in a block 218. The second electropolymerization technique combining both chronoamperometry and cyclic voltammetry appears to achieve a higher quality, more durable EC polymer film.

Referring now to block 216 of FIG. 10, the first step in the two part electropolymerization of the EC monomer can be achieved using chronoamperometry under the following conditions. Oxidative electrochemical polymerization of the monomer was initiated using chronoamperometry (100 sec, 0.88 V for ProDOP-(CH$_3$)$_2$) to deposit a very thin, very uniform layer of EC polymer onto an ITO coated glass substrate using a platinum wire as a counter electrode. Once again, the selected monomer was placed into a propylene carbonate solution with tetrobutylammonium perchlorate salt (0.01 M of the monomer and 0.1 M of tetrobutylammonium perchlorate).

In a block 218, multiple scan cyclic voltammetry is employed to deposit additional polymer onto the uniform layer deposited using chronoamperometry. As noted above, using parameters of +0.8 to ~−1.0 V, a scanning rate of 20 mV/s, and 10 cycles, polymerized ProDOP-(CH$_3$)$_2$ can be deposited. Additional cycles may be required for the deposition of an acceptably dense layer of polymerized ProDOP.

Subtractive Color Mixing

Yet another aspect of the present invention is to achieve EC polymer devices exhibiting addition colors using the concept of subtractive color mixing effect. By overlaying different EC films, corresponding absorption bands can be removed from ambient light resulting in new colors. Subtractive color mixing is a fundamental principle in painting, and can also be used to achieve new colors with EC materials. By overlaying different EC films, corresponding absorption bands can be removed from the ambient light, resulting in new colors This idea is demonstrated for the present invention by simply overlaying red and blue EC films to achieve a black color. Upon electrochemical redox, the overlapped films switch between black and transparent states. This type of EC material application may have potential application as an electronic ink.

To provide a working example of this concept, an EC device including two well-known EC polymer films, one blue EC polymer and one red EC polymer, was constructed. The blue EC polymer employed is based on the 3,3-Dimethyl-3,4-dihydro-2H-thieno[3,4-b][1,4]dioxepine monomer, (also known as ProDOT-Me2), a derivative of 3,4-alkylenedioxythiophene. The red EC polymer employed is based on the 6,6-dimethyl-6,7-dihydro-2H,5H-4,8-dioxa-2-aza-azulene monomer, a derivative of 3,4-alkylenedioxypyrrole.

The ProDOT-Me2 monomer forms a blue EC polymer film on ITO glass upon electrochemical polymerization. The maximum absorption wavelength ($\lambda$max) is 579 nm. The red, orange, and yellow light wavelengths of white light are absorbed, resulting in blue color wavelengths being transmitted by the polymer film.

The 6,6-dimethyl-6,7-dihydro-2H,5H-4,8-dioxa-2-aza-azulene EC monomer forms a red EC polymer film upon polymerization, having a $\lambda$max at 529 nm. The red EC polymer film adsorbs blue, cyan, and green light wavelengths, and therefore, transmits red color wavelengths. FIG. 13 graphically illustrates the absorption curves of theses red and blue EC polymers in their reduced states, with blue EC polymer being represented by the solid line, and the red EC polymer being represented by the dash line. The two absorption bands cover the entire visible light range. By overlapping theses two EC polymer films, the entire visual wavelength band can be absorbed to a certain degree. These two EC polymers were used to achieve a visually appearing black color, by color mixing.

In order to absorb light with different wavelengths equally, to avoid a tilted absorption band having either a yellow cast or a blue cast, it is necessary to match the absorbance of both the blue and red films. In the range of the Beer-Lambert law, the absorbance (A) has a linear relation with either the thickness of the film or the charge (O) injected into the film during polymerization. In fabricating an EC device combining the red and blue EC polymer films to absorb all light (i.e., to achieve a visual black color), it was decided to match the absorbance of the red and blue EC polymer films by controlling Q, the charge. FIG. 14 graphically illustrates the charge/time curves of the polymerizations of the blue and red films shown in FIG. 13, with the data for the blue EC polymer being represented by line 1, and the data for the red EC polymer being represented by line 2. From this data, the color efficiency (η) of each EC polymer can be calculated by using the following equation:

$$\eta(\text{color efficiency})=A(\text{absorbance})/Q(\text{charge})$$

According to the data of FIGS. 13 and 14, the η value of the blue polymer is 92 $cm^2C^{-1}$ and the η value of the red polymer is 45 $cm^2C^{-1}$. The following parameters were employed to collect the data of FIGS. 13 and 14. The concentrations of the monomer and supporting electrolyte were 0.01 M and 0.10 M in acetonitrile, respectively. The oxidative potentials were 1.2 V for blue EC polymer and 1.0 V for red EC polymer, both relative to an Ag wire reference. When these conditions are fixed, the absorbance of the EC polymer film can be controlled by the polymerization time.

The simplest method of color mixing was tried first. A blue EC polymer film and a red EC polymer film were deposited on two ITO glass plates separately. Then, the two ITO glass plates were clipped together with the glass sides facing each other and the polymer films facing out. FIG. 15 graphically illustrates the cyclic voltammetry curves of the blue EC polymer and the red EC polymer, with the oxidized state being indicated with a dash line, and the reduced state being indicated with a solid line. According to these CV curves, +1 to −1 volts was used to switch the specimen to avoid over oxidation. The switching results were recorded by UV-VIS and are graphically illustrated in FIG. 16, which shows the UV-Visual spectrum of the redox states of the specimen, with the data for the blue EC polymer being represented by line 1, and the data for the red EC polymer being represented by line 2. The difference of transmittances between transparent and opaque states is 40%. Human eyes will perceive the EC device switching between black and transparent states.

Instead of depositing the EC polymer films on different substrates, depositing the blue and red layers one atop another was attempted. The formal redox potential of the blue polymer is 0.1 V, and the polymerization potential is 1.2 V. For the red polymer, the two potentials are −0.3 V and 0.9 V, respectively. It was therefore determined that it would be better to deposit the blue polymer film first, and then deposit red polymer. If the red polymer were deposited first, the red film might be over oxidized and damaged. Thus far, these attempts have not been successful, and further investigation is being performed.

FIG. 36 schematically illustrates an EC device 360 implementing subtractive color mixing to enable three different colors to be achieved with only two different color EC polymers. EC device 360 includes a red EC polymer device 362 and a blue EC polymer device 364. EC polymer devices 362 and 364 can be implemented using a cathodic polymer layer, a gel electrolyte, and a counter electrode as described in connection with FIGS. 18A and 18B, or using multiple EC polymers as indicated in FIGS. 17A and 17B. EC polymer devices 362 and 364 are then assembled into a single EC device 360. Alternatively, a single EC device utilizing a red polymer and a blue polymer can be implemented. Note that the EC polymer device 362 and EC polymer device 364 are offset from one another, such that the EC devices do not completely overlap. Ambient light 361 enters EC device 360, as indicated in FIG. 36. When EC polymer devices 362 and 364 are in the transparent state, ambient light passes through EC device 360 substantially unchanged. However, when EC polymer devices 362 and 364 are in the colored states, ambient light passing through EC device 360 is modified, as indicated in FIG. 36. The portion of ambient light passing through only EC device 362 will be emitted from EC device 360 as red light 363. The portion of ambient light passing through only EC device 364 will be emitted from EC device 360 as blue light 367. The portion of ambient light passing through both EC device 362 and EC device 364 will be substantially blocked, so that an observer will see only black in that portion of EC device 360, as indicated by a block 365. It should be understood that if desired, EC device 362 and EC device 364 could be aligned, so that EC device 360 would either substantially pass light unaffected when the EC devices are in the first state, and EC device 360 would substantially block all visible light when the EC devices are in the second state.

EC Device Configurations

Another aspect of the present invention is directed at specific configurations of EC devices using EC polymers. Each configuration disclosed herein is based on a laminated system including at least one EC polymer, a solid or liquid electrolyte, and upper and lower layers of transparent electrodes.

A first configuration for an EC device is schematically illustrated in a transparent state 40a in FIG. 17A, and a colored state 40b in FIG. 17B. Note that structurally, there is no difference in the EC device when in the transparent state or the colored state. When a voltage is applied to the EC device, the EC polymers of the cathode and anode layers undergo a color change. The first configuration, as collectively illustrated in FIGS. 17A and 17B, thus includes a cathodic (PProDOT-Me$_2$) EC polymer layer and an anodic (PBEDOT-NMeCz) EC polymer layer, although it should be understood that other EC polymers discussed herein can be employed instead. The polarity of the applied voltage is important. If a positive voltage is applied, the EC polymers of the present invention will either stay in the bleached state (assuming there was no negative voltage applied immediately prior to applying the positive voltage), or transition from the opaque state to the bleached state (assuming there was a negative voltage applied immediately prior to applying the positive voltage). If a negative voltage is applied, the EC polymers of the present invention will either stay in the opaque state (assuming there already was a negative voltage being applied immediately prior to applying additional negative voltage), or transition from the bleached state to the opaque state (assuming there was either a positive voltage applied immediately prior to applying the negative voltage, or that no voltage was applied immediately prior to applying the negative voltage).

A top layer is a transparent electrode 42, preferably formed from an ITO coated transparent substrate. While an ITO film on a transparent substrate represents a preferred transparent electrode, it should be understood that other materials, such as tungsten oxide and doped zinc oxide films over transparent substrates can be beneficially employed as a transparent electrode. Also, while glass certainly represents a preferred transparent substrate, other transparent materials, such as plastics and polymers, can also be beneficially employed as a transparent substrate. The use herein of the term "glass substrate" should be considered to be exemplary, rather than limiting on the scope of the present invention, and it is intended that other transparent substrates are contemplated other than glass.

The next layer is a cathodic PProDOT-Me$_2$) EC polymer layer, which in FIG. 17A, is shown as a transparent layer 44a, and in FIG. 17B, is shown as a colored layer 44b. It should be understood that when no voltage (or a positive voltage) is applied, the PProDOT-Me$_2$ EC polymer layer is not completely colorless. Instead, a light blue tint can be discerned (hence the shading in transparent layer 44a of FIG. 17A). As a negative voltage is applied, the PProDOT-Me$_2$ EC polymer layer becomes progressively more opaque, until it reaches saturation (a dark blue tint, as indicated by the shading in colored layer 44b of FIG. 17B).

Adjacent to the cathode EC polymer layer is a solid/gel electrolyte layer 46. The solid/gel electrolyte layer is followed by an anodic (PBEDOT-NMeCz) EC polymer layer, which is illustrated as being a transparent layer 48a in FIG. 17A, and a colored layer 48b in FIG. 17B. Even with no voltage applied (or if a positive voltage is applied), PBEDOT-NMeCz is not colorless, and a definite yellowish tint is apparent (hence, the shading in transparent layer 48a of FIG. 17A). Again, as a negative voltage is applied, the PBEDOT-NMeCz EC polymer layer becomes progressively more opaque, until it reaches saturation (a moderate blue tint, as indicated by the shading in colored layer 48b of FIG. 17B). The PBEDOT-NMeCz EC polymer layer is followed by a bottom layer, which is an additional transparent electrode 42, also preferably formed from indium tin oxide (ITO) coated glass.

The first configuration (FIGS. 17A and 17B) provides a dual EC polymer device, in which the darkness (or opacity) of colored state is increased by using two EC polymers. However, the transmittance of the bleached state is decreased, primarily because the anodic polymer has a noticeable tint in the transparent (or bleached) state. The monomer (e.g., BEDOT-NMeCz) used to generate the anodic EC polymer (e.g., PBEDOT-NMeCz) is somewhat difficult to synthesize, although the present invention does encompass a method for its synthesis.

The cathodic layer, which is based on a poly(3,4-propylenedioxythiophene) derivative (PProDOT-Me$_2$), expresses an excellent light transmittance change of 78 percent between the bleached and unbleached states. PProDOT-Me$_2$ exhibits rapid switching, low oxidation potentials, and excellent stability at ambient and elevated temperature.

Both poly(vinyl chloride) (PVC) based and polymethylmethacrylate (PMMA) based gel electrolytes containing lithium perchlorate (LiClO$_4$) can be employed for solid electrolyte layer 46. In one embodiment, solid electrolyte layer 46 is fabricated from PVC (or PMMA), propylene carbonate (PC), ethylene carbonate (EtC), and LiClO$_4$. The PVC (or PMMA) electrolyte mixture is dissolved in tetrahydrofuran (THF). Either PVC or PMMA-based gel electrolytes provide high conductivity (2 mS/cm) at room temperature.

In other embodiments, PMMA based gel electrolytes were prepared and differed by the salt and solvents used. The salts that were investigated include: lithium perchlorate (LiClO4), tetrabutyl ammonium perchlorate (TBAP) and trifluorosulfonimide (LiN(CF$_3$SO$_2$)$_2$. The solvents used were PC, EtC, acetonitrile (ACN) and γ-butyrolactone (GBL), and were substantially dried over molecular sieves before use. The gel electrolytes were synthesized by first dissolving the salt in the solvent and then adding the PMMA. A highly conductive (2 mS/cm), viscous and transparent (88%) gel electrolyte was formed.

Still another useful gel electrolyte can be prepared from 3% LiClO$_4$, 7% PMMA, 20% PC and 70% acetonitrile (ACN) (% by weight). A simple synthesis of such a gel is achieved by first dissolving the PMMA and LiClO$_4$ in ACN. PC was dried over 4 angstrom molecular sieves and then combined with the other ingredients. The complete mixture was stirred for 10-14 hours at room temperature. A high conductivity (2 mS/cm), high viscosity and transparent gel electrolyte was formed. As described above, the solid polymer matrix of PMMA provides dimensional stability to the electrolyte, while the high permittivity of the solvents PC and ACN enable extensive dissociation of the lithium salt. The low viscosity of PC provides an ionic environment that facilitates high ionic mobility.

Gel electrolytes are discussed in greater detail below. While gel electrolytes are preferred because they facilitate the production of a solid state device (the solvent liquid is contained within the polymer matrix), liquid electrolytes can be used in an EC device. One such liquid electrolyte can be achieved using 0.1 M tetrabutylammonium perchlorate (TBAP) in ACN. It is contemplated that materials other than PVC and PMMA can be employed to provide a polymer matrix for a gel electrolyte, and that materials other than TBAP and LiClO$_4$ can be employed as ionic sources. It should be noted that in the context of the present invention, the terms "gel electrolyte" and "solid electrolyte" are use synonymously, because the liquid materials employed in fabricating a gel electrolyte are absorbed in a polymer matrix, and there are substantially no free liquids that are not contained within the polymer matrix.

A second preferred configuration for an EC device is similarly schematically illustrated in both a transparent state 50a in FIG. 18A, and a colored state 50b in FIG. 18B. Again, from a structural standpoint, there is no difference in the EC device when in its transparent state or its colored state. The second configuration, as collectively illustrated in FIGS. 18A and 18B, includes a cathodic PProDOT-Me$_2$ EC polymer layer and a counter electrode layer, but not an anodic PBEDOT-NMeCz EC polymer layer. As before, the polarity of the voltage applied determines how the device will respond.

Again, the top layer is transparent electrode 42, again, preferably ITO. The next layer is a cathodic PProDOT-Me$_2$ EC polymer layer, which in FIG. 4A is shown as a transparent layer 44a, and in FIG. 18B is shown as a colored layer 44b. After the cathode EC polymer layer, is a solid/gel electrolyte layer 46. The solid electrolyte layer is followed by a counter-electrode layer 52. No bottom transparent electrode layer is required or included.

Counter-electrode layer 52 is preferably gold-based, platinum-based, or highly conductive carbon-based, and replaces the anodic EC polymer and bottom ITO electrode used in the first configuration described above. A preferred highly conductive carbon is graphite. It should be understood that while graphite certainly represents a preferred highly conductive carbon, other highly conductive carbon materials can instead be beneficially employed as a conductive film applied as a coating on a transparent substrate to produce a counter-electrode. Many types of conductive carbons are available from a variety of manufacturers, such as Tokai Carbon Co. of Tokyo, Japan; and Loresco International, of Hattiesburg, Miss. Thus, the use of the term "graphite" herein should be considered to be exemplary, rather than limiting on the scope of the present invention. It is further contemplated that nickel can be beneficially employed as a conductive film on a transparent substrate to produce a counter-electrode. The use of a counter-electrode can improve the speed of the color change between states, as well as improve the contrast ratio between the two states. The counter-electrode material should be chemically stable, provide high electrical conductivity, and should be easy to fashion into a patterned substrate. Gold, highly conductive carbons, and platinum have been identified as being electrically conductive materials that can be beneficially employed for making a counter-electrode. It is contemplated that graphite will be very useful because of its low cost. Gold, while much more expensive, can be used in very thin layers, thereby minimizing the cost of a gold-based counter-electrode. Platinum, while electrically conductive, is likely to be so expensive as to preclude its use. It is further contemplated that still other conductive materials can be employed to produce the counter-electrode.

A gold-based counter-electrode was produced as described below, and is illustrated in FIGS. 19A-19C. Polished float glass, 0.7 mm thick (available from Delta Technologies, Limited), was used as a substrate. The glass was cut into a 4 inch diameter glass wafer 56. Lithography and sputtering techniques were used for forming a gold pattern 58 on the glass wafer. Optionally, before the gold coating was applied, a layer 60 of titanium-tungsten (TiW) was first sputtered onto the glass substrate. TiW layers have often been used as barrier layers and capping layers in semiconductor manufacturing. The TiW layer helps tightly bind the gold layer to the glass substrate. The pattern design, or pattern geometry, ultimately affects the EC device. The wider lines of conductive material on the counter-electrode, and the larger open areas of the patterning are expected to provide higher conductivity, thus enhancing the speed of the color change of the EC polymer, at the cost of decreasing transmittance through the counter-electrode when no voltage (or a positive voltage) is applied.

For some applications, particularly windows, transmittance through the EC device is very important. If the maximum transmittance through the EC device (or through any part of the device, such as the counter-electrode) is reduced to an unacceptable level, then the device may not be suitable for use in an application such as for a window. The checkerboard pattern shown in FIGS. 19A and 19B offers a pattern that, when sufficiently small, is substantially transparent. It is contemplated that as an alternative to the square orifices in the gold layer, circular orifices or diamond shaped orifices would be equally useful, as respectively shown in FIGS. 19D and 19E. Preferably, less than 25 percent of the glass substrate is covered with gold, in order to maintain high transmittance. It should be noted that transmittance is maximized when the total area of the layer of gold (or graphite) is minimized, while conductivity is maximized when the area of the layer of gold (or graphite) is maximized. If an EC device must have excellent transmittance, and a somewhat slower response time is acceptable, then the percentage of the counter-electrode surface area devoted to a gold or graphite layer can be decreased. On the other hand, if response time is more important than transmittance, then the percentage of the counter-electrode area devoted to a gold or graphite layer can be increased. It has been empirically determined that covering less than 25 percent of the glass substrate with the conductive material represents a good compromise for EC devices that exhibit both rapid response times and acceptable transparency.

As noted above, highly conductive carbon (such as graphite) based counter-electrodes can also be employed. A first embodiment of a highly conductive carbon-based counter-electrode is shown in FIGS. 19E and 19F. Once again, a preferred substrate is a polished float glass cuvette plate, about 0.7 mm thick. An ITO coating 64 is applied on one side of the polished float glass cuvette plate, and a carbon coating 62 is then applied over the ITO coating. Preferably, the highly conductive carbon material is graphite (HITASOL GA.66M). The electrical conductivity of this highly conductive carbon material is known to be not less than $10^{-2}$ S/cm. Preferably, less than 25 percent of the glass substrate is covered with the carbon, in order to maintain high transmittance. While lithography and sputtering were employed for gold patterning on glass substrate as described above, screen printing was employed for forming a graphite pattern on a glass substrate for the highly conductive carbon-based counter-electrode. It is anticipated that because screen printing technology requires less expensive equipment than does lithography and sputtering techniques, that mass production of highly conductive carbon-based counter-electrodes may be less expensive than mass production of gold-based counter-electrodes.

Note that in this embodiment of a graphite-based counter-electrode, the glass substrate is coated with indium tin oxide on one side to form a transparent insulating substrate for the counter-electrode. Because the electrical conductivity of gold is much higher than that of graphite, gold can be directly deposited on the glass substrate without ITO glass, but it is preferable to deposit a graphite pattern onto an ITO layer.

Preferably, each polymer layer within these laminated devices are on the order of 150 nanometers in thickness, each solid electrolyte layer is approximately 30 microns in thickness, and the gold patterned layer on the counter-electrode is on the order of 50-100 nanometers in thickness. A preferable range of thickness for a graphite layer in a counter-electrode is also 50-100 nanometers, more preferably 100 nanometers. A preferred thickness for an ITO film is from about 10 nanometers to about 200 nanometers, with more electrical conductivity being provided by a thicker layer. Thus, electrical conductivity within an EC device can be manipulated by adjusting the thickness of the ITO layer, especially an ITO layer employed in a counter-electrode. A preferred thickness for a transparent substrate (such as glass or plastic) utilized in a transparent electrode (or counter-electrode) is about 0.5-1.0 millimeters, most preferably 0.7 millimeters.

A platinum wire has been successfully employed as a counter-electrode in an EC device generally corresponding to the second configuration as shown in FIGS. 18A and 18B. While EC devices having a specific configuration (i.e., a cathodic EC polymer, a solid electrolyte layer, and a non EC polymer counter-electrode) preferably employ PProDOT-Me$_2$ as the cathodic layer, it should be understood that other EC cathodic polymers can be beneficially employed. It should be understood that a single polymer EC device can be fashioned using a counter-electrode and an anodic EC polymer, as opposed to a counter-electrode and a cathodic EC polymer. A single polymer EC device fashioned using a counter-electrode and an anodic EC polymer would be less transparent (i.e., the anodic EC polymer layer would be in its darker state) with no voltage (or with a positive voltage) applied, and as a negative voltage is applied to the such an EC device, the anodic EC polymer layer would transition to its more transparent state. This result is the opposite of a single polymer EC device fashioned using a counter-electrode and a cathodic EC polymer, which is more transparent without a voltage (or with a positive voltage) applied, and become more opaque as a negative voltage is applied.

A sample device based on the single polymer/counter-electrode EC device described above was constructed using rectangular layers substantially 7 mm×50 mm. An ITO coated 7 mm×50 mm glass slide was prepared for the transparent electrode, and a layer of PProDOT-Me$_2$ was deposited on the ITO coated surface. A glass wafer onto which a grid pattern of gold had been deposited was cut into 7 mm×50 mm plates. Similar 7 mm×50 mm plates of graphite deposited in a grid pattern were also prepared. A PMMA/LiClO$_4$ gel electrolyte was uniformly placed between the cathodic EC polymer deposited on the ITO slide and the counter-electrode to form a layered device. Two devices were prepared, one with a gold counter-electrode, and one with a graphite counter-electrode layer. The graphite-based counter-electrode differs from the gold-based counter-electrode in that a layer of ITO was first placed on the glass substrate before the graphite was deposited, while no such layer was employed in the gold-based counter-electrode. A rubber sealant was applied, and the assembled devices were allowed to cure for about 20 hours. It is contemplated that additional curing time might be beneficial, and that 20-30 hours represents a preferred range of cure times. The sealant employed was a parafilm, which is a readily available, semi-transparent, flexible thermoplastic sealant. A schematic illustration of these working models is provided in FIGS. 20A and 20B. The working models are consistent with the second embodiment discussed above in connection with FIGS. 18A and 18B. As above, the schematic model is shown in both an oxidized state (no voltage or a positive voltage applied) and a reduced state (a negative voltage applied).

FIG. 20A schematically shows a cross-sectional view and a top plan view of a working model in an oxidized state (no voltage or positive voltage applied). The cross-sectional view clearly shows the top layer as comprising transparent electrode 42, which was prepared by coating glass slide with ITO. Immediately adjacent to transparent electrode 42 is transparent layer 44a, a thin film of the cathodic PProDOT-Me$_2$ EC polymer coated onto transparent electrode 42. The next layer includes a generally circular solid/gel electrolyte layer 46, which is surrounded by a sealant 53 to prevent any of the electrolyte from leaking. As discussed above, the solid electrolyte layer (and sealant) is followed by counter-electrode layer 52. The shape of the solid electrolyte layer defines that area of the EC polymer layer that will change color. Portions of the EC polymer layer that are not in contact with the electrolyte layer will not undergo a change in color. In this example, the EC polymer layer coated the entire generally square-shaped transparent substrate, the sealant was applied as a generally circular mask (i.e., the sealant was applied over the entire surface of the EC polymer layer except for a generally circular portion) and the solid electrolyte layer was deposited within the generally circular portion defined by the sealant mask.

A quite sharp demarcation between portions of the EC polymer immediately adjacent to the solid electrolyte layer (such portions transitioning from a light state to a dark state under an applied negative voltage) was achieved relative to portions of the EC polymer layer immediately adjacent to the sealant (i.e., not immediately adjacent to the solid electrolyte layer, such portions not transitioning from a light state to a dark state under an applied negative voltage). Very little bleed-though occurred at the interface between the sealant and the solid electrolyte layer, enabling a sharply defined window (i.e., the portion of the EC polymer layer that transitioned from light to dark under an applied negative voltage) to be achieved. Of course, the sealant mask and electrolyte area can be combined in shapes other than the generally circular shape employed here. Whatever the shape chosen, the sealant can be conformed and can be used to define a window corresponding to the inverse of that shape, by filling the inverse (i.e., the void) with the electrolyte. No bottom transparent electrode layer is required. FIG. 20B shows the working model after a negative voltage has been applied, and the portion of the EC polymer layer in contact with electrolyte has changed color, while the balance of the EC polymer layer (i.e., the portion in contact with the sealant) has not. With respect to FIGS. 20A and 20B, as noted above, the polarity of the voltage applied determines how such devices will respond.

In addition to the EC devices schematically shown in FIGS. 18A, 18B, 20A, and 20B, FIGS. 20C-20F, which are discussed below, provide additional details on exemplary EC devices that include a single EC polymer and a counter electrode. Both a gold-based and a carbon-based counter electrode have been implemented in working prototypes. For a gold-based counter electrode, polished float glass (Delta Technologies, Limited, 0.7 mm thick) was used as a substrate for the Au-based counter-electrode. The glass was cut into 4 inch diameter wafers for a photo resist spin coating. Lithography and sputtering were used to form the Au pattern on the glass wafer. Before the Au sputtering, TiW was first sputtered on the glass substrate to tightly bind the Au to the glass substrate.

The carbon-based counter-electrode was prepared for comparison with the Au-based counter-electrode. The substrate for the carbon coating is a polished float glass cuvette plate coated with ITO on one side with Rs<10 Ω (Delta Technologies, Limited, 0.7 mm thick). The carbon material used is HITASOL® GA.66M. Its electrical conductivity is not less than $10^{-2}$ S/cm. The covering percentage of the carbon materials is below 20%, in order to maintain high visible light transmittance.

To fabricate a working EC device, slides of L×W×T=50× 7×0.7 mm$^3$, 25.4×25.4×0.7 mm$^3$ and 75×75×0.7 mm$^3$ were cut from an Au-patterned glass wafer and a carbon-patterned ITO glass plate. The gel electrolyte was uniformly placed between the cathodic EC polymer deposited on an ITO slide and the counter-electrode to form the device. Parafilm was employed for tightly sealing the device.

Four EC monomers, ProDOT-Me2 (blue), ProDOT-Me-Pro (blue), ProDOP-Me2 (red), and ProDOP-Et2 (red) have successfully electro-polymerized, generally as discussed above. Variable color (depending on their oxidation state) EC polymer films were electrochemically deposited on ITO glass. Chronoamperometry and multiple cyclic voltammetry (CV) were used for the electropolymerization of the blue EC monomers and the red EC monomers, respectively.

Chronoamperometry and cyclic voltammetry were used to determine if the EC polymer degrades with cycling. The blue EC monomer was electro polymerized on ITO glass (7 mm×15 mm) for 20 seconds. This test was repeated for several film thicknesses, varied by increasing or decreasing the polymerization time and potential. The ~100 nm film yielded the highest % ΔT (77%), while the ~380 nm film had a smaller % ΔT, but could obtain an opaque transmittance close to 0%, blocking transmission of almost all light at the 580 nm wavelength.

Lifetime testing was performed on the polymer and ITO glass combination in an electrolyte solution. The EC polymer successfully switched between the fully oxidized and reduced states for 50,000 cycles in a 0.1 M PC and $LiClO_4$ electrolyte solution that was sufficiently dried, as discussed in detail below in connection with FIG. 23 and the discussion of optimizing the gel electrolyte. FIG. 21 graphically illustrates the CV curve initially and shows the change after 50,000 cycles, with white squares corresponding to the data initially, and black squares corresponding to the data after 50K cycles, for a ~100 nm film.

With respect to optimizing a counter electrode for durability and performance, the counter-electrode material should be chemically stable, providing electrically high conductivity as well as ease of processing into a patterned substrate. Thus, Au and carbon were selected as the electrically conductive materials for making the counter-electrode. Since the electric conductivity of Au is much higher than carbon, Au was directly deposited on the glass without ITO, while graphite was patterned on glass plates with ITO, as described above. Patterns with wide lines of conductive material and small open areas are expected to provide higher conductivity, thus enhancing the color change speed of EC polymer, at the cost of decreasing light transmittance of the counter-electrode. Therefore, the use of a highly conductive material and optimum pattern geometry of the electrode are key design parameters. As a result, the graphite patterned with ITO glass substrate was used as the carbon-based counter-electrode for subsequent experiments.

The percent transmittance (% T) of the Au and carbon counter-electrodes were measured and compared with the transmittance of optical glass (Hitachi glass). The results are shown in FIG. 27. Both the Au-based and carbon-based ITO counter-electrodes did not significantly reduce the transmittance, as shown by the high % T compared to the Hitachi glass. The only exception was that of the carbon-based ITO sample with a 6 μm line width and 0.1 mm window size. The low transmittance value of 75% is a result of the large amount of carbon present on the counter-electrode.

The stability of the counter-electrode over a lifetime of 10,000 cycles was tested using cyclic voltammetry (CV). Because the change in the CV curve after 10,000 cycles was minimal for both the Au and carbon counter-electrodes, it was concluded that the counter-electrode did not undergo significant degradation.

After the three components were well characterized (the EC polymer, the gel electrolyte, discussed in detail below, and the counter electrode), a 3"×3" EC device was assembled. FIGS. 20E and 20F are respectively images of the transparent and colored stages of this device.

It was observed that a much higher E-field and time was needed to switch the device between the opaque and transparent states (±2.8V for 4 seconds) compared to that required to switch the EC polymer film in an electrolyte solution. An alternative device was made to further investigate the reason for the higher potentials. As shown in FIG. 20D, an additional Ag foil sheet was placed in contact with the gel electrolyte, but separated by parafilm from the counter-electrode and EC film polymerized on ITO glass.

The resulting device switched at lower potentials and achieved the same % ΔT (60%), as indicated in FIGS. 29A and 29B, in 1 second compared with the device assembled without the Ag foil (see FIGS. 18A-18B). It is also noted that operating the device with a reference electrode enables the applied voltage to remain constant, while also preventing damage to the EC film, which can occur sometimes when a potential greater than 3 V is applied in the EC film side during the electrochemical reaction (the reaction is described in detail below in connection with FIG. 30). FIG. 29A graphically illustrates the chronoamperogram and resulting transmittance data for the 1"×1" carbon-based counter electrode EC device, and FIG. 29B graphically illustrates the chronoamperogram and resulting transmittance data for the 1"×1" Au-based counter electrode EC device.

Two 3"×3" devices were also prepared: one with and the other without the Ag reference layer shown in FIG. 20D, for comparison. The device without the Ag reference layer achieved a transmittance change of % ΔT over 60%; however, the applied potentials and step times differed significantly. By adding the additional Ag reference layer, the potentials of the 3"×3" device were well controlled, to about 1.0 V between reference and working electrode, and the time required for color saturation dropped from about 8 seconds to about 1 second. Thus, another aspect of the present invention is an EC device that includes a reference electrode in addition to a counter electrode. The reference electrode can be implemented as an Ag layer, or a different electrode material can be employed, if empirical data indicates another electrode material would be desirable.

Empirical studies have indicated that EC devices consistent with the EC device of FIGS. 18A & 18B exhibit a rapid switching speed between a transparent state and a colored state, i.e., less than 1.0 second for a 1"×1" device. Carbon-based counter-electrodes with ITO can achieve faster response times with an applied voltage of 2 V, compared to Au-based counter-electrode. Studies of the blue EC polymer ProDOT-Me2 indicate repeatability over 50,000 cycles. The power consumption of the smart window design of FIGS. 18A, 18B, and 20A-20F are modest (2.5V×20 mA=0.05 W). The temperature range under which switching between states is stable is wide, i.e., from about −40° C. to about 100° C. Furthermore, the total package weight of the smart window design of FIGS. 18A, 18B, and 20A-20F can readily be minimized, which enables such designs to be used for many different applications. The EC polymer devices described above provide a memory effect, good perceived contrast, and low switching voltage.

Gel Electrolytes

An important component of an EC device is the electrolyte, which must be ionically conductive, but electronically insulating. The use of a semi-solid (or gel) electrolyte is preferred. Such gel electrolytes generally are formed by combining an alkali metal salt (a source of ions) with a polymer host (for stability). For a gel electrolyte to be suitable for smart windows or smart displays, it is important that the gel electrolyte provide high ionic conductivity, high light transmittance (i.e., be optically clear), and be stable over a wide range of time and temperatures. High ionic conductivity is essential in an EC device, because the ions need to freely and quickly migrate within the polymer matrix. Electric conductivity should be negligible, so that the device does not short circuit. For smart window applications, a high light transmittance is also important to maximize the transparency of the window in the bleached state. Stability is equally vital in an EC device. There should be minimal change in conductivity and transmittance for gel electrolytes measured over time and at various temperatures. These parameters can vary, depending on the salt and solvent combinations used.

In general, gel electrolytes offer superior conductivity compared to entirely solid polymer electrolytes. While liquid electrolytes can be employed, gel electrolytes offer the advantages of mechanical stability (thus facilitating leak-fee devices), low weight, and established lifetimes of at least 50,000 cycles, as empirically determined. In a gel electrolyte, the solid polymer matrix of PVC and PMMA provide dimensional stability to the electrolyte, while the high permittivity of the solvents enables extensive dissociation of the lithium salts. The low viscosity of the solvents provides an ionic environment that facilitates high ionic mobility. A variety of different combinations of salts and solvents have been studied to determine optimum combinations.

Highly conductive gel electrolytes have been synthesized from a salt dissolved in an electrolyte solution with the polymer matrix, with PMMA added for dimensional stability. Several different gel electrolytes have been compared for use in EC devices. The ionic conductivity over time and at various temperatures have been investigated, along with the transmittance and stability. Lithium (Li), one of the salts investigated, is commonly used in EC switching devices due to its small size and because it facilitates the reduction and oxidization of EC polymers. Another salt, tetrabutyl ammonium phosphate (TBAP), was also used in the comparison. Overall, the salt must have a high degree of dissociation and the anion must have a high level of charge delocalization so that the ion-pairing is minimized. Seven kinds gel electrodes were prepared as described in detail below. The ionic conductivity measurements were recorded at ambient temperature for 90 days, as indicated in FIG. 22. Of the seven, GBL/PC/LiClO$_4$/PMMA and EtC+PC/LiCO$_4$/PMMA seem to be the most promising candidates to optimize a smart window device due to their high ionic conductivities, transmittances, and stability.

The lifetime of EC polymer films have been successfully tested in both an electrolyte solution, as shown in FIG. 23, and also in a gel electrolyte, for 50,000 cycles. The EC polymer tested was a 7×10 mm$^2$ polymer film, Poly[3,3-dimethyle-3,4-dihydro-2H-thieno[3,4-b][1,4]dioxepine] (PProDOT-Me2). Referring to FIG. 23, data after 10,000 cycles is indicated by white squares, data after 25,000 cycles is indicated by triangles, and data after 50,000 cycles is indicated by black squares. A close examination of the CV curves reveals that most of the film degradation occurred within the first 5000 cycles. After 5000 cycles, the rate of degradation significantly decreased. From 25,000 to 50,000 cycles, minimal degradation is observed. One possible explanation of the degradation is due to residual moisture in the electrochemical cell and on the EC film, which can be concluded by the presence of bubbles that formed around the counter-electrode.

Gel Electrolyte Preparation

All materials were obtained from Aldrich Chemical. The solvents, PC, acetonitrile (ACN), γ-butyrolactone (GBL), and EtC were dried over molecular sieves to remove any residual water. The PMMA was vacuum dried. Lithium perchlorate (LiClO$_4$), trifluorosulfonimide (LiN(CF$_3$SO$_2$)$_2$), and TBAP were first vacuum dried and then dissolved in the solvent. PMMA was added to the electrolyte solution, and the mixture was stirred for twenty-four hours under flowing inert gas to ensure the composition was homogeneous. In the case of the ACN and PC solvent combination, no heat was added at any time, to prevent color change, and to ensure a homogeneous gel electrolyte. In all other solvent combinations, the mixture was stirred while slowly increasing the temperature to 60° C. The gel electrolytes were sealed in beakers under argon gas and stored in a desiccator. Seven gel electrolyte candidates are shown in Table 1.

TABLE 1

Gel Electrolyte Candidates

| | Gel Electrolyte |
|---|---|
| 1 | ACN/PC/LiN(CF$_3$SO$_2$)$_2$/PMMA |
| 2 | EtC + PC/LiN(CF$_3$SO$_2$)$_2$/PMMA |
| 3 | ACN/PC/LiClO$_4$/PMMA |
| 4 | EtC + PC/LiClO$_4$/PMMA |
| 5 | GBL/PC/LiN(CF$_3$SO$_2$)$_2$/PMMA |
| 6 | GBL/PC/LiClO$_4$/PMMA |
| 7 | EtC + PC/TBAP/PMMA |

The ionic conductivity of each gel electrolyte was calculated using the complex impedance method. The gel electrolytes were pressed between two polished steel electrodes at a fixed thickness and sealed in a container with inert gas. The AC impedance measurements were made using a PARSTAT 2263 electrochemical system operating in the frequency range of 20 Hz to 1 MHz, with an excitation signal of 10 mV. To determine the temperature dependence of the gel electrolytes, an environmental test chamber was used to control the temperature over the operating range of −35° C. to 80° C. The samples were stabilized for 90 minutes at each temperature before a reading was taken.

Differential scanning calorimetry (DSC) was used to characterize the thermal stability of the gel electrolytes. A DSC6™ (from Perkin Elmer Instruments) heated and cooled the samples at a rate of 25° C. per minute in a nitrogen atmosphere. The samples were cooled, heated, and then cooled again to confirm the thermal stability over the operating temperature range of EC smart window (−35° C. to 80° C.).

Transmittance data was obtained using a Jasco V570 UV-VIS-NIR™ spectrophotometer scanning a wavelength range from 390-800 nm. The transmission results were taken from a wavelength of 580 nm, which corresponds to a PProDOT-Me2 EC polymer smart window operating wavelength.

As noted above, lithium is commonly used in EC switching devices due to its environmental stability, and ease in reducing and oxidizing EC polymers. Denoting X as the anodic portion of a Li salt (LiX), the anodic part of LiX influences the conductivity and stability of the gel electrolyte. Overall, the salt must have a high degree of dissociation, and the anion must have a high level of charge delocalization, so that the ion-pairing is minimized. The gel electrolyte candidates chosen for a smart window EC device were influenced by the extensive research already completed in this area. Recent research showed the EtC:PC ratio is optimized at about 1:1.4. While PC is a suitable solvent due to its high dielectric constant (64.42 at 25° C.), low freezing point (−49° C.), high boiling point (BP (241° C.) and its plasticizing properties, EtC was added to further increase the ionic conductivity. The binary solvents increased the dielectric constant to 89 at 25° C. and lowered the viscosity, facilitating faster ion mobility. Binary solvents were also used in the other candidates, so that synergistic effects of both solvents are present. Because increasing the liquid electrolyte promotes ionic conduction, but weakens mechanical strength, the ratios tabulated in Table 1 were used and represent the best combination for the EC device.

The ionic conductivity measurements were recorded at ambient temperature for approximately 90 days, as exhibited in FIG. 22. CAN-based gel electrolytes showed a loss in ionic conductivity and instability over time. Furthermore, the viscosity noticeably increased, most likely due to the higher volatility of ACN (BP=81-82° C.). On the other hand, GBL+PC and EtC+PC binary solvents were stable over time, which is attributed to the lower vapor pressure of the solvents, with the GBL/PC/PMMA/LiClO$_4$ conductivity higher than the other binary solvent gel electrolytes. When comparing the perchlorate salt to the imide salt, the former was slightly more ionically conductive than the latter, and ionic conductivity of TBAP is about midway between that of these two salts.

FIG. 24 shows the Arrehenius plots for the seven gel electrolyte candidates of Table 1. The Arrehenius plots were generated from the data collected when determining the temperature dependence of the gel electrolytes. The conductivity measurements from the linear portion of the Arrehenius plot were used in the following equation to determine the activation energy, Ea:

$$\sigma = \sigma_o e^{Ea/kT}$$

where σ is ionic conductivity, k is the Boltzmann constant and T is the temperature in degrees Kelvin. The activation energies for the gel electrolytes are tabulated in Table 2.

TABLE 2

Activation energies for Gel Electrolyte Candidates

| | Gel Electrolyte | Activation Energy (kJ/mol) |
|---|---|---|
| 1 | ACN/PC/LiN(CF$_3$SO$_2$)$_2$/PMMA | 11.6 |
| 2 | EtC + PC/LiN(CF$_3$SO$_2$)$_2$/PMMA | 14.7 |
| 3 | ACN/PC/LiClO$_4$/PMMA | 13.2 |
| 4 | EtC + PC/LiClO$_4$/PMMA | 13.2 |
| 5 | GBL/PC/LiN(CF$_3$SO$_2$)$_2$/PMMA | 9.4 |
| 6 | GBL/PC/LiClO$_4$/PMMA | 9.7 |
| 7 | EtC + PC/TBAP/PMMA | 14.0 |

The curvature of the data points followed non-Arrhenius behavior, which is characteristic of amorphous polymer electrolytes in this temperature range. The continuous and non-Arrhenius curves also suggest that no phase transition occurred over the temperature range. A rise in temperature noticeably increased the conductivity, suggesting the proportion of the amorphous phase increased.

DSC was used to monitor the gel electrolyte stability over the operating temperature range. The DSC curves shown in FIG. 25 indicate no thermal decomposition or phase change, as seen by the featureless plots of the gel electrolytes in the range of −35° C. to 80° C.

Equally important for the smart window device is the high light transmittance of the gel electrolyte. The transmittance data for the candidate electrolytes of Table 1 pressed between two glass slides is shown in FIG. 26. The data were collected just after preparation and again, after six months. Based on these results, it is evident that all gel electrolytes exhibit high light transmittance, with minimal loss over time. However, ACN-based gel electrolytes showed a slightly larger loss than the other candidates and appeared to discolor during storage. This result is most likely due to the absorption of water, which might have occurred over a long period of time. Since the maximum % T of the EC polymer film is lower than that of the gels, it can be concluded that the loss of transmittance due to the gel electrolyte component is negligible with respect to the device. The black diamonds in this Figure represent measurements taken after six months in storage under inert gas, and the column height represents transmittance just after preparation of the indicated components.

The ionic conductivity, transmittance, and stability over time for the gel electrolytes are summarized below in Table 3. Overall, the seven candidates demonstrated conductivities >10-3 Scm-1 for temperatures at 0° C. and greater. Also, all candidates, except ACN-based gel electrolytes, exhibited electrochemical stability after three months of storage. Of the seven, GBL/PC/LiClO4/PMMA and EC+PC/LiClO4/PMMA seem to be the most promising candidates to optimize the smart window device due to their high ionic conductivities, transmittances, and stability. The smaller size of the lithium ion is also more beneficial than the much larger TBAP ion when doping the EC film.

TABLE 3

Comparison of Transmittance, Stability, and Conductivity for Various Gel Electrolytes

| | Gel Electrolyte | % Trans. | Stability Over Time (room temp.) | Conduct. mS/cm |
|---|---|---|---|---|
| 1 | ACN/PC/LiN(CF$_3$SO$_2$)$_2$/PMMA | 88.8 | unstable | n/a |
| 2 | EtC + PC/LiN(CF$_3$SO$_2$)$_2$/PMMA | 89.1 | stable | 1.8 |
| 3 | ACN/PC/LiClO$_4$/PMMA | 88.4 | unstable | n/a |
| 4 | EtC + PC/LiClO$_4$/PMMA | 87.4 | stable | 2.3 |
| 5 | GBL/PC/LiN(CF$_3$SO$_2$)$_2$/PMMA | 89.4 | stable | 2.0 |
| 6 | GBL/PC/LiClO$_4$/PMMA | 89.7 | stable | 3.9 |
| 7 | EtC + PC/TBAP/PMMA | 84.6 | stable | 2.8 |

Of the seven different gel electrolytes for use in EC devices prepared, all the gel electrolyte candidates exhibited conductivities >10$^{-3}$ S/cm for temperatures at 0° C. and greater. All candidates exhibited electrochemical stability that did not change after 3 months of storage, except for those including ACN as a solvent. Overall, the electrolyte comprising LiClO$_4$, PMMA, PC, and GBL exhibited higher conductivity than the other candidates, while maintaining stability over time at room temperature and a high transmittance, making it the prime candidate for an EC smart window. However, the LiClO$_4$, PMMA, PC, and EtC gel electrolyte is also a promising candidate for the same reasons. Thus, one aspect of the present invention is an EC device including a gel electrolyte comprising LiClO$_4$, PMMA, PC, and GBL, and another aspect of the present invention is an EC device including a gel electrolyte comprising LiClO$_4$, PMMA, PC, and EtC.

Overview of Paired PProDOT-Me$_2$ & Counter-Electrode Functionality

PProDOT-Me$_2$ can be used as a cathodically coloring polymer. PProDOT-Me$_2$ is dark blue color in its fully reduced form, and a very transmissive light blue in its fully oxidized form. This cathodically coloring polymer changes from a light color to a highly colored state upon charge neutralization (i.e., during reduction) of the p-doped form. The π–π* transition is depleted at the expense of transitions outside the visible region. Therefore, the dominant wavelength of the color is the same throughout the doping process. The EC process of an EC device utilizing a PProDOT-Me$_2$ cathodic layer, a gel electrolyte containing lithium perchlorate (LiClO$_4$), and a gold-based counter-electrode is illustrated in FIG. 27, where the gold layer plays the role of the second layer required in the paired layer process explained below.

The EC process requires paired layers, with the PProDOT-Me$_2$ layer acting as a first one of the paired layers, and the gold-based counter-electrode acting as a second one of the paired layers. In the left side of FIG. 27, a negative voltage has been applied and the PProDOT-Me$_2$ polymer is in its reduced, highly blue-colored state. The gold-based counter-electrode layer is attracting the negatively charged perchlorate (ClO$_4$) ions. In the right side of FIG. 27, no voltage (or a positive voltage) is being applied, and the PProDOT-Me$_2$ polymer is in its oxidized, p-doped, light-color state. The gold-based counter-electrode layer is attracting positively charged lithium (Li) ions.

The gel electrolyte separating the PProDOT-Me$_2$ polymer layer and the gold-based counter-electrode layer is ionically conductive, but electronically insulating, so the lithium and perchlorate ions are mobile and free to move between the PProDOT-Me$_2$ polymer side and the gold-based counter-electrode side, under a polarity change due to an applied potential.

The graphite-based counter-electrode works by the same mechanism. This electric double layer results in no chemical reaction, and causes no structural change in the counter-electrode layer (gold or graphite). The electric double layer can store both negative and positive charges.

Specific Applications

Yet another aspect of the present invention relates to specific applications for EC devices. In a first application, an EC device including one of the EC polymers described in detail above is employed as a display. By combining multiple EC devices into a single structure, a multicolor display can be achieved. For example, a single layer EC device including a blue polymer can be combined with a single EC device including a red polymer to achieve a display including red and blue. Depending on the relative positions of the red and blue EC polymers, such a combination device can be configured to display red and blue, or at the two EC polymers can be overlapped such that a black color is achieved (generally as described above in connection was subtractive color mixing), or both. Such EC devices can include a plurality of pixels, each pixel being defined by an individually addressable grid of a EC polymer device. A voltage can be applied to each pixel individually, enabling a flat panel display to be achieved in which the color of each pixel is separately controlled. The EC polymers described above can be used to develop pixilated devices capable of displaying clear pixels, red pixels, blue pixels, and black pixels. Furthermore, the EC devices of the present invention are of special interest for use in dialed-tint windows and large area displays.

Referring now to FIGS. 20E and 20F, it will be evident that a logo has been incorporated into the EC device. When the EC polymer is in the transparent state, the logo is readily visible. When the EC polymer is in the colored state, the logo is obscured. The logo can be incorporated into an EC device as either an additional layer, or into one of the existing layers. For example, referring to FIG. 20C, a logo can be incorporated into either the transparent insulating substrate, or into the ITO transparent film, as long as incorporation of such a logo does not interfere with the required electrical charge conduction within the EC device.

Referring to FIG. 20D, a logo can be additionally incorporated into either parafilm layer. With respect to both FIGS. 20C and 20D, an additional layer of a substantially transparent material onto which the logo has been incorporated can be added to the layered structure. It should also be understood that such a logo layer can be incorporated into any of the other EC devices described herein, including those EC devices described in connection with FIGS. 17A, 17B, 18A, 18B, and 20A-20D. Such logos have widespread application. For example, the logo of an airline could be incorporated into each passenger window of the aircraft, and the mechanical shutters for each window can be eliminated. If the passenger wants to block/reduce light transmission through the window, the EC polymer is placed in the colored state, and the logo will be generally obscured. If the passenger prefers that the window be transparent, the EC polymer will be in the transparent state, and the logo will be visible in a portion of the window. Of course, the logo can be positioned prominently within the window, or can be positioned such that the view through the window is substantially unaffected, yet the logo is still apparent to the passenger.

Figure 31A:
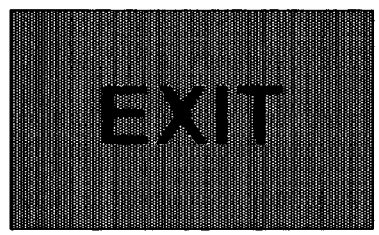
Figure 31B:
Figure 31C:
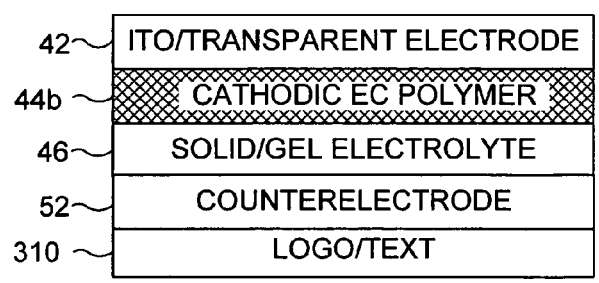

Yet another significant application for this logo type technology is signage, particularly emergency signage. The ubiquitous emergency exit signs and buildings and aircraft can be replaced by an EC device in which the logo shown in FIGS. 20E and 20F is replaced with the word "EXIT." In the colored state, an observer will just see a colored panel, generally as indicated in FIG. 31A. In the transparent state, particularly if a light source is disposed in the EC device, the EXIT text will be clearly displayed, generally as indicated in FIG. 31B. It should be understood that these examples of the use of an EC device to present a logo or text for windows and signage are merely exemplary, and are not intended to limit the invention. FIG. 31C schematically illustrates the layers of an EC device used for signage (or a smart window including a logo). Note this arrangement is similar to that shown in FIGS. 18A and 18B, with the incorporation of an additional layer for the logo/text. A top layer is transparent electrode 42 (preferably ITO). The next layer is a cathodic EC polymer, then solid/gel electrolyte layer 46, followed by counter-electrode layer 52. A layer 310, a transparent material onto which the logo/text has been formed, is then added. Layer 310 can readily be implemented using conventional printing techniques and a transparent sheet. The logo, design or text is printed onto the transparent sheet, and the transparent sheet is incorporated into the layered structure shown in FIG. 31C. It should be understood that layer 310 could be positioned elsewhere in the layered structure (for example on top rather than on the bottom), as long as the incorporation of layer 310 does not interrupt the flow of electrical charges within in the various layers of the EC device required to enable the EC polymer to transition from the first state (generally a colored state) to the second state (generally a transparent state). If desired, the logo/text could be incorporated into one of the transparent electrode and the counter electrode, as long as incorporation of the logo/text on to either electrode does not interfere with the functioning of the EC polymer.

Figure 31D:
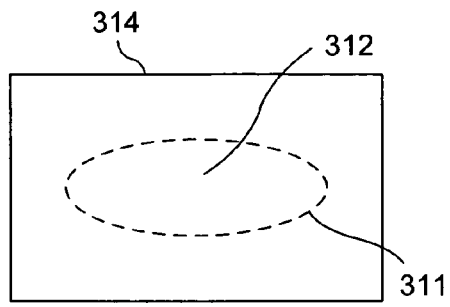
Figure 31E:
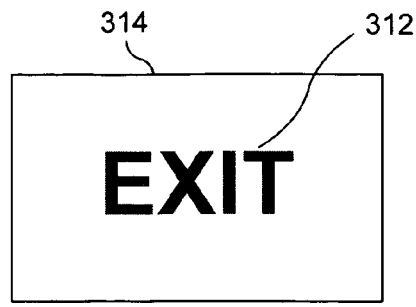

FIGS. 31D and 31E schematically illustrate another embodiment of using EC polymers in smart windows to selectively display a logo, text or graphics. A portion 311 of smart window 314 includes an EC polymer 312. The EC polymer can be implemented using one of the layered design of FIG. 17A, 18A, 20A-C, or 31C. It should be understood however, that such designs are merely exemplary, and are not intended to limit the implementation of logos, text or graphics into a smart window. The EC polymer incorporated into smart window 314 will be substantially transparent in a first state and colored in a second state. Thus FIG. 31D corresponds to smart window 314 with EC polymer 312 in a substantially transparent state, such that a viewer may not even notice the EC polymer 312 has been incorporated into smart window 314 (and with respect to FIG. 31D the specific position and shape of EC polymer 312 within portion 311 is not indicated). However, when EC polymer 312 is manipulated (generally as described in conjunction with FIG. 30, and elsewhere the specification), EC polymer 312 will transition to the second state, and will turn substantially opaque (either red, blue or some other color depending on the specific EC polymer or polymers selected). As indicated in FIG. 31E, EC polymer 312 has been incorporated into smart window 314 in the shape of the word "EXIT," such that a viewer will see the word exit appear within smart window 314. Of course, EC polymer 312 can be formed in the shape of a logo, another word or words, or some graphical design. It should be understood that additional EC polymers can be incorporated into the same smart window, such the multicolor word or design can be achieved. Furthermore, generally as discussed in connection with FIG. 36, the principal of subtractive color mixing can be used to achieve additional colors. For example, appropriate overlapping of EC blue polymers and EC red polymers can be used to achieve a logo or design including blue, red, and black colors, which will be substantially transparent when EC polymers are in the transparent state. Smart window 314 has many applications, including emergency signage (such as the exit sign shown here) and advertising (the incorporation of advertising into windows of buildings and vehicles). It should be understood however, that such applications are merely exemplary, and not intended to limit the invention.

Figure 31F:
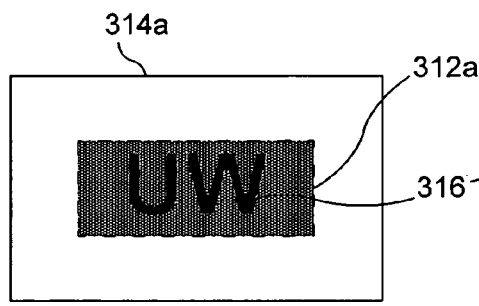
Figure 31G:
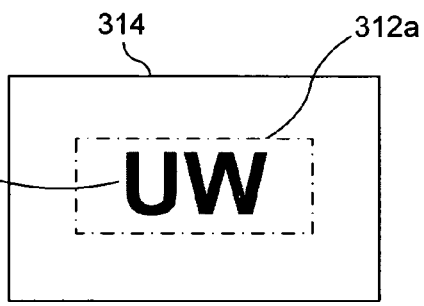

Still another embodiment of smart windows which incorporate EC polymers and selectively displayable logo/text is schematically illustrate in FIGS. 31F and 31G. A smart window 314a includes an EC polymer 312a, and text 316 (as noted above, it should be understood to text 316 can either be text, a logo, or a design). In FIG. 31F EC polymer 312a is in an opaque state, and text 316 is substantially obscured. In FIG. 31G, EC polymer 312a is in an substantially transparent state, and text 316 can be readily observed.

Yet another implementation of an EC device is to function as a shutter in an instrument designed to selectively collect light, generally as indicated in FIG. 32. A light gathering instrument 322 is positioned proximate an object 320. Optional optics 324, such as a lens, can be used to collect light from the object and introduce the light into the light gathering instrument. An EC polymer shutter 326 is disposed between the object and a light sensor 328. EC polymer shutter 326 is coupled to a controller 339, which selectively controls whether EC polymer shutter 326 is in a transparent state or a colored state. While in the colored state, EC polymer shutter 326 blocks substantially all light from reaching light sensor 328. To achieve this, it may be necessary to implement EC polymer shutter 326 using a combination of different EC polymers, to block substantially all wavelengths of light. As discussed above in detail in regard to subtractive color mixing, the mixing of two different colors such as red and blue can achieve a visually perceived black color, which blocks most wavelengths of light.

As indicated in FIG. 32, controller 339 also includes a power source used to energize the EC polymer shutter to enable the EC polymer shutter to transition from the colored state to the transparent state. The power source can be implemented as a separate element that is controlled by controller 339. Those of ordinary skill in the art will recognize that there are many light gathering instruments that generally correspond to light gathering instrument 322. Film cameras, digital cameras, video recorders, digital video recorders, sensors, and a variety of analytical instruments generally correspond to light gathering instrument 322. At present, a switching time of approximately 1 second is generally too great for many practical applications. However, the fact that an EC polymer shutter is a solid-state device consuming relatively low power, is relatively low weight, and offers an extremely long lifetime is reason to believe that as the speed of EC polymer shutter decreases into the millisecond range, they will become more and more attractive as a replacement to a mechanical shutter. Indeed, where shutter speeds of one second or more are acceptable, EC polymer shutters can be implemented at this time. Controller 339 can be implemented as a logical circuit, or simply a mechanical circuit connected to a user actuated switch (not separately shown). Light sensor 328 can be implemented as a light-sensitive film, or an electronic sensor, such as one or more CCD sensors or one or more CMOS sensors.

Another implementation of EC devices in accord with the present invention is for use in antiglare, car rear-view mirrors. FIGS. 35A and 35B schematically illustrate such an implementation. A rearview mirror 352 is coupled to a sensor/controller 350. Those of ordinary skill in the art will recognize that sensor/controller 350 can be implemented as a combined device, or a plurality of separate elements can be used to implement sensor/controller 350. The sensor portion of sensor/controller 350 is configured to determine when the light directed towards rearview mirror 352 is likely to present undesirable glare conditions. In general, the sensor portion of sensor/controller 350 will be disposed proximate rearview mirror 352, and is implemented as an optical sensor. The controller portion of sensor/controller 350 is configured to control the transition of the EC device in rearview mirror 352 from a transparent state to a colored state. Sensor/controller 350 either includes or is controllably coupled to a power source (e.g., the battery system of the vehicle) that can be used to energize the EC device. Under normal driving conditions, the EC device in rearview mirror 352 is in the transparent state, and the rear view mirror reflects light normally. Under glare conditions, the EC device in rear view mirror 352 transitions to the colored state, thereby reducing the amount of light reflected, and minimizing glare. It should be understood that sensor/controller 350 can be replaced by a mechanical switch coupled to a power source that enables the operator to selectively control whether the EC device in rear view mirror 352 is in the colored state or the transparent state. In FIG. 35A, the EC device in rear view mirror 352 is in the transparent state, and in FIG. 35B the EC device in rear view mirror 352 is in the colored state.

Still another application for an EC device is directed to a DW for DNA chip reading technology based on SPR imaging with high lateral resolution. SPR imaging is an accepted technology that currently uses expensive custom photo masks. In this embodiment, a DW including a plurality of individually addressable pixels arranged in a grid format is employed in the place of the conventional photo mask. The DW includes a plurality of individual pixels, each of which is a laminated EC, such as the dual polymer and single polymer devices described above. A voltage can be applied to each pixel individually, enabling selective masking to be achieved, pixel-by-pixel. Thus, a DW provides a switchable window, changeable from transparent to non-transparent (dark blue) by varying an electric potential polarity. The laminated EC devices described above are fabricated in a digital (pixel) array, whose size are typically 0.5-50 microns across.

The impact of the above described DW technology is expected to be multifold and immediately transferable to DNA array chip technology, particularly the technology for reading unknown DNA and unknown molecules (in vitro or in vivo) by using SPR. One example of using a preferred embodiment of a DW in accord with the present invention is shown in FIG. 33A. In FIG. 33A, a DW/SPR imaging system 100 includes a conventional SPR imaging system in which DW 102 is inserted. Conventional elements of DW/SPR imaging system 100 include a flow cell 104, a patterned analytic layer 106, a gold or silver layer 108, a laser light source 110 for directing light to the analytic layer along a first path 112, a first optical element 114 disposed in first light path 112 (for polarizing the light from light source 110), a prism 116 disposed in first light path 112 and adjacent to the analytic layer, such that light traveling along first light path 112 passes through the prism. A second optical element 118 is disposed along a second light path 120, and a charge-coupled device (CCD) detector 122 is disposed in second light path 120 to receive light focused by second optical element 118. Not separately shown are a plurality of electrical conductors coupled to each pixel of the DW, such that a voltage can be individually applied to each pixel, and a power supply electrically coupled to the electrical conductors and the laser light source.

A second example of using a DW in an SPR imaging system is shown in FIG. 33B. A DW/SPR imaging system 100a includes a conventional SPR imaging system in which DW 102a is inserted. Note that system 100a of FIG. 33B is very similar to system 100 of FIG. 33A. The difference between the two systems is the location of the DW. In system 100 (FIG. 33A), DW 102 is disposed between first optical element 114 and prism 116. In system 100a (FIG. 33B), DW 102a is disposed between prism 116 and patterned analytic layer 106.

By combining a DW with a conventional SPR imaging system intended for use as a real time analyzer of unknown molecules, including DNA and RNA sequences, a new SPR system with high spatial resolution is achieved. The high resolution DW/SPR system is expected to analyze unknown molecules and DNA sequences on a real-time basis at a faster rate than can be achieved by conventional SPR imaging systems, by scanning through one group of molecules followed by another group, by opening corresponding pixels for each group in a digital window. The DW can be left in place, and reconfigured for activating different pixels. In contrast, a photo mask would have to be removed and replaced with a different mask to achieve a different masking pattern.

Yet another aspect of the present invention is a smart window that can be used in structural and architectural applications, such as in cars, planes, and buildings. Such a smart window is able to change from a substantially transparent first state, with no voltage (or a positive voltage) applied, to a substantially opaque second state, with a negative voltage applied. FIG. 34 illustrates single or dual polymer EC devices, such as those described above, incorporated into a conventional dual pane window 130. FIG. 34 includes a front view, a side view, and an expanded view, each of which is appropriately labeled. Smart windows differ from conventional windows in that the EC device layered between conventional glass outer pane 134 and inner pane 136, enables wires (not separately shown) extending from the smart window to be coupled to a controllable voltage source, such that the smart window can be selectively transitioned from being generally transparent to being significantly less transparent. If a void or gap 140 separates the panes of conventional glass, the EC device is preferably coupled to outer pane 134, rather than inner pane 136. A first embodiment of a smart window is based on a dual polymer EC device using a ProDOT-Me$_2$ cathodic polymer layer, a solid electrolyte layer, and a PBEDOT-NMeCz anodic polymer layer, as described above. A second embodiment of a smart window is based on a single polymer EC device, using one of the other EC polymers described above as a cathodic polymer layer, a solid electrolyte layer, and a counter-electrode layer, substantially as described above.

Because the dual and single polymer EC devices described above exhibit good perceived contrast and require a low switching voltage, they are expected to be of special interest in other applications as well, such as for large area displays, automatic mirrors, and other applications where color change in response to an applied voltage is desirable.

The use of Vanadium Pentoxide as a Counter Electrode

Yet another aspect of the present invention is the use of the vanadium pentoxide in counter electrodes. FIGS. 18A, 18B, 20C, 20D and 31C each schematically illustrate EC polymer devices which include a counter electrode. The counter electrodes described above have been based on the use of gold or carbon. Vanadium pentoxide, preferably deposited as a film on an ITO substrate, performs quite well as a counter electrode. Indeed, empirical studies have indicated that EC polymer devices consistent with the design schematically illustrated in FIG. 18A and including a vanadium pentoxide based counter electrode have lifetimes in excess of 100,000 cycles, whereas the lifetime of similar devices using gold or carbon counter electrodes have been limited to about 50,000 cycles. Thus another aspect of the present invention is an EC polymer device including a counter electrode comprising vanadium pentoxide.

An EC polymer device including a vanadium pentoxide counter electrode, a gel electrolyte and a cathodic polymer film (PProDOT-Me$_2$) was constructed. The vanadium pentoxide counter electrode was prepared using a sol-gel method and deposited using electrophoresis. Indium Tin oxide (ITO) coated glass was used as an electrically conductive and transparent substrate. The transmittance, ionic capacitance, stability and electrochromic matching diffusion rate of the counter electrode are vitally important parameters for successful smart window applications.

Gels of $V_2O_5 \cdot nH_2O$ were synthesized using a method adapted from Takahashi et al. (K. Takahashi, S. Limmer, G. Cao, Proc SPIE 5224 (2003). Crystalline V2O5 (Alfa Aesar 99.8%) was dissolved in a hydrogen peroxide (Afla Aesar, 30%) solution at a molar ratio of $8:1 H_2O_2$ to $V_2O_5$. The ensuing reaction results in the breakdown of $H_2O_2$ and $V_2O_5$ which reform as $VO^{2+}$ clusters and V(V) peroxo complexes. This $VO^{2+}$ solution appears as a transparent orange solution and changes to a transparent dark red solution after 1 hour of vigorous stirring. Sonicating the solution for 2 hours creates a dark red/brown gel that, studies have shown, leads to $V_2O_5 \cdot nH_2O$ layers upon drying. The gel was then dispersed into water creating a dark red transparent solution having a vanadium ion concentration of 0.005 mol/l and pH≈2.7. The primary species are hydrated vanadium oxide nanoparticles.

Thin films were deposited onto an ITO (8 □resistance/in$^2$) substrate submerged in the solution in a three electrode cell and subjected to cyclic voltammetry (CH 1605A, CH Instruments, Electrochemical Analyzer) using a Platinum wire counter electrode and silver wire reference electrode. Parameters varied during deposition include deposition speed 5-150 mV/s, applied voltage 1-3 V, deposition cycles 10-100, substrate angle 60-90 degrees, and a baking temperature of 100-500° C. Excess liquid was removed and the films were baked at 110° C. for 8 hours to remove moisture. Deposition parameters were adjusted and combine to perform a full factorial of experiments and repeated for statistical accuracy. Successful deposition techniques were repeated on larger sized substrates to test scalability effects. Because of the expense of larger sized ITO these tests were limited.

A three electrode cell containing a 1 M solution of $LiClO_4$ in propylene carbonate solvent was used to switch the films. Chronoamperometry was performed (CH Instruments, Electrochemical Analyzer) at ±1.5V vs. Platinum (Pt) wire for 200s. Intercalation and de-intercalation curves were recorded along with lifetime. In-situ transmittance in the range of 350-750 nm was measured via UV-VIS-NIR spectrophotometry (JASCO V-570 UV-VIS-NIR spectrophotometer).

A $PProDOT-Me_2$ EC polymer film was prepared from 0.01 M TBAP/ACN solution and deposited on ITO. Gel electrolyte based on PMMA and Lithium perchlorate was plasticized by propylene carbonate and ethylene carbonate. The device was assembled in a sandwich structure; ITO, EC polymer film, gel electrolyte, ion storage layer, ITO, and sealed with a ultra-violet curing epoxy (OG112-4, Epoxy Technology). Assembly was conducted in an argon environment within a glove box.

The goal of using vanadium oxide is to produce a counter electrode complimentary to the $PProDOT-Me_2$ based EC polymer. Maintaining a photo spectra transmissivity greater than 60% in the reduced state and a short term capacitance curve similar to the EC polymer are necessary in order to use vanadium oxide as a counter electrode. Capacitance results are therefore discussed with respect to short term intercalation, less than 10 seconds, and constant transmissivity of 60%.

Studies have shown that surface morphology can be altered during physical deposition techniques by changing the angle at which the material is deposited, resulting in a wave like surface which increases capacitance through increased surface area. This technique does not appear to work in electrochemical deposition. Varying the angle of the substrate with respect to the platinum counter electrode wire resulted in varying thickness film that decreased as the distance between the substrate and the platinum wire increased. Chronoamperometry showed a decrease in capacitance with increased angle.

Varying both the deposition cycles and voltage showed the predicted proportional relationship between increased voltage or cycles, and increased total capacitance. Neither parameter significantly affected the slope of the short term capacitance curve. Changes to the pH of the vanadium solution resulted in light or absent deposition.

Films deposited with varying sweep speeds exhibited a proportional relationship. Increased $Li^+$ absorption rates were observed as sweep speed was varied from 20 to 100 sweeps. Faster depositions tend to create rougher surfaces which, in turn, provide a greater number of immediately accessible intercalation sites. Therefore the rate at which ions are intercalated is increased while the thickness, the overall capacitance, and the transmissivity of the film remains the same as films deposited using a lower sweep speed.

Lifetime of the vanadium oxide counter electrode was tested by repeatedly reducing and oxidizing the counter electrode using chronoamperometry. Good repeatability was observed. Over 75,000 cycles the current change is less than 0.2 mA. FIG. 37 graphically illustrates the repeatability of the $V_2O_5$ thin film under varying polarity, and a constant potential of 1.5V, with switching at 1 second intervals.

The availability of surface ion intercalation sites must be consistent across the counter electrode film as well as the EC film in order to preserve the charge balance. Aesthetics must also be considered in any potential consumer product and visual defects are unacceptable. Uniformity of the deposited vanadium oxide was determined under visual inspection of the film coloration which would vary with any significant thickness variation. It was determined that thin films can be created uniformly on substrates up to 12 inches in size. To achieve a uniform deposition of this size it was necessary to employ a conductive copper border on the edge of the ITO on which the potential was applied. Lack of a conductive copper border resulted in an inhomogeneous film decreasing in thickness outwards from the point of applied potential. The copper border was removed after deposition. FIG. 38 is a photograph of a uniform vanadium pentoxide film produced as described, indicating where the electric potential was applied to deposit the film. When assembled into an EC device, the slight yellow tint does not appear to significantly detract from the usability of the vanadium pentoxide film as a counter electrode, even in applications where high transmittance is desirable.

By optimizing the deposition sweeps, sweep speed, and voltage, a thin film of layered vanadium oxide with a short period charge absorption curve comparable to that of the $PProDOT-Me_2$ electrochromic layer was achieved. The film was deposited on a 1 inch×1 inch, 10Ω ITO substrate cleaned with a 10% acetonitrile solution, using cyclic voltammetry from 1.5V to 2.5V vs. an Ag reference electrode and a 100 mV/s sweep speed for 23 sweeps. Excess liquid was removed and the film was baked for at 110° C. for 8 hours to remove moisture. The film exhibited a minimum transmissivity, in the visible range, of 60%. FIG. 39 graphically illustrates short term charge capacitance data for this 1 inch×1 inch vanadium oxide thin film, while FIG. 40 graphically illustrates transmittance data for the 1 inch×1 inch vanadium oxide thin film.

A 1 inch×1 inch EC polymer device using a vanadium oxide counter electrode described above exhibited a contrast ratio ΔT of 60% from 2% in the fully colored state to 62% in the bleached state. A lifetime of 100,000 cycles, when switched at 1 second intervals using a ±1.5V electric potential, with a less than 6% decrease in transmissivity was achieved. FIG. 41 graphically illustrates transmittance data for the EC polymer device including a vanadium pentoxide counter electrode over 1000,000 cycles, with the solid line corresponding to the first 5 cycles, and the dash line corresponding to the last 5 cycles. FIG. 42 graphically illustrates transmittance data for the EC polymer device including a vanadium pentoxide counter electrode in both oxidized and reduced states, with a line 420 corresponding to the bleached or oxidized state, and a line 422 corresponding to the reduced or colored state.

Optimized deposition parameters for the 1 inch counter electrode were unsuccessful when applied to 6 and 12 inch substrates. As mentioned, it was necessary to employ a copper border to decrease the effective resistance across the ITO and increase uniformity of the thin films. Increasing the voltage from 1.5-2.5V to 2.0-3.0V and the number of sweeps from 23 to 75 resulted in a uniform vanadium oxide thin film.

Although the present invention has been described in connection with the preferred form of practicing it and modifications thereto, those of ordinary skill in the art will understand that many other modifications can be made to the present invention within the scope of the claims that follow. Accordingly, it is not intended that the scope of the invention in any way be limited by the above description, but instead be determined entirely by reference to the claims that follow.

The invention in which an exclusive right is claimed is defined by the following:

1. An electrochromic device comprising:
   (a) a transparent electrode layer;
   (b) a cathodic polymer layer;
   (c) an electrolyte layer comprising a solid electrolyte;
   (d) a reference electrode electrically coupled to the electrolyte layer, the reference electrode increasing a speed with which the device switches between a first state and a second state; and
   (e) a counter electrode layer.

2. The electrochromic device of claim 1, wherein the cathodic polymer layer comprises PProDOT-MePro.

3. The electrochromic device of claim 1, wherein the cathodic polymer layer comprises PProDOP-Et2.

4. The electrochromic device of claim 1, wherein the reference electrode comprises silver.

5. The electrochromic device of claim 1, further comprising at least one of a logo, a text, and a graphical image, such that when the electrochromic device is in a first state, the at least one of the logo, the text, and the graphical image is substantially obscured, and when the electrochromic device is in a second state, the at least one of the logo, the text, and the graphical image is readily visible.

6. The electrochromic device of claim 5, wherein the electrochromic device is included in an aircraft window.

7. The electrochromic device of claim 6, wherein the at least one of the logo, text, and the graphical image comprises an airline logo.

8. The electrochromic device of claim 5, wherein the electrochromic device is included in a sign.

9. The electrochromic device of claim 8, wherein the laminated electrochromic device is included in an emergency exit sign.

10. The electrochromic device of claim 1, further comprising:
    (a) an additional transparent electrode layer;
    (b) an additional cathodic polymer layer, the additional cathodic polymer layer having a different color than the cathodic polymer layer;
    (c) an additional electrolyte layer comprising a solid electrolyte; and
    (d) an additional counter electrode layer, such that the cathodic polymer layer and the additional cathodic polymer layer are configured to enable the electrochromic device to achieve a different color using subtractive color mixing.

11. The electrochromic device of claim 1, wherein the counter electrode comprises vanadium pentoxide.

12. An electrochromic device comprising:
    (a) a transparent electrode layer;
    (b) a cathodic polymer layer;
    (c) an electrolyte layer comprising a solid electrolyte;
    (d) a counter electrode layer; and
    (e) at least one of a logo, a text, and a graphical image, such that when the electrochromic device is in a first state, the at least one of the logo, the text, and the graphical image is substantially obscured, and when the electrochromic device is in a second state, the at least one of the logo, the text, and the graphical image is readily visible.

13. The electrochromic device of claim 12, wherein the electrochromic device is included in an aircraft window.

14. The electrochromic device of claim 12, wherein the laminated electrochromic device is included in an emergency exit sign.

15. The electrochromic device of claim 12, further comprising a reference electrode electrically coupled to the electrolyte layer, the reference electrode increasing a speed with which the device switches between a first state and a second state.

16. The electrochromic device of claim 12, wherein the counter electrode comprises vanadium pentoxide.

17. An electrochromic device comprising:
    (a) a transparent electrode layer;
    (b) a cathodic polymer layer comprising PProDOT-Me$_2$;
    (c) an electrolyte layer comprising a solid electrolyte, such that the cathodic polymer layer is disposed between the electrolyte layer and the transparent electrode; and
    (d) a counter electrode layer comprising vanadium pentoxide, the counter electrode layer being separated from any electrochromic polymer component by the electrolyte layer, the counter electrode layer having a transmissivity of at least about 60%.

18. The electrochromic device of claim 12, wherein the at least one of the logo, the text, and the graphical image is incorporated into the transparent electrode layer.

19. The electrochromic device of claim 12, wherein the at least one of the logo, the text, and the graphical image is incorporated into the counter electrode layer.

20. The electrochromic device of claim 12, wherein the at least one of the logo, the text, and the graphical image is implemented as an additional layer.

21. The electrochromic device of claim 12, further comprising a substantially transparent insulating layer, wherein the at least one of the logo, the text, and the graphical image is incorporated into the substantially transparent insulating layer.

22. The electrochromic device of claim 12, wherein the at least one of the logo, the text, and the graphical image is incorporated into a substantially transparent layer in the electrochromic device.

23. The electrochromic device of claim 12, wherein the at least one of the logo, the text, and the graphical image is unchanging, such that the state of the electrochromic device simply determines whether the at least one of the logo, the text, and the graphical image is visible, the at least one of the logo, the text, and the graphical image itself being unchanged by the state of the electrochromic device.

24. An electrochromic device comprising:
    (a) a transparent electrode layer;
    (b) a cathodic polymer layer;
    (c) an electrolyte layer comprising a solid electrolyte;
    (d) a reference electrode electrically coupled to the electrolyte layer, the reference electrode increasing a speed with which the device switches between a first state and a second state, the reference electrode layer being spaced apart from the transparent electrode layer; and (e) a counter electrode layer, the counter electrode layer being spaced apart from the reference electrode layer and the transparent electrode layer.

25. An electrochromic device comprising:
(a) a transparent electrode layer;
(b) a cathodic polymer layer comprising PProDOT-Me-Pro;
(c) an electrolyte layer comprising a solid electrolyte;
(d) a reference electrode electrically coupled to the electrolyte layer, the reference electrode increasing a speed with which the device switches between a first state and a second state; and
(e) a counter electrode layer.

26. An electrochromic device comprising:
(a) a transparent electrode layer;
(b) a cathodic polymer layer comprising PProDOP-Et2;
(c) an electrolyte layer comprising a solid electrolyte;
(d) a reference electrode electrically coupled to the electrolyte layer, the reference electrode increasing a speed with which the device switches between a first state and a second state; and
(e) a counter electrode layer.

27. A subtractive color mixing electrochromic system comprising:
(a) a first electrochromic device comprising a first electrochromic polymer, the first electrochromic polymer being switchable between a first state and a second state, the first electrochromic polymer exhibiting a first color in the first state, whereas in the second state, the first electrochromic polymer is at least one of:
(i) a second color that is different than the first color; and
(ii) generally transparent;
(b) a second electrochromic device comprising a second electrochromic polymer, the second electrochromic polymer being switchable between a first state and a second state, the second electrochromic polymer exhibiting a first color in the first state, whereas in the second state, the second electrochromic polymer is at least one of:
(i) a second color that is different than the first color; and
(ii) generally transparent, at least one color individually achievable by the first and second electrochromic devices being different than other colors individually achievable by the first and second electrochromic devices; and
(c) the first and second electrochromic devices being configured to enable the system to achieve a new color that cannot be individually achieved by the first and second electrochromic devices, the new color being achieved using subtractive color mixing.

28. The subtractive color mixing electrochromic system of claim 27, wherein each electrochromic device comprises:
(a) a transparent electrode layer;
(b) a cathodic polymer layer;
(c) an electrolyte layer comprising a solid electrolyte;
(d) a reference electrode electrically coupled to the electrolyte layer, the reference electrode increasing a speed with which the device switches between a first state and a second state; and
(e) a counter electrode layer.

29. An electrochromic device exhibiting subtractive color mixing, comprising:
(a) a transparent electrode layer;
(b) a cathodic polymer layer;
(c) an electrolyte layer comprising a solid electrolyte;
(d) a reference electrode electrically coupled to the electrolyte layer, the reference electrode increasing a speed with which the device switches between a first state and a second state;
(e) a counter electrode layer;
(f) an additional transparent electrode layer;
(g) an additional cathodic polymer layer, the additional cathodic polymer layer having a different color than the cathodic polymer layer;
(h) an additional electrolyte layer comprising a solid electrolyte; and
(i) an additional counter electrode layer, such that the cathodic polymer layer and the additional cathodic polymer layer are configured to enable the electrochromic device to achieve a different color using subtractive color mixing.

* * * * *

UNITED STATES PATENT AND TRADEMARK OFFICE
CERTIFICATE OF CORRECTION

PATENT NO. : 7,256,923 B2  
APPLICATION NO. : 11/070392  
DATED : August 14, 2007  
INVENTOR(S) : Liu et al.

It is certified that error appears in the above-identified patent and that said Letters Patent is hereby corrected as shown below:

| | |
|---|---|
| Column 3, line 22 | after "such" insert --that-- |
| Column 5, line 20 | after "layer" delete "and" |
| Column 5, line 20 | after "counter-electrode" insert --and-- |
| Column 6, line 23 | "1000,000" should read --100,000-- |
| Column 6, line 53 | after "pixels" insert --that-- |
| Column 12, line 28 | "1%" should read --51%-- |
| Column 14, line 45 | "Polymers" should read --Polymer-- |
| Column 16, line 26 | "polymer" should read --polymer-- |
| Column 16, lines 35-37 | delete "By overlaying different EC films, corresponding absorption bands can be removed from ambient light resulting in new colors." |
| Column 17, line 3 | "theses" should read --these-- |
| Column 17, line 8 | "theses" should read --these-- |
| Column 17, line 17 | "(O)" should read --(Q)-- |
| Column 17, line 66 | after "deposit" (2nd occurrence) insert --the-- |
| Column 20, line 42 | "use" should read --used-- |
| Column 23, line 8 | after "to" delete "the" |
| Column 24, line 11 | "bleed-though" should read --bleed-through-- |
| Column 27, line 34 | after "kinds" insert --of-- |
| Column 31, line 43 | after "or" delete "at" |
| Column 31, line 45 | delete "was" insert therefor --with-- |

UNITED STATES PATENT AND TRADEMARK OFFICE
CERTIFICATE OF CORRECTION

PATENT NO. : 7,256,923 B2
APPLICATION NO. : 11/070392
DATED : August 14, 2007
INVENTOR(S) : Liu et al.

It is certified that error appears in the above-identified patent and that said Letters Patent is hereby corrected as shown below:

| | |
|---|---|
| Column 32, line 25 | delete "and" (1st occurrence) insert therefor --in-- |
| Column 32, line 52 | after "within" delete "in" |
| Column 33, line 22 | after "such" insert --that-- |
| Column 33, line 38 | "illustrate" should read --illustrated-- |
| Column 33, line 40 | delete "to" insert therefor --that-- |
| Column 34, line 13 | "shutter decreases" should read --shutters decrease-- |
| Column 38, line 41 | delete "for" (1st occurrence) |
| Column 38, line 56 | "1000,000" should read --100,000-- |

Signed and Sealed this

Twentieth Day of November, 2007

JON W. DUDAS
*Director of the United States Patent and Trademark Office*